US008071586B2

(12) United States Patent
Aebi et al.

(10) Patent No.: US 8,071,586 B2
(45) Date of Patent: Dec. 6, 2011

(54) HETEROCYCLYL COMPOUNDS

(75) Inventors: Johannes Aebi, Binningen (CH); Alfred Binggeli, Binningen (CH); Luke Green, Basel (CH); Guido Hartmann, Loerrach (DE); Hans P. Maerki, Basel (CH); Patrizio Mattei, Riehen (CH); Fabienne Ricklin, Hombourg (FR); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 184 days.

(21) Appl. No.: 12/499,120

(22) Filed: Jul. 8, 2009

(65) Prior Publication Data
US 2010/0016282 A1 Jan. 21, 2010

(30) Foreign Application Priority Data

Jul. 16, 2008 (EP) .................... 08160534

(51) Int. Cl.
*A61K 31/496* (2006.01)
*A61K 31/551* (2006.01)
*A61K 31/554* (2006.01)
*C07D 401/06* (2006.01)
*C07D 405/14* (2006.01)
*C07D 417/06* (2006.01)
*C07D 401/12* (2006.01)
*C07D 403/06* (2006.01)

(52) U.S. Cl. ............... 514/211.03; 514/218; 514/222.5; 514/253.01; 514/253.12; 540/489; 540/492; 544/3; 544/6; 544/230; 544/360; 544/363; 544/364; 544/372

(58) Field of Classification Search .............. None
See application file for complete search history.

(56) References Cited

U.S. PATENT DOCUMENTS 6,645,958 B2 * 11/2003 Weikert et al. ........... 514/211.03
2007/0249589 A1 10/2007 Aebi et al.

FOREIGN PATENT DOCUMENTS

| EP | 1627876 | 2/2006 |
|---|---|---|
| WO | WO 00/32590 | 6/2000 |
| WO | WO 2008/136754 | 11/2008 |

OTHER PUBLICATIONS

Vice et al., J. Org. Chem., 66, pp. 2487-2492 (2001).
Brown Ripin et al., Tetrahedron Letters, 41, pp. 5817-5819 (2000).
Mori, K., Tetrahedron, 39, pp. 3107-3109 (1983).
Avenoza et al., Synthesis, pp. 1146-1150 (1997).
Koshti et al., Tetrahedron Letters, 35, pp. 5157-5160 (1994).
Sugiyama et al., J. Am. Chem. Soc., 129, pp. 14811-14817 (2007).
Radosevich et al., J. Am. Chem. Soc, 127, pp. 1090-1091 (2005).

* cited by examiner

*Primary Examiner* — Emily Bernhardt
(74) *Attorney, Agent, or Firm* — George W. Johnston; Patricia S. Rocha-Tramaloni; Gene J. Yao

(57) ABSTRACT

The invention is concerned with novel heterocyclyl compounds of formula (I)

(I)

wherein A, X, $Y^1$, $Y^2$, $Y^3$, $R^3$, $R^4$, $R^5$, $R^6$, $R^7$, $R^8$, $R^9$, $R^{10}$, m, n and p are as defined in the description and in the claims, as well as physiologically acceptable salts thereof. These compounds are antagonists of CCR2 receptor, CCR5 receptor and/or CCR3 receptor and can be used as medicaments.

23 Claims, No Drawings

HETEROCYCLYL COMPOUNDS

PRIORITY TO RELATED APPLICATION(S)

This application claims the benefit of European Patent Application No. 08160534.7, filed Jul. 16, 2008, which is hereby incorporated by reference in its entirety.

BACKGROUND OF THE INVENTION

Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases. CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE−/− or LDL-R−/− backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

SUMMARY OF THE INVENTION

The invention is concerned the with novel heterocyclyl compounds of formula (I):

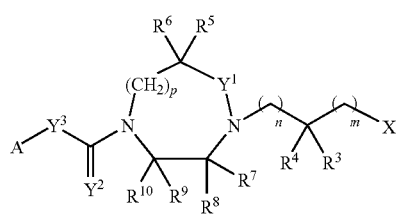

(I)

and pharmaceutically acceptable salts, prodrugs, or esters thereof, wherein A, X, $Y^1$—$Y^3$, $R^3$—$R^{10}$, n, m, and p are as defined in the detailed description and claims.

The compounds of formula (I) are CCR2 receptor (Chemokine Receptor 2/Monocyte chemotactic protein 1 receptor) antagonists and/or also CCR5 receptor (Chemokine Receptor 5) and/or CCR3 receptor (Chemokine Receptor 3) antagonists which may be usesful in the treatment of diseases or disorders associated with such receptors. Further, the invention is concerned with a process and an intermediate for the manufacture of the such compounds and pharmaceutical compositions which contain such compounds.

DETAILED DESCRIPTION OF THE INVENTION

Unless otherwise indicated, the following definitions are set forth to illustrate and define the meaning and scope of the various terms used to describe the invention herein.

The term "hydrogen" or "hydro" refers to the moiety of a hydrogen atom (—H) and not $H_2$.

The term "halogen" or "halo" refers to fluoro, chloro, bromo or iodo. Preferred "halogen" groups are fluoro or chloro.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. $C_{1-4}$ alkyl or $C_{1-3}$ alkyl is more preferred. The term "$C_{2-6}$ alkyl" means the same as a "$C_{1-6}$ alkyl", except that the $C_{2-6}$ alkyl has two to six carbon atoms; and the term "$C_{3-6}$ alkyl" means the same as a "$C_{1-6}$ alkyl", except that the $C_{3-6}$ alkyl has three to six carbon atoms; etc. The term "$C_{1-20}$ alkyl" means the same as a "$C_{1-6}$ alkyl", except that that the $C_{1-20}$ alkyl has one to 20 carbon atoms.

The term "hydroxy $C_{1-6}$ alkyl" means a $C_{1-6}$ alkyl substituted by one or more hydroxy group(s).

The term "halo $C_{1-6}$ alkyl" means a $C_{1-6}$ alkyl substituted by one or more of the same or different halogen atoms. Examples are 1-fluoromethyl, difluoromethyl, trifluoromethyl, 1-fluoroethyl, 2-fluoroethyl and 2,2,2-trifluoroethyl. The most preferred "halo $C_{1-6}$ alkyl" is trifluoromethyl.

The term "$C_{1-2}$ alkylene" means a linear saturated divalent hydrocarbon radical of one to two carbon atoms, such as methylene or ethylene.

The term "$C_{3-7}$ cycloalkyl", alone or in combination with other groups, means a saturated monovalent mono-cyclic hydrocarbon radical of three to seven ring carbons (e.g., cyclopropyl, cyclobutyl, or cyclohexyl).

The term "$C_{3-7}$ cycloalkyl $C_{1-6}$ alkyl" means a $C_{1-6}$ alkyl substituted by one or more $C_{3-7}$ cycloalkyl groups, as defined herein.

The term "$C_{7-10}$ bicycloalkyl", alone or in combination with other groups, means a saturated monovalent cyclic hydrocarbon radical of seven to ten ring carbons, having two rings, in which two or more ring carbon atoms of one ring are ring carbon atoms of the other ring, e.g., bicyclo[2.2.1]heptyl.

The term "$C_{1-6}$ alkoxy", alone or in combination with other groups, means the group R'—O—, wherein R' is a $C_{1-6}$ alkyl.

The term "$C_{1-6}$ alkoxy-carbonyl" refers to the group $R^{a1}$—C(O)—, wherein $R^{a1}$ is a $C_{1-6}$ alkoxy as defined above.

The term "$C_{1-6}$ alkoxy-$C_{1-6}$ alkyl" means a $C_{1-6}$ alkyl substituted by a $C_{1-6}$ alkoxy group, as defined herein The term "halo $C_{1-6}$ alkoxy" alone or in combination with other groups, means a $C_{1-6}$ alkoxy substituted by one or more halogens. In preferred embodiments the $C_{1-6}$ alkoxy is substituted by one to three halogens.

The term "$C_{1-6}$ alkylenedioxy" means —O—$C_{1-6}$ alkyl-O—. Methylenedioxy or 1,2-ethylenedioxy are preferred examples.

The term "$C_{3-6}$ alkenyl", alone or in combination with other groups, means a straight-chain or branched hydrocarbon residue comprising a carbon-carbon double bond, having three to six carbon atoms, provided that the carbon atom of the attachment point of the $C_{3-6}$ alkenyl to the rest of the molecule is not bonded to another carbon atom of the $C_{3-6}$ alkenyl by a carbon-carbon double bond. An example of a $C_{3-6}$ alkenyl is 2-propenyl.

The term "$C_{3-6}$-alkynyl", alone or in combination with other groups, means a straight-chain or branched hydrocarbon residue comprising a carbon-carbon triple bond, having three to six carbon atoms, provided that the carbon atom of the attachment point of the $C_{3-6}$ alkynyl to the rest of the molecule is not bonded to another carbon atom of the $C_{3-6}$ alkynyl by a carbon-carbon triple bond. An example of a $C_{3-6}$ alkynyl is 2-propynyl.

The term "acyl" means R—C(O)—, in which R is a $C_{1-6}$ alkyl, halo $C_{1-6}$ alkyl, $C_{3-7}$ cycloalkyl or $C_{3-7}$ cycloalkyl $C_{1-6}$ alkyl.

The term "heterocyclyl", alone or combination with other groups, means a non-aromatic mono- or bi-cyclic radical of four to nine ring atoms in which one to three ring atoms are heteroatoms independently selected from N, O and S(O)n (where n is an integer from 0 to 2), with the remaining ring atoms being C. The more preferred heterocyclyls are piperidyl or 6-aza-spiro[2,5]oct-6-yl.

The term "heterocyclyl-$C_{1-3}$alkyl" means a $C_{1-3}$ alkyl substituted by one heterocyclyl, as defined herein.

The term "aryl", alone or combination with other groups, means phenyl or naphthyl. The term "arylmethyl" means phenyl-$CH_2$— or a naphthyl-$CH_2$ radical.

The term "phenyl-$C_{1-3}$alkyl" means a $C_{1-3}$ alkyl, as defined herein, substituted by phenyl.

The term "arylcarbonyloxy-$C_{1-6}$ alkyl" refers to the group $R^{c1}$—C(O)—O—$R^{c2}$—, wherein $R^{c2}$ is a $C_{1-6}$ alkylene and $R^{c2}$ is an aryl, as defined above The term "heteroaryl", alone or combination with other groups, means an aromatic monocyclic or bicyclic radical of 5 to 10 ring atoms having one to three ring heteroatoms independently selected from N, O, and S, with the remaining ring atoms being C. More specifically the term "heteroaryl" includes, but is not limited to, pyridyl, furanyl, thienyl, thiazolyl, isothiazolyl, triazolyl, imidazolyl, isoxazolyl, pyrrolyl, pyrimidinyl, pyrazolyl, pyrazinyl, pyrimidinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. The most preferred heteroaryl are isoquinolyl, pyridyl, and quinolyl. The term "heteroarylmethyl" means a heteroaryl-$CH_2$-radical.

The term "heteroaryl-$C_{1-3}$alkyl" means a $C_{1-3}$ alkyl substituted by one heteroaryl, as defined herein.

The term "$C_{1-6}$ alkoxy-carbonyloxy" refers to the group $R^{a2}$—C(O)—O—, wherein $R^{a2}$ is a $C_{1-6}$ alkoxy as defined above.

The term "$C_{1-20}$alkylcarbonyloxy-$C_{1-6}$alkyl" refers to the group $R^{b1}$—C(O)—O—$R^{b2}$—, wherein $R^{b2}$ is a $C_{1-6}$ alkylene and $R^{b1}$ is a $C_{1-20}$ alkyl, as defined above.

The term "$C_{1-20}$alkoxycarbonyloxy-$C_{1-6}$alkyl" refers to the group $R^{a3}$—C(O)—O —$R^{b3}$—, wherein $R^{b3}$ is a $C_{1-6}$ alkylene and $R^3$ is a $C_{1-20}$ alkoxy, as defined above.

The term "bicyclic radicals" means radicals having two rings, in which two or more ring atoms of one ring are ring carbon atoms of the other ring.

The term, "$C_{1-6}$ alkylsulfonyl", "$C_{1-6}$ alkylsulfinyl" and "$C_{1-6}$ alkylthio" means a $C_{1-6}$ alkyl-$SO_2$—, $C_{1-6}$ alkyl-SO— and $C_{1-6}$ alkyl-S—, respectively.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

Unless otherwise indicated, in reference to a particular group or molecule, the term "substituted" refers to the fact that at least one of the hydrogen atoms of that group or molecule is replaced by some other substituent.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration.

Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt of any such compound).

Compounds that have the same molecular Formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

The invention is directed to a compound of formula (I):

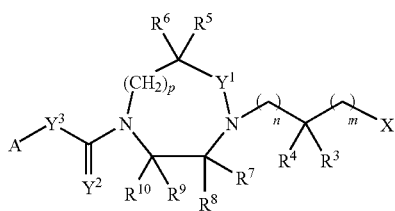

(I)

or a pharmaceutically acceptable salt, ester or prodrug thereof, wherein:

A is aryl, heteroaryl, arylmethyl or heteroarylmethyl; wherein said aryl, heteroaryl, aryl portion of said arylmethyl, or heteroaryl portion of said heteroarylmethyl is optionally substituted by one to three substituents independently selected from the group consisting of halogen, aryl, heteroaryl, $C_{1-6}$ alkyl, halo $C_{1-6}$ alkyl, $C_{1-6}$ alkoxy, halo $C_{1-6}$ alkoxy, and $C_{1-6}$ alkylenedioxy;

X is —N($R^1$)($R^2$);

$Y^1$ is C(O) or S(O)$_2$; $Y^2$ is O or S; and $Y^3$ is NH or O;

$R^1$ and $R^2$ are, independently selected from the group consisting of:
(1) hydrogen,
(2) $C_{1-6}$ alkyl,
(3) $C_{3-6}$ alkenyl,
(4) $C_{3-6}$ alkynyl,
(5) hydroxy $C_{2-6}$ alkyl,
(6) $C_{1-6}$ alkoxy $C_{2-6}$ alkyl,
(7) $C_{3-7}$ cycloalkyl, which is optionally substituted one to three times by $R^d$,
(8) $C_{3-7}$ cycloalkyl $C_{1-6}$ alkyl, wherein the $C_{3-7}$ cycloalkyl portion of said $C_{3-7}$ cycloalkyl $C_{1-6}$ alkyl is optionally substituted one to three times by $R^d$,
(9) $C_{7-10}$ bicycloalkyl,
(10) phenyl $C_{1-3}$ alkyl, wherein the phenyl portion of said phenyl $C_{1-3}$ alkyl is optionally substituted one to three times by $R^d$,
(11) heteroaryl $C_{1-3}$ alkyl, wherein the heteroaryl portion of said heteroaryl $C_{1-3}$ alkyl is optionally substituted one to three times by $R^d$,
(12) heterocyclyl, which is optionally substituted one to three times by $R^d$, and
(13) heterocyclyl $C_{1-6}$ alkyl; wherein the heterocyclyl portion of said heterocyclyl $C_{1-6}$ alkyl is optionally substituted one to three times by $R^d$; or alternatively,
$R^1$ and $R^2$, together with the nitrogen atom to which they are attached, form a heterocyclyl optionally substituted one to three times by $R^d$ and wherein one of the ring carbon atoms of said heterocyclyl is: (1) optionally replaced with a carbonyl group; and/or (2) a ring carbon atom of another ring which is a $C_{3-7}$ cycloalkyl or heterocyclyl, which is optionally substituted by a $C_{1-6}$ alkyl, and wherein one or two ring carbon atoms of said $C_{3-7}$ cycloalkyl or heterocyclyl is optionally replaced by a carbonyl group;

$R^3$ and $R^4$ are independently selected from the group consisting of:
(1) hydrogen,
(2) hydroxy,
(3) $C_{1-6}$ alkyl,
(4) $C_{1-6}$ alkoxy,
(5) $C_{3-7}$ cycloalkyl,
(6) $C_{3-7}$ cycloalkyl $C_{1-6}$ alkyl,
(7) $C_{1-6}$ alkoxycarbonyl,
(8) carboxyl,
(9) carbamoyl,
(10) mono- or di-$C_{1-6}$ alkyl substituted carbamoyl,
(11) $C_{1-6}$ alkoxycarbonyloxy,
(12) mono- or di-$C_{1-6}$ alkyl substituted aminocarbonyloxy,
(13) $C_{1-20}$ alkylcarbonyloxy-$C_{1-6}$ alkyl,
(14) $C_{1-20}$ alkoxycarbonyloxy-$C_{1-6}$ alkyl,
(15) arylcarbonyloxy-$C_{1-6}$ alkyl,
(16) mono- or di-$C_{1-6}$ alkyl substituted aminocarbonyloxy-$C_{1-6}$ alkyl,
(17) hydroxy-$C_{1-6}$ alkyl,
(18) $C_{1-6}$ alkoxy-$C_{1-6}$ alkyl,
(19) halogen or halo $C_{1-6}$ alkyl, and
(20) aryl substituted aminocarbonyloxy-$C_{1-6}$ alkyl, wherein said aryl substituent is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy; or alternatively,
$R^3$ and $R^4$, together with the carbon atom to which they are attached, form a $C_{3-7}$ cycloalkyl or heterocyclyl which is optionally substituted by one to three substituents independently selected from the group consisting of $C_{1-4}$ alkyl, halo $C_{1-4}$ alkyl and halogen;

$R^5$ and $R^6$ are independently hydrogen, $C_{1-6}$ alkyl or $C_{3-7}$ cycloalkyl, wherein said $C_{1-6}$ alkyl and $C_{3-7}$ cycloalkyl are optionally substituted by one to three substituents independently selected from the group consisting of (1) amino, (2) hydroxy, (3) carboxyl, (4) carbamoyl, (5) mono- or di-$C_{1-6}$ alkyl substituted carbamoyl, and (6) $C_{1-6}$ alkoxycarbonyl; or alternatively, $R^5$ and $R^6$, together with the carbon atom to which they are attached, form a $C_{3-7}$ cycloalkyl or heterocyclyl;

$R^7$, $R^8$, $R^9$ and $R^{10}$ are independently hydrogen, $C_{1-6}$ alkyl, $C_{3-7}$ cycloalkyl or aryl, wherein said $C_{1-6}$ alkyl is optionally substituted by one to three substituents independently selected from the group consisting of:
(1) hydroxy,
(2) $C_{1-6}$ alkoxy,
(3) carboxyl,
(4) carbamoyl,
(5) mono- or di-$C_{1-6}$ alkyl substituted carbamoyl,
(6) $C_{1-6}$ alkoxycarbonyl,
(7) aryl, which is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy; and
(8) heteroaryl, which is optionally substituted by one to three substituents independently selected from the group consisting of halogen, $C_{1-6}$ alkyl, halo $C_{1-6}$ alkyl, $C_{1-6}$ alkoxy and halo $C_1$, alkoxy;

$R^d$ is selected from the group consisting of:
(1) hydroxy,
(2) cyano,
(3) $NR^aR^b$,
(4) halogen,
(5) $C_{1-6}$ alkyl,
(6) halo $C_{1-6}$ alkyl,
(7) hydroxy $C_{1-6}$ alkyl,
(8) $C_{1-6}$ alkoxy,
(9) $C_{1-6}$ alkoxy $C_{1-6}$ alkyl,
(10) $C_{3-7}$ cycloalkyl,
(11) $C_{1-6}$ alkoxycarbonyl,
(12) acyl,
(13) —C(O)NR$^a$R$^b$,
(14) —NR$^a$—C(O)—R$^b$,
(15) —NR$^a$C(O)—OR$^b$,
(16) —NR$^a$—C(O)—NR$^b$,
(17) —NR$^a$—SO$_2$—R$^b$,
(18) —NR$^a$—SO$_2$—NR$^b$R$^c$,
(19) —OC(O)NR$^a$R$^b$,
(20) —OC(O)OR$^a$,
(21) $C_{1-6}$ alkylsulfonyl,
(22) $C_{1-6}$ alkylsulfinyl,
(23) $C_{1-6}$ alkylthio,
(24) phenyl or phenyl $C_{1-3}$ alkyl, wherein said phenyl or the phenyl portion of said phenyl $C_{1-3}$ alkyl is optionally substituted by one to three substituents independently selected from the group consisting of hydroxy, cyano, NR$^a$R$^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, $C_{1-6}$ alkylsulfonyl, $C_{1-6}$ alkylsulfinyl, and $C_{1-6}$ alkylthio,
(25) heteroaryl or heteroaryl $C_{1-3}$ alkyl, wherein said heteroaryl or the heteroaryl portion of said heteroaryl $C_{1-3}$ alkyl is optionally substituted by one to three substituents independently selected from the group consisting of hydroxy, cyano, NR$^a$R$^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)NR$^a$R$^b$, —NR$^a$—C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^c$R$^c$, —OC(O)NR$^a$R$^b$, —OC(O)OR$^a$, $C_{1-6}$ alkylsulfonyl, $C_{1-6}$ alkylsulfinyl, and $C_{1-6}$ alkylthio, and
(26) heterocyclyl, wherein one or two ring carbon atoms of said heterocyclyl is optionally replaced with a carbonyl group; and wherein said heterocyclyl is optionally substituted by one to three substituents independently selected from the group consisting of hydroxy, cyano, NR$^a$R$^b$, halogen, $C_{1-6}$ alkyl, halo $C_{1-6}$ alkyl, hydroxy $C_{1-6}$ alkyl, $C_{1-6}$ alkoxycarbonyl, acyl, —C(O)NR$^a$R$^b$, —NR$^a$C(O)—R$^b$, —NR$^a$—C(O)—OR$^b$, —NR$^a$—C(O)—NR$^b$, —NR$^a$—SO$_2$—R$^b$, —NR$^a$—SO$_2$—NR$^b$R$^c$, —OC(O)NR$^a$R$^b$, —OC(O)OR$^a$, $C_{1-6}$ alkylsulfonyl, $C_{1-6}$ alkylsulfinyl, and $C_{1-6}$ alkylthio;

$R^a$, $R^b$ and $R^c$ are independently hydrogen or $C_{1-6}$ alkyl;

n is an integer of 0 to 3; m is an integer of 0 to 3; and m+n is an integer of 1 to 5; and p is 0 or 1.

The compounds of formula (I) are CCR2 receptor antagonists, with some antagonist activity also at CCR3 and CCR5.

While the broadest definition of this invention is described before, certain compounds of formula (I) are preferred.

i) In the compounds of formula (I), A is phenyl or naphthyl, said phenyl and said naphthyl being optionally substituted by one to three substituents selected from the group consisting of halogen, halo $C_{1-6}$ alkyl, halo $C_{1-6}$ alkoxy and aryl. More preferably, A is phenyl substituted by one or two halogen atoms independently selected from the group consisting of chlorine and fluorine. A is especially 3-chlorophenyl or 3,4-dichlorophenyl.

ii) In the compounds of formula (I), X is preferably —N(R$^1$)(R$^2$) and R$^1$ and R$^2$, together with the nitrogen atom to which they are attached, form heterocyclyl optionally substituted by one to three substituents independently selected from the group consisting of hydroxy, $C_{1-6}$ alkyl and hydroxy $C_{1-6}$ alkyl; and/or one of the ring carbon atoms of the heterocyclyl formed by R$^1$ and R$^2$ may be a ring carbon atom of another ring which is $C_{3-7}$ cycloalkyl.

The heterocyclyl formed by R$^1$ and R$^2$, together with the nitrogen atom to which they are attached, is preferably piperidyl or pyrrolidinyl, and said piperidyl and pyrrolidinyl being optionally substituted by one or two substituents independently selected from the group consisting of hydroxy, $C_{1-6}$ alkyl and hydroxy $C_{1-6}$ alkyl, and/orone of the ring carbon atoms of said piperidyl and pyrrolidinyl formed by R$^1$ and R$^2$ may be shared by $C_{3-7}$ cycloalkyl ring or cycloheteroalkyl.

More preferably, in the compounds of formula (I), X is a mono spiro-heterocyclyl such as 6-aza-spiro[2,5]oct-6-yl, 5-azaspiro[2.5]oct-5-yl, 7-aza-spiro[3.5]non-7-yl, 8-aza-spiro[4.5]dec-8-yl, 1,8-diaza-spiro[4.5]dec-8-yl, 1,3,8-triaza-spiro[4.5]dec-8-yl, 2,8-diaza-spiro[4.5]dec-8-yl, 1-oxa-3,8-diaza-spiro[4.5]dec-8-yl, 1-oxa-8-aza-spiro[4.5]dec-8-yl, 2-oxa-8-aza-spiro[4.5]dec-8-yl, 2-oxa-7-aza-spiro[3.5]non-7-yl, 1-oxa-7-aza-spiro[3.5]non-7-yl, 9-aza-spiro[5.5]undec-9-yl, 1-oxa-4,9-diaza-spiro[5.5]undec-9-yl, wherein the spiro-heterocyclyl ring is optionally substituted by one to three substituents independently selected from the group consisting of hydroxy, oxo, alkoxy, fluorine or $C_{1-6}$ alkyl. Most preferably the spiro heterocyclyl is 6-aza-spiro [2,5]oct-6-yl wherein the spiro-heterocyclyl ring is optionally substituted by one to two substituents independently selected from the group consisting of hydroxy or $C_{1-6}$ alkyl In the compounds of formula (I), X is especially (3S,5S)-3-hydroxy-5-methyl-pyrrolidin-1-yl, piperidin-1-yl, (3S,4S)-3-hydroxy-4-methyl-pyrrolidin-1-yl or (S)-4-hydroxy-6-aza-spiro[2,5]oct-6-yl.

iii) In the compounds of formula (I), m+n is preferably an integer of 1 to 3, more preferably m+n is an integer of 1 or 2, most preferably m+n is 2.

iv) In the compounds of formula (I), one of $R^3$ and $R^4$ is preferably hydrogen and the other is hydrogen, hydroxy, $C_{1-6}$ alkyl, $C_{1-6}$ alkoxycarbonyl, di-$C_{1-6}$ alkyl substituted carbamoyl, $C_{1-6}$ alkoxycarbonyloxy, mono or di-$C_{1-6}$ alkyl substituted aminocarbonyloxy, hydroxy-$C_{1-6}$ alkyl, $C_{1-6}$ alkoxy-$C_{1-6}$ alkyl, $C_{1-20}$ alkylcarbonyloxy-$C_{1-6}$ alkyl, $C_{1-20}$ alkoxycarbonyloxy-$C_{1-6}$ alkyl, phenylcarbonyloxy-$C_{1-6}$ alkyl, mono or di-$C_{1-6}$ alkyl substituted aminocarbonyloxy-$C_{1-6}$ alkyl or phenyl substituted aminocarbonyloxy-$C_{1-6}$ alkyl, in which said phenyl are optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy. More preferably one of $R^3$ and $R^4$ is hydrogen and the other is hydrogen, hydroxy, hydroxy-$C_{1-6}$ alkyl, $C_{1-6}$ alkoxy-$C_{1-6}$ alkyl, $C_{1-6}$ alkylcarbonyloxy-$C_{1-6}$ alkyl or phenylcarbonyloxy-$C_{1-6}$ alkyl.

v) The compounds of formula (I), wherein n is 0, m is 2 and one of $R^3$ and $R^4$ is hydrogen, and the other is hydrogen, $C_{1-6}$ alkoxycarbonyl, hydroxy-$C_{1-6}$ alkyl, $C_{1-6}$ alkoxy-$C_{1-6}$ alkyl or mono or di-$C_{1-6}$ alkyl substituted carbamoyl, are preferred. More preferably, both $R^3$ and $R^4$ are hydrogen.

vi) In the compounds of formula (I), preferably, one or two of $R^5$, $R^6$, $R^7$, $R^8$, $R^9$ and $R^{10}$ are independently hydrogen, $C_{1-6}$ alkyl, phenyl or optionally trifluoromethyl substituted phenyl-$C_{1-6}$ alkyl and the others are hydrogen. More preferably, one of $R^5$ and $R^6$ is hydrogen or $C_{1-6}$ alkyl, the other is hydrogen, and $R^7$, $R^8$, $R^9$ and $R^{10}$ are hydrogen. Furthermore preferably, $R^5$ and $R^6$ is methyl, the other is hydrogen, and $R^7$, $R^8$, $R^9$ and $R^{10}$ are hydrogen.

vii) In the compounds of formula (I), $Y^1$ is preferably C(O).
viii) In the compounds of formula (I), $Y^2$ is preferably O.
ix) In the compounds of formula (I), $Y^3$ is preferably NH.
x) Preferred compounds of the invention are compounds of formula (I), such as:
4-[(S)-3-((S)-4-Hydroxy-6-aza-spiro[2.5]oct-6-yl)-1-hydroxymethyl-propyl]-5-oxo-[1,4]diazepane-1-carboxylic acid (3-chloro-phenyl)-amide,
(S)-2-Methyl-3-oxo-4-(3-piperidin-1-yl-propyl)-piperazine-1-carboxylic acid (3,4-dichloro-phenyl)-amide,
(S)-4-[3-((S)-4-Hydroxy-6-aza-spiro[2.5]oct-6-yl)-propyl]-2-methyl-3-oxo-piperazine-1-carboxylic acid (3,4-dichloro-phenyl)-amide,
(S)-4-[3-((3S,5S)-3-Hydroxy-5-methyl-piperidin-1-yl)-propyl]-2-methyl-3-oxo-piperazine-1-carboxylic acid (3,4-dichloro-phenyl)-amide,
(S)-4-[3-((3S,4S)-3-Hydroxy-4-methyl-piperidin-1-yl)-propyl]-2-methyl-3-oxo-piperazine-1-carboxylic acid (3,4-dichloro-phenyl)-amide,
(R)-4-[(S)-3-((S)-4-Hydroxy-6-aza-spiro[2.5]oct-6-yl)-1-methoxymethyl-propyl]-2-methyl-5-oxo-[1,4]diazepane-1-carboxylic acid (3-chloro-phenyl)-amide,
(S)-4-[(S)-3-((S)-4-Hydroxy-6-aza-spiro[2.5]oct-6-yl)-1-methoxymethyl-propyl]-2-methyl-3-oxo-piperazine-1-carboxylic acid (3,4-dichloro-phenyl)-amide,
(S)-4-[(S)-3-((S)-4-Hydroxy-6-aza-spiro [2.5]oct-6-yl)-1-methoxymethyl-propyl]-2-methyl-3-oxo-piperazine-1-carboxylic acid (3-chloro-phenyl)-amide,
(S)-4-[4-((S)-4-Hydroxy-6-aza-spiro[2.5]oct-6-yl)-butyl]-2-methyl-3-oxo-piperazine-1-carboxylic acid (3-chloro-phenyl)-amide,
(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3,4-dichloro-phenyl)-amide,
(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3-chloro-phenyl)-amide,
Acetic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester,
Acetic acid (S)-2-[(S)-4-(3-chloro-phenylcarbamoyl)-3-methyl-2-oxo-piperazin-1-yl]-4-((S)-4-hydroxy-6-aza-spiro[2.5]oct-6-yl)-butyl ester,
2,2-Dimethyl-propionic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester,
Benzoic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester, or
(S)-4-[(S)-4-((S)-4-Hydroxy-6-aza-spiro[2.5]oct-6-yl)-1-hydroxymethyl-butyl]-2-methyl-3-oxo-piperazine-1-carboxylic acid (3,4-dichloro-phenyl)-amide.

General Synthetic Procedures

Compounds of formula (I) can be produced as outlined in scheme 1. $PG^1$ is a suitable protective group such as tert-butoxycarbonyl or benzyloxycarbonyl, LG is a leaving group such as chlorine, bromine, iodine, or methanesulfonyloxy, Z is either chlorine or phenoxy.

In step a, scheme 1, protected starting material 1 is reacted with alkylating agent 2 in the presence of a base, e.g., sodium hydride or potassium tert-butylate, in a solvent such as N,N-dimethylformamide, N,N-dimethylacetamide or tetrahydrofuran, at temperatures between 0° C. and 100° C., thus leading to 3.

In step b, scheme 1, the protective group of 3 is removed using methods known in the art, leading to secondary amine 4. In the case where $PG^1$ is tert-butoxycarbonyl, suitable deprotection reagents and conditions are strong acids such as hydrogen chloride or trifluoroacetic acid in a solvent such as 1,4-dioxane or dichloromethane, at or below room temperature. In the case where $PG^1$ is benzyloxycarbonyl, the protective group is removed by hydrogenation at pressures between 1 and 100 bar, at temperatures between 0° C. and 100° C., in solvents such as methanol, ethanol, or ethyl acetate.

In step c, scheme 1, secondary amine 4 is converted to compound of general formula (I) through reaction with isocyanate or isothiocyanate 5A, or with chloroformate, chlorothionoformate or phenyl carbamate 5B, or with 3-methyl-1H-imidazolium derivative 5C using methods well known to someone skilled in the art. The reaction is typically carried out in aprotic solvents such as dichloromethane, tetrahydrofuran, N,N-dimethylformamide, N-methylpyrrolidinone, dimethyl sulfoxide, acetonitrile and mixtures thereof at temperatures between 0° C. and 120° C. in the presence or absence of a base such as triethylamine, diisopropylethylamine, 4-methylmorpholine, and/or 4-(dimethylamino)pyridine. Isocyanates 5A, isothiocyanates 5A, chloroformates ($Y^3$=O, Z=Cl) or phenyl carbamates ($Y^3$=NH, Z=OPh) 5B, and chlorothionoformates 5B ($Y^3$=S, Z=Cl) are commercially available or can be synthesized by methods known in the art. For instance, isocyanates 5A can be synthesized from the corresponding arylamines by reaction with a slight excess of phosgene or 0.6 equivalents of diphosgene in a solvent like tetrahydrofuran at temperatures between 0° C. and 70° C. Chloroformates 5B can be produced from phenols by reaction with phosgene, diphosgene or his-(trichloromethyl)-carbonate in the presence of base like pyridine or lutidine in solvents like dichloromethane or acetonitrile, and chlorothionoformates 5B are prepared analogously from phenols by reaction with thiophosgene. Phenyl carbamates 5B can be prepared from the corresponding arylamines by reaction with phenyl chloroformate, in a solvent such as tetrahydrofuran, at temperatures between −20° C. and 20° C. Imidazolium reagents 5C are generated by N(3)-methylation (e.g., with dimethyl sulfate in a solvent like acetonitrile, at about 80° C.) of imidazole-1-carboxylic acid aryl esters, which are synthesized from phenols and 1,1'-carbonyldiimidazole, as described in the experimental part.

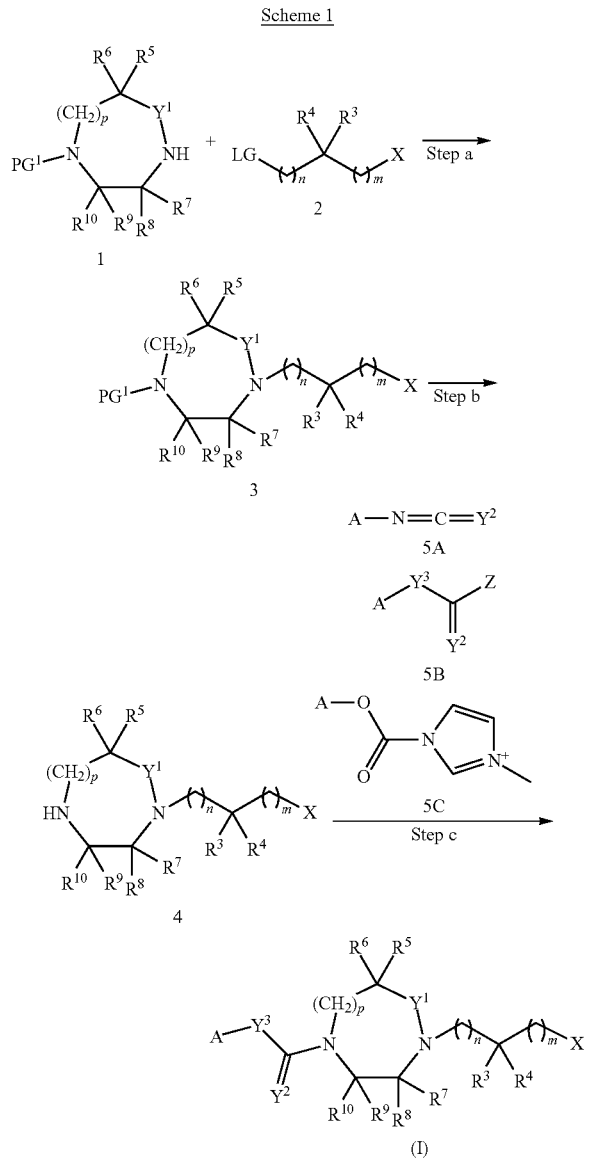

Scheme 1

In Scheme 1, A, X, $Y^1$, $Y^2$, $Y^3$; $R^3$, $R^4$, $R^5$, $R^6$, $R^7$, $R^8$, $R^9$, $R^{10}$, m, n and p are as defined before. Z is chlorine or phenoxy.

Substituents $R^3$ and/or $R^4$ in (I) or in any synthetic intermediate can be interconverted using reagents and methods known in the art. For instance, esters ($R^3$ and/or $R^4$=$C_{1-6}$ alkoxycarbonyl) can be reduced to the corresponding alcohols ($R^3$ and/or $R^4$=hydroxymethyl), e.g., with lithium borohydride in ethanol. These alcohols can further be transformed to ethers ($R^3$ and/or $R^4$=$CH_2OC_{1-6}$ alkyl), e.g., with an alkyl halide in solvents such as tetrahydrofuran, N,N-dimethylformamide or N,N-dimethylacetamide with sodium hydride as base, or with an alkyl halide in the presence of silver(I) oxide. Similarly, esters ($R^3$ and/or $R^4$=$C_{1-6}$ alkoxycarbonyl) can be hydrolyzed to the corresponding carboxylic acids, ($R^3$ and/or $R^4$=COOH), e.g., through base-mediated hydrolysis using bases such as lithium hydroxide or sodium hydroxide in solvents such as water, methanol, tetrahydrofuran, or mixtures thereof. These acids can then be elaborated to the corresponding amides ($R^3$ and/or $R^4$=mono- or di-$C_{1-6}$ alkyl substituted aminocarbonyloxy), as described in scheme 4, step b.

Intermediate 3 can also be synthesized as described in scheme 2. $PG^1$ is a suitable protective group such as tert-butoxycarbonyl or benzyloxycarbonyl, $PG^2$ is a protective group, e.g., benzyl, tetrahydropyran-2-yl, tert-butyldimethylsilyl or tert-butyldiphenylsilyl, LG is a leaving group such as chlorine, bromine, iodine, or methanesulfonyloxy.

In step a, scheme 2, protected heterocycle 1 is reacted with alkylating agent 6, leading to 7. The reaction is performed in analogy with scheme 1, step a.

In step b, scheme 2, the protective group of the hydroxyl of 7, $PG^2$, is removed, using methods and reagents known in the art, leading to 8. In the case where $PG^2$ is benzyl, the protective group is removed, e.g., by hydrogenation at pressures between 1 bar and 100 bar, in the presence of a suitable catalyst, e.g., palladium on activated charcoal, in solvents such as methanol, ethanol, ethyl acetate, acetic acid, or mixtures thereof, at temperatures between 20° C. and 150° C. In the case where $PG^2$ is benzyl and $PG^1$ is benzyloxycabonyl, the benzyl protective group is preferably removed by reaction with boron trichloride in a solvent such as dichloromethane, at temperatures between −20° C. and 40° C. In the case where $PG^2$ is tetrahydropyran-2-yl, the protective group is removed under acidic conditions, e.g., with toluene-4-sulfonic acid, pyridinium toluene-4-sulfonate, or hydrochloric acid, in solvents such as methanol, ethanol, water, or mixtures thereof, at temperatures between 20° C. and 100° C. In the case where $PG^2$ is a silyl group, e.g., tert-butyldimethylsilyl or tert-butyldiphenylsilyl, the protective group is removed with a fluoride reagent, e.g., tetrabutylammonium fluoride, in a solvent such as tetrahydrofuran, at temperatures between 0° C. and 50° C. In the case where $PG^2$ is a silyl group, e.g., tert-butyldimethylsilyl or tert-butyldiphenylsilyl, and $R^3$ and/or $R^4$ is $C_{1-6}$ alkoxycarbonyl, the protective group is preferably removed by reaction with boron trichloride in a solvent such as dichloromethane, at temperatures between −20° C. and 40° C.

In step c, scheme 2, alcohol 8 is oxidized to aldehyde 9 using reagents and method known in the art. For instance, the oxidation is carried out with sodium hypochlorite, in a two-phase mixture of water and dichloromethane, in the presence of sodium hydrogencarbonate and catalytic amounts of sodium bromide or potassium bromide and 2,2,6,6-tetramethylpiperidin-1-oxyl radical, at temperatures between 0° C. and 25° C. Alternatively, the oxidation can be performed with trichloroisocyanuric acid in the presence of catalytic amounts of 2,2,6,6-tetramethylpiperidin-1-oxyl radical, in a solvent such as dichloromethane, at temperatures between 0° C. and 40° C. Alternatively, the oxidation may be performed with catalytic amounts of tetrapropylammonium perruthenate in the presence of stoichoimetric amounts of a co-oxidant such as 4-methylmorpholine-4-oxide and molecular sieves, at temperatures between 0° C. and 40° C., in solvents such as dichloromethane, acetonitrile or mixtures thereof. Alternatively, dimethyl sulfoxide-based reagents can be employed, such as dimethyl sulfoxide-oxalyl chloride, or dimethyl sulfoxide-trifluoroacetic anhydride, in the presence of an organic base such as triethylamine in a solvent such as dichloromethane, at temperatures below 0° C., typically between −78° C. and −60° C. Alternatively, pyridine-sulfur trioxide can be employed in dimethyl sulfoxide or dimethylsulfoxide-dichloromethane solvent mixture in the presence of an organic base such as triethylamine, at temperatures between 0° C. and 25° C.

In step d, scheme 2, aldehyde 9 is transformed into 3 by reaction with amine $HN(R^1)(R^2)$, using methods well known in the art, e.g., reductive amination. The reaction is carried out using a suitable reducing agent, e.g., sodium borohydride, sodium triacetoxyborohydride, sodium cyanoborohydride, or borane pyridine complex, in solvents such as methanol, ethanol, acetic acid, 1,2-dichloroethane, or mixtures thereof, optionally in the presence of a dehydrating agent such as magnesium sulfate, at temperatures between 0° C. and 80° C.

Amines of formula $HN(R^1)(R^2)$ are either commercially available or can be synthesized as described in the experimental section.

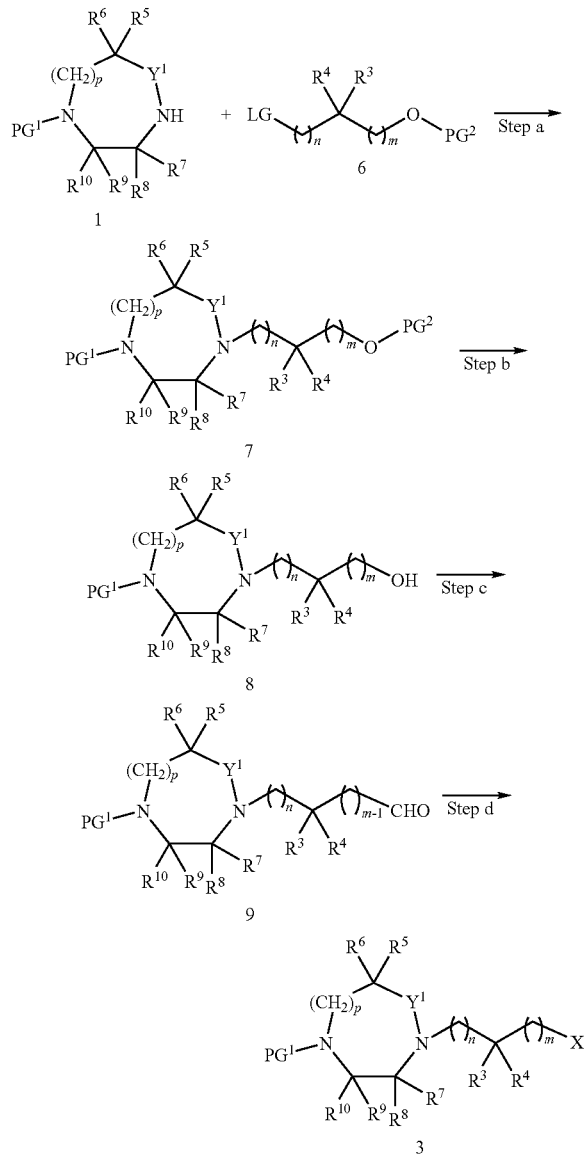

In Scheme 2, X, $Y^1$; $R^3$, $R^4$, $R^5$, $R^6$, $R^7$, $R^8$, $R^9$, $R^{10}$, m, n and p are as defined before.

Intermediate 7 in which $R^6$ and $R^8$ are H, p is 1 and $Y^1$ is C(O) is represented by the general formula 7A.

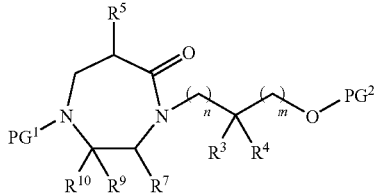

$R^3$, $R^4$, $R^5$, $R^7$, $R^9$, $R^{10}$, m and n are as defined before.

Intermediate 7A can be also synthesized as described in scheme 3. $R^e$ is tert-butyl, benzyl, or lower alkyl, e.g., methyl or ethyl, $PG^1$ is a suitable protective group such as tert-butoxycarbonyl or benzyloxycarbonyl, $PG^2$ is a protective group, e.g., benzyl, tetrahydropyran-2-yl, tert-butyldimethylsilyl or tert-butyldiphenylsilyl.

In step a, scheme 3, aminoalcohol 10A is reacted with acrylate 11, either neat or in a solvent such as methanol, at temperatures between 0° C. and 60° C. The secondary amine intermediate is then protected with a suitable protective group, using reagents and methods known in the art, thus leading to 12. In the case where $PG^1$ is tert-butoxycarbonyl, the reaction is carried out, e.g., with di-tert-butyl dicarbonate, in a solvent such as dichloromethane or N,N-dimethylformamide, optionally in the presence of a base, e.g., triethylarmine. In the case where $PG^1$ is benzyloxycarbonyl, the reaction is performed, e.g., with N-(benzyloxycarbonyloxy)succinimide or with benzyl chloroformate, in solvents such as water, acetone, tetrahydrofuran, or mixtures thereof, in the presence of a base, e.g., triethylamine or sodium hydrogencarbonate.

Aminoalcohols of formula 10A are either commercially available or can be synthesized as described in the experimental section.

In step b, scheme 3, alcohol 12 is oxidized to aldehyde or ketone 13, in analogy with scheme 2, step c.

In step c, scheme 3, aldehyde or ketone 13 is transformed into 15 by reaction with amine 14, using methods well known in the art, e.g., reductive amination. The reaction is carried out using a suitable reducing agent, e.g., sodium borohydride, sodium triacetoxyborohydride, sodium cyanoborohydride, or borane pyridine complex, in solvents such as methanol, ethanol, acetic acid, 1,2-dichloroethane, or mixtures thereof, at temperatures between 0° C. and 80° C.

Amines of formula 14 are either commercially available or can be synthesized as described in the experimental section.

In step d, scheme 3, ester 15 is deprotected to give acid 16. In the case where $R^e$ is tert-butyl, the deprotection is performed, e.g., with hydrogen chloride, in solvents such as 1,4-dioxane, water, or mixtures thereof, at temperatures between 0° C. and 20° C. In the case where $R^e$ is benzyl, the deprotection is performed, e.g., by hydrogenation at pressures between 1 bar and 10 bar, in solvents such as methanol, ethanol, tetrahydrofuran, ethyl acetate, or mixtures thereof, in the presence of a suitable catalyst, e.g., palladium on activated charcoal. In the case where $R^e$ is lower alkyl, the deprotection is performed, e.g., by base-mediated hydrolysis in solvents such as water, methanol, tetrahydrofuran and mixtures thereof at temperatures between −20° C. and 120° C. Typical reagents are aqueous or lithium hydroxide, sodium hydroxide, potassium hydroxide, sodium hydrogen carbonate, sodium carbonate, potassium hydrogencarbonate and potassium carbonate.

In step e, scheme 3, amino acid 16 is cyclized to 7A using methods well known to someone skilled in the art, e.g., amide formation using a coupling reagent. The reaction is typically carried out in aprotic solvents such as dichloromethane, tetrahydrofuran, N,N-dimethylformamide, N-methylpyrrolidinone and mixtures thereof in the presence or absence of a base such as triethylamine, diisopropylethylamine, 4-methylmorpholine, and/or 4-(dimethylamino)pyridine, at temperatures between −30° C. and 60° C. Typically used coupling agents are N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate or O-(7-azabenzotriazol-1-yl)-N,N,N',N'-tetramethyluronium hexafluoro-phosphate.

Substituents $R^6$ can be introduced in the ring system of 7A via deprotonation of the proton at C(6) of the [1,4]diazepan-5-one ring under suitable conditions (e.g., lithium hexamethyldisilazide or lithium diisopropyl amide in a solvent like tetrahydrofuran at temperatures between −78° C. to 0° C.), followed by selective alkylation with an electrophile of the general formula $R^6$-LG, in which LG is a leaving group such as bromine, iodine, or trifluoromethanesulfonyloxy.

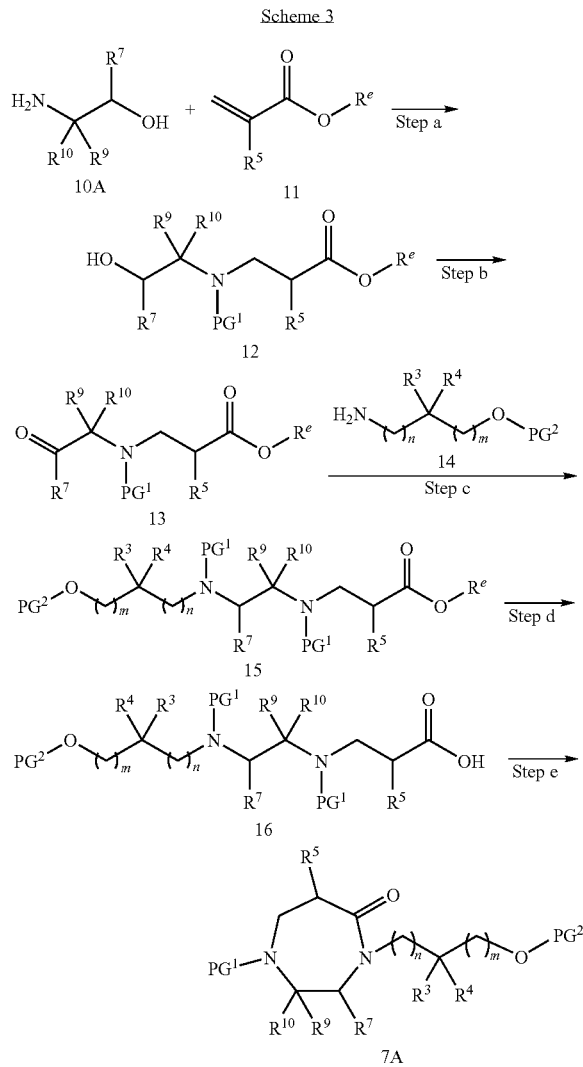

In Scheme 3, $R^3$, $R^4$, $R^5$, $R^7$, $R^9$, $R^{10}$, m and n are as defined before. $R^e$ is tert-butyl, benzyl, or lower alkyl, e.g., methyl or ethyl.

Intermediate 8 in which $R^{10}$ is H, p is 0 and $Y^1$ is C(O) is represented by the general formula 8A.

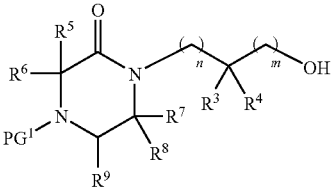

$R^3$, $R^4$, $R^5$, $R^6$, $R^7$, $R^8$, $R^9$, m and n are as defined before.

Intermediate 8A can be also synthesized as described in scheme 4. $PG^1$ and $PG^3$ are a suitable protective groups such as tert-butoxycarbonyl or benzyloxycarbonyl, $PG^2$ is a protective group, e.g., benzyl, tert-butyldimethylsilyl, tert-butyldiphenylsilyl, or tetrahydropyran-2-yl, LG is a leaving group, e.g., chlorine or bromine.

In step a, scheme 4, aminoalcohol 10B is reacted with halide 6 nucleophilic substitution, leading to secondary amine 18, using methods known in the art. For instance, the reaction is carried out in a solvent such as methanol, ethanol, or acetonitrile, at temperatures between 20° C. and the boiling point of the solvent, optionally in the presence of a base, e.g., potassium hydrogencarbonate, potassium carbonate, optionally in the presence of sodium iodide.

Aminoalcohols of formula 10B are either commercially available or can be synthesized as described in the experimental section.

In step b, scheme 4, secondary amine 18 is converted to amide of general formula 20 through reaction with N-protected amino acid 19, using methods well known to someone skilled in the art. For instance, the reaction is typically carried out in aprotic solvents such as dichloromethane, tetrahydrofuran, N,N-dimethylformamide, N-methylpyrrolidinone and mixtures thereof at temperatures between 0° C. and 80° C. in the presence or absence of a base such as triethylamine, diisopropylethylamine, 4-methylmorpholine, and/or 4-(dimethylamino)pyridine, and in the presence of a coupling agent such as N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate.

Alternatively, this reaction can be performed in two steps involving first formation of the acyl halide derivative of 19 and subsequent coupling reaction with amine 18 in the presence of a base. Typically employed reagents for the formation of the acyl chloride are thionyl chloride, phosphorous pentachloride, oxalyl chloride or cyanuric chloride, and the reaction is generally conducted in the absence of a solvent or in the presence of an aprotic solvent like dichloromethane, toluene or acetone. A base can optionally be added, like for example pyridine, triethylamine, diisopropylethylamine or 4-methylmorpholine, and catalytic amounts of N,N-dimethylformamide may be used. The obtained acyl chloride can be isolated or reacted as such with amine 18 in an aprotic solvent, like dichloromethane, tetrahydrofuran or acetone, in the presence of a base. Typical bases are triethylamine, 4-methylmorpholine, pyridine, diisopropylethylamine or 4-(dimethylamino)pyridine or mixtures thereof.

Alternatively, such reactions can be performed in two steps involving first formation of a mixed anhydride derivative of 19 obtained by reaction with a reagent such as ethyl chloroformate, isobutyl chloroformate, or acetic anhydride, in a solvent such as dichloromethane or tetrahydrofuran, at temperatures between −30° C. and 20° C., and subsequent reaction with amine 18 as described above.

In step c, scheme 4, oxidation of the hydroxyl of 20 leads to hemiaminal intermediate 21. This reaction is performed in analogy with scheme 2, step c.

In step d, scheme 4, removal of the amine protective group of 21, PG³, and reduction leads to piperazinone 22. In the case where PG³ is tert-butoxycarbonyl, this conversion is accomplished concomitantly by reaction with a suitable reducing agent, e.g., triethylsilane or sodium borohydride, in the presence of trifluoroacetic acid, in a solvent such as dichloromethane or tetrahydrofuran, at about 0° C. In the case where PG³ is benzyloxycarbonyl, reaction of 21 with an acid, e.g., trifluoroacetic acid or methanesulfonic acid, in solvents such as dichloromethane, 1,4-dioxane, dichloromethane, water, or mixtures thereof leads to the elimination of water. The resultant 3,4-dihydro-1H-pyrazin-2-one intermediate is subjected to catalytic hydrogenation at pressures between 1 bar and 10 bar, using a suitable catalyst, e.g., palladium on activated charcoal, in solvents such as methanol, ethanol, ethyl acetate, or mixtures thereof, at temperatures between 0° C. and 50° C., leading to 22.

In step e, scheme 4, the protective group of the hydroxyl of 22, PG², is removed to produce 23A. This deprotection is performed in analogy with scheme 2, step b.

In step f, scheme 4, protection of the amino group of piperazinone 23A affords 8A. In the case where PG¹ is tert-butoxycarbonyl, the reaction is carried out, e.g., with di-tert-butyl dicarbonate, in a solvent such as dichloromethane or N,N-dimethylformamide, optionally in the presence of a base, e.g., triethylamine. In the case where PG¹ is benzyloxycarbonyl, the reaction is performed, e.g., with N-(benzyloxycarbonyloxy)succinimide or with benzyl chloroformate, in solvents such as water, acetone, tetrahydrofuran, or mixtures thereof, in the presence of a base, e.g., triethylamine or sodium hydrogencarbonate.

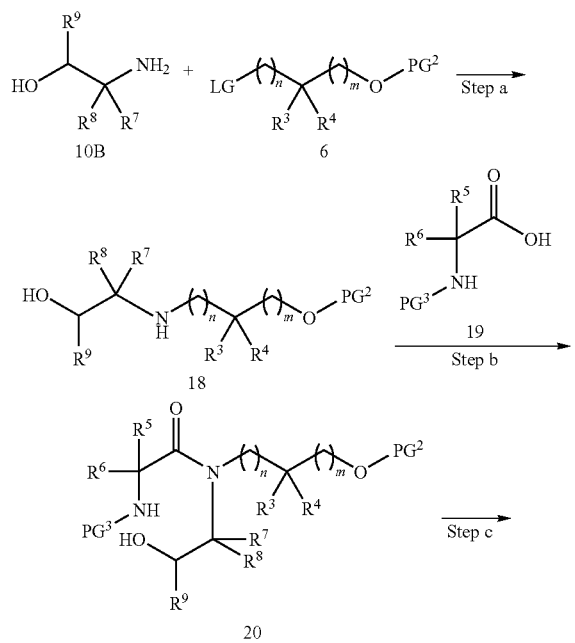

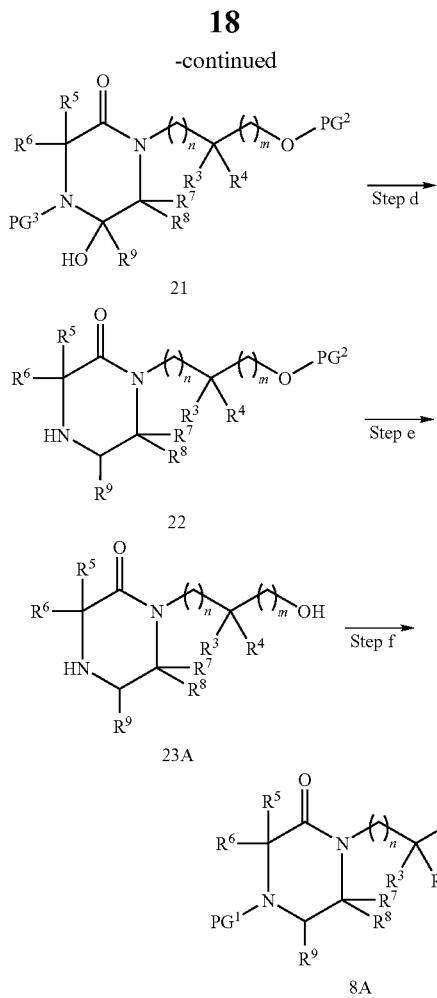

In Scheme 4, $R^3$, $R^4$, $R^5$, $R^6$, $R^7$, $R^8$, $R^9$, m and n are as defined before.

Intermediate 23A in which $R^8$ is H is represented by the general formula 23AA.

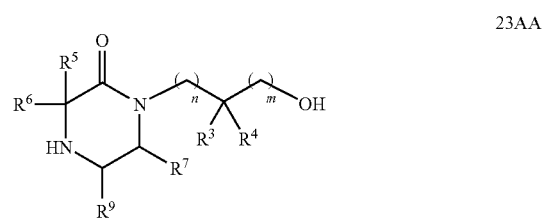

$R^3$, $R^4$, $R^5$, $R^6$, $R^7$, $R^9$, m and n are as defined before.

Intermediate 23AA can be also synthesized as described in scheme 5. $R^e$ is lower alkyl, e.g., methyl or ethyl, PG² is a protective group, e.g., benzyl, tert-butyldimethylsilyl, tert-butyldiphenylsilyl, or tetrahydropyran-2-yl, PG³ is a suitable protective group such as tert-butoxycarbonyl or benzyloxycarbonyl, LG is a leaving group, e.g., chlorine or bromine.

In step a, scheme 5, primary amine 14 is converted to secondary amine 25 by reductive amination reaction with carbonyl derivative 24A or by nucleophilic substitution reaction with halide 24B. The reductive amination reaction with 24A is performed in analogy with scheme 2, step d. The nucleophilic substitution reaction with 24B is performed in analogy with scheme 4, step a.

In step b, scheme 5, N-protected amino acid 19 is coupled with amine 25 in analogy with scheme 4, step b, leading to 26. In the case where the presence of a hydroxy group in $R^3$ or $R^4$ (e.g., $R^3$ or $R^4$=hydroxy or hydroxymethyl) may interfere with the amide coupling reaction, the hydroxyl of 14 may be temporarily protected as the trimethylsilyl ether by reaction with chlorotrimethylsilane, in the presence of a base, e.g., triethylamine of N-methylmorpholine.

In step c, scheme 5, cleavage of the acetal, removal of the amine protective group, $PG^3$, and reductive cyclization of 26 leads to piperazinone 23AA. This conversion is performed using the same reagents and conditions as described in scheme 4, step d.

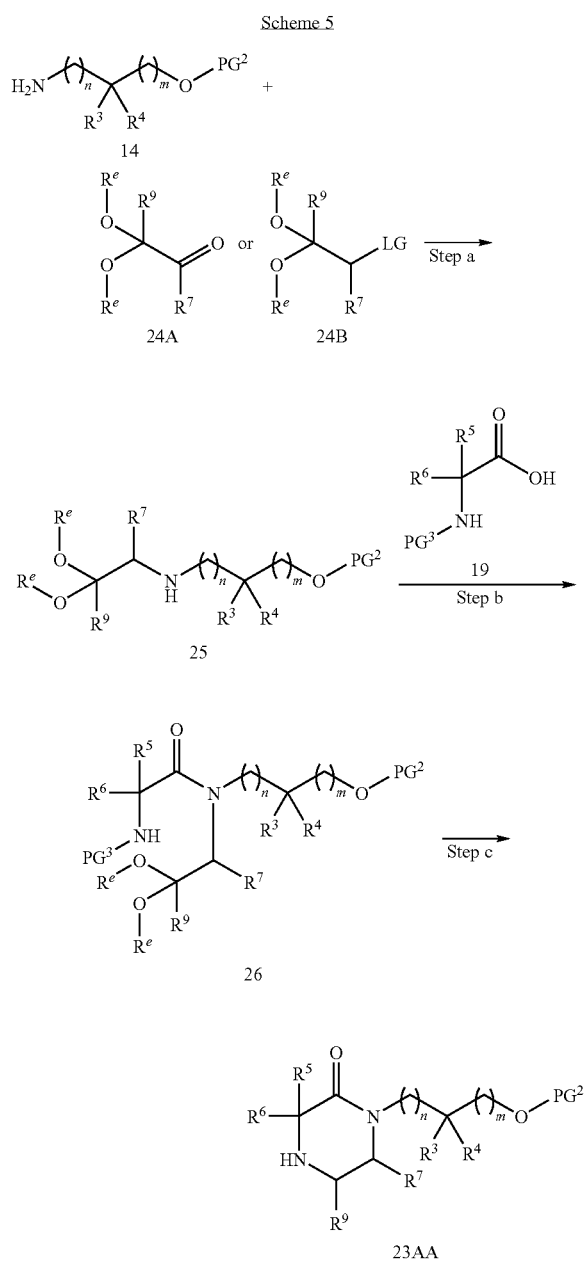

In Scheme 5, $R^3$, $R^4$, $R^5$, $R^6$, $R^7$, $R^9$, m and n are as defined before. $R^e$ is lower alkyl, e.g., methyl or ethyl.

Intermediate 8A in which $R^8$ is H is represented by the general formula 8AA.

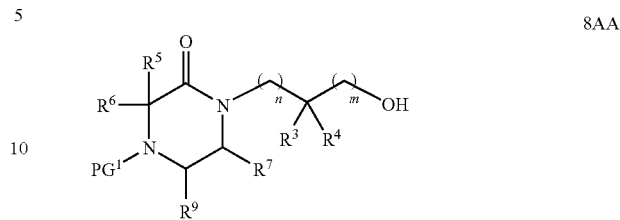

Intermediate 8AA can be also synthesized as described in scheme 6. $R^a$ and $R^e$ are lower alkyl, e.g., methyl or ethyl, $PG^1$ is a suitable protective group such as tert-butoxycarbonyl or benzyloxycarbonyl, LG is a leaving group, e.g., chlorine or bromine.

In step a, scheme 6, amino acid ester 27 is converted to secondary amine 29 by reaction with aldehyde 28A or halide 28B, in analogy with scheme 5, step a.

In step b, scheme 6, protection of the amino group in 29 leads to carbamate 30. This conversion is performed in analogy with scheme 4, step f.

In step c, scheme 6, the acetal group of 30 is cleaved, giving rise to the carbonyl compound 31. This reaction is preferably performed by transacetalization using a suitable ketone as solvent, e.g., acetone or 2-butanone, in the presence of a suitable catalyst, e.g., Amberlyst® 15 or pyridinium toluene 4-sulfonate, optionally in the presence of water, at temperatures between 0° C. and the boiling point of the solvent. Alternatively, the reaction is carried out in the presence of aqueous acid solutions, e.g., formic acid or hydrochloric acid, at temperatures between 0° C. and 20° C.

In step d, scheme 6, aldehyde or ketone 31 is converted to piperazinone 8AA by a reductive amination reaction with amino alcohol 32 to an amino ester intermediate, followed by cyclization. The reductive amination is performed in analogy to scheme 2, step d. The subsequent cyclization of the amino ester often takes place spontaneously. In cases where the amino ester intermediate does not cyclize spontaneously (most likely when n=0 or 1 and $R^3$ and/or $R^4{\neq}H$), the cyclization may be enabled, e.g., using a base such as potassium carbonate, in a solvent such as methanol or ethanol, as described in the experimental section.

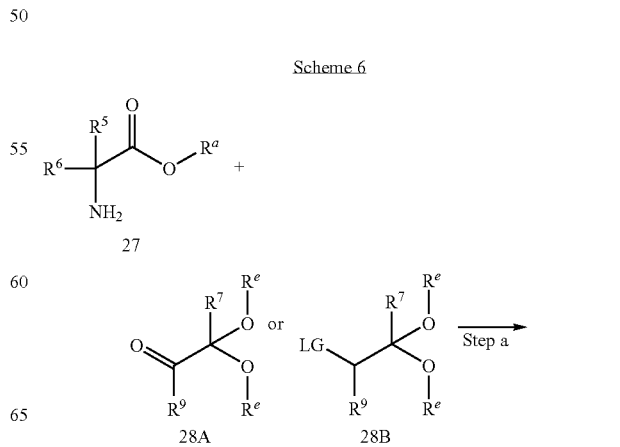

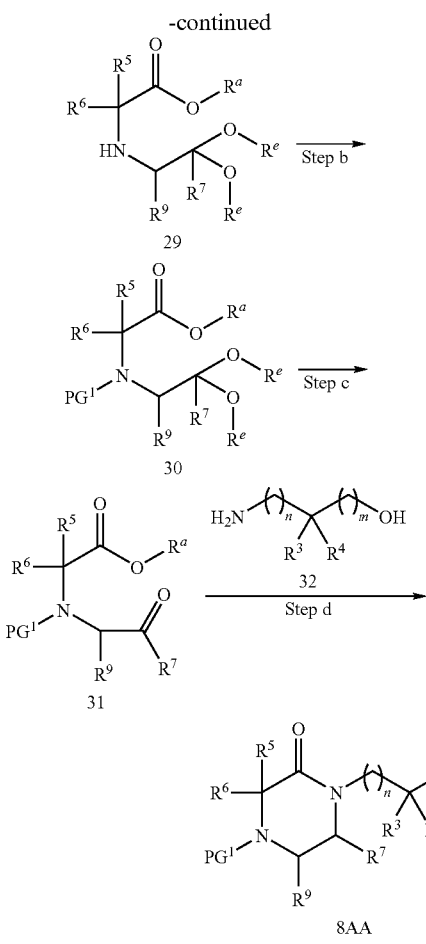

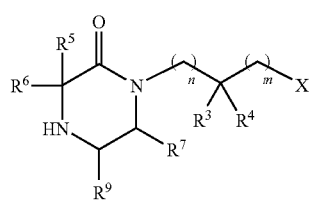

In Scheme 6, $R^3$, $R^4$, $R^5$, $R^6$, $R^7$, $R^9$, m and n are as defined before. $R^a$ and $R^e$ are lower alkyl, e.g., methyl or ethyl.

Intermediate 4 in which $R^8$ and $R^{10}$ is H, p is 0 and $Y^1$ is C(O) is represented by the general formula 4A.

4A

X, $R^3$, $R^4$, $R^5$, $R^6$, $R^7$, $R^9$, m and n are as defined before.

Intermediate 4A can be also synthesized as described in scheme 7. $PG^3$ and $PG^4$ are suitable protective groups such as tert-butoxycarbonyl or benzyloxycarbonyl, LG is a leaving group, e.g., chlorine or bromine, $R^e$ is lower alkyl, e.g., methyl or ethyl.

In step a, scheme 7, alcohol 33A is oxidized to aldehyde 34, in analogy with scheme 2, step c. Alternatively, aldehyde 34 is obtained from alkene 33B using methods and reagents known in the art, e.g., 33B is reacted with sodium periodate in the presence of catalytic amounts of a suitable osmium source such as osmium(VIII) oxide or potassium osmate(VI) dihydrate, in solvents such as acetone, tert-butylalcohol, water, or mixtures thereof, at temperatures between 0° C. and 30° C.

In cases where $R^3$ or $R^4$ in 33A are $CH_2OH$, this hydroxy group and the carbamate N—H are protected through conversion to a 2,2-dimethyl-oxazolidine derivative, as described in the experimental section.

Alcohols of formula 33A and alkenes of formula 33B are either commercially available or can be synthesized as described in the experimental section.

In step b, scheme 7, aldehyde 34 is reacted with amine of the general formula $HN(R^1)(R^2)$, in analogy with scheme 2, step d, leading to 35.

In cases where the carbamate N—H and the hydroxy group of $R^3$ or $R^4$ have been previously protected as the 2,2-dimethyl-oxazolidine derivative, this heterocycle is cleaved by reaction with a suitable acid catalyst, e.g., Amberlite® IR-120, in solvents such as methanol or ethanol, in the presence of water, at room temperature.

In step c, scheme 7, the protective group of 35 is removed in analogy with scheme 1, step b, leading to 36.

In step d, scheme 7, primary amine 36 is converted to secondary amine 37 by reaction with 24A or 24B, in analogy with scheme 5, step a.

In step e, scheme 7, N-protected amino acid 19 is coupled with amine 37 in analogy with scheme 5, step b, leading to 38.

In step f, scheme 7, cleavage of the acetal, removal of the amine protective group, PG, and reductive cyclization of 38 leads to piperazinone 4A. This conversion is performed in analogy with scheme 5, step c.

Scheme 7

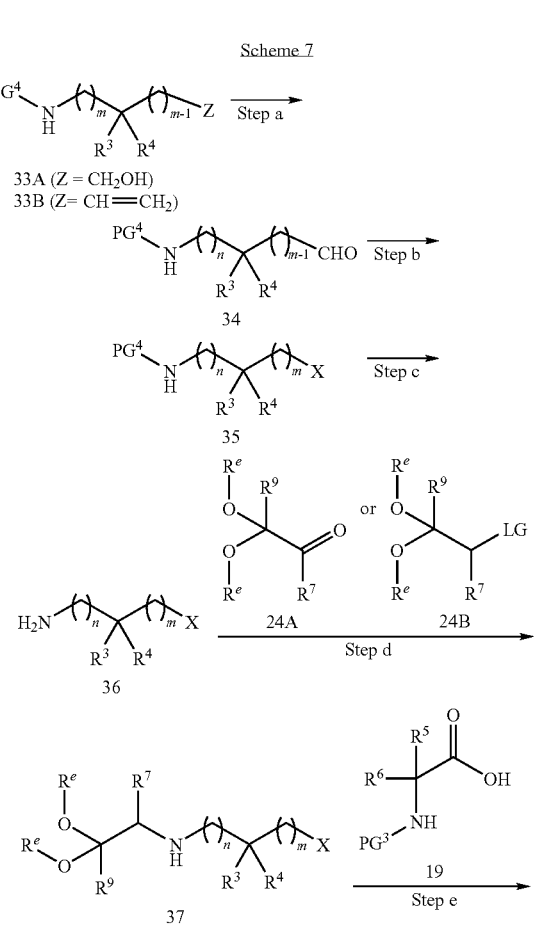

-continued

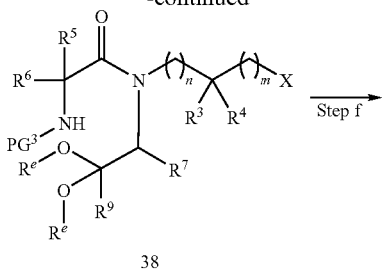
38

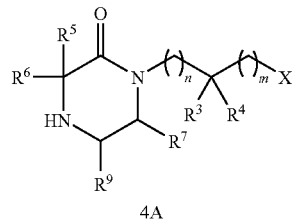
4A

In Scheme 7, X, $R^3$, $R^4$, $R^5$, $R^6$, $R^7$, $R^9$, m and n are as defined before. $R^e$ is lower alkyl, e.g., methyl or ethyl.

Compounds of formula 4A can also be synthesized as described in scheme 8. $PG^1$ is a protective group, e.g., tert-butoxycarbonyl or benzyloxycarbonyl.

In step a, scheme 8, carbonyl compound 31 and amine 36 are converted to piperazinone 39 in analogy to scheme 6, step d.

In step b, scheme 8, the protective group of 39 is removed, thus leading to 4A. This reaction is performed in analogy with scheme 1, step b.

Scheme 8

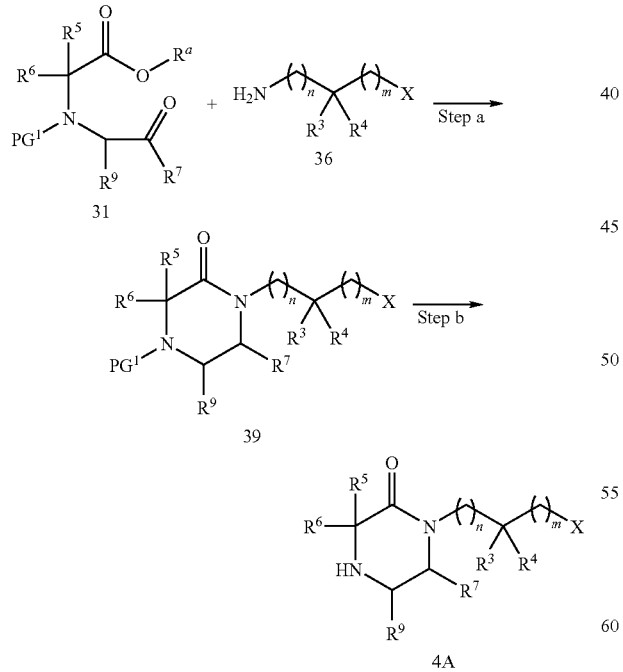

In Scheme 8, X, $R^3$, $R^4$, $R^5$, $R^6$, $R^7$, $R^9$, m and n are as defined before.

Compounds of formula (I) can also be synthesized as described in scheme 9.

In step a, scheme 9, the protective group of 8 is removed, leading to 23. This reaction is performed in analogy with scheme 1, step b.

In the case where p is 0, $R^{10}$ is H and $Y^1$ is C(O), compounds of formula 23 are represented by formula 23A and can also be synthesized as described in scheme 4.

In step b, scheme 9, compound 23 is converted to 40 by reaction with 5A, 5B, or 5C, in analogy with scheme 1, step c.

In step c, scheme 9, alcohol 40 is oxidized to aldehyde 41, in analogy with scheme 2, step c.

In step d, scheme 9, aldehyde 41 is reacted with amine of the general formula $HN(R^1)(R^2)$, in analogy with scheme 2, step d, leading to (I).

Scheme 9

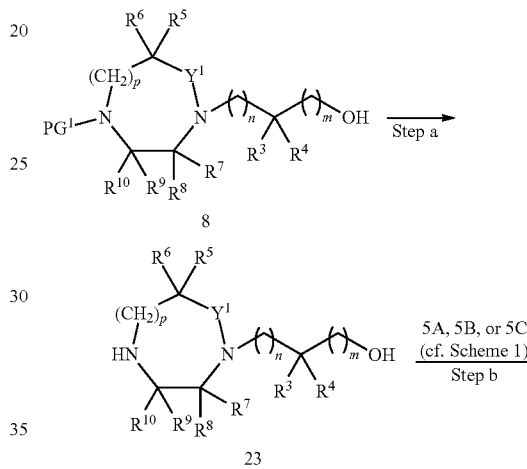

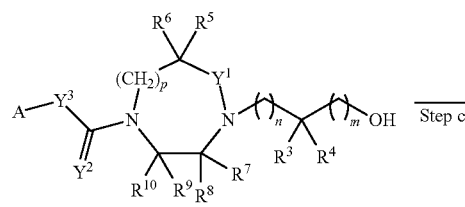
40

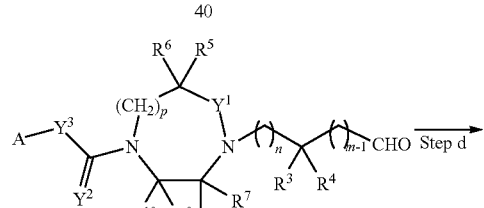
41

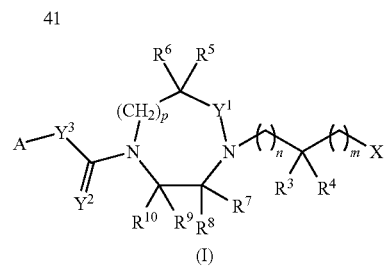
(I)

In Scheme 9, A, X, $Y^1$, $Y^2$, $Y^3$; $R^3$, $R^4$, $R^5$, $R^6$, $R^7$, $R^8$, $R^9$, $R^{10}$, m, n and p are as defined before.

Intermediate 1 in which $R^6$ and $R^8$ are H, p is 1 and $Y^1$ is C(O) is represented by the general formula 1A.

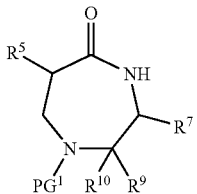

1A $R^5$, $R^7$, $R^9$ and $R^{10}$ are as defined before.

Intermediates 1A are commercially available or can be synthesized as described in scheme 10. $PG^1$ is a suitable protective group such as tert-butoxycarbonyl or benzyloxycarbonyl, $R^e$ is lower alkyl, e.g., methyl or ethyl.

In step a, scheme 10, hydroxyester 12 is converted to azidoester 42 using methods well known in the art, e.g., Mitsunobu reaction. This reaction can be performed using a suitable azide source, e.g., diphenylphosphoryl azide and a dialkyl-azodicarboxylate, e.g., diethyl azodicarboxylate or diisopropyl azodicarboxylate in an inert solvent, e.g., tetrahydrofuran or toluene, at temperatures between 0° C. and 100° C.

In step b, scheme 10, azidoester 42 is converted to [1,4] diazepan-5-one 1A, using reagents and methods known in the art, e.g., reductive cyclization. For instance, the reaction is performed under a hydrogen atmosphere at pressures between 1 bar and 100 bar, in the presence of a suitable catalyst, e.g., palladium on activated charcoal, at temperatures between 0° C. and 100° C., in a solvent such as methanol or ethanol, optionally in the presence of a base, e.g., potassium carbonate.

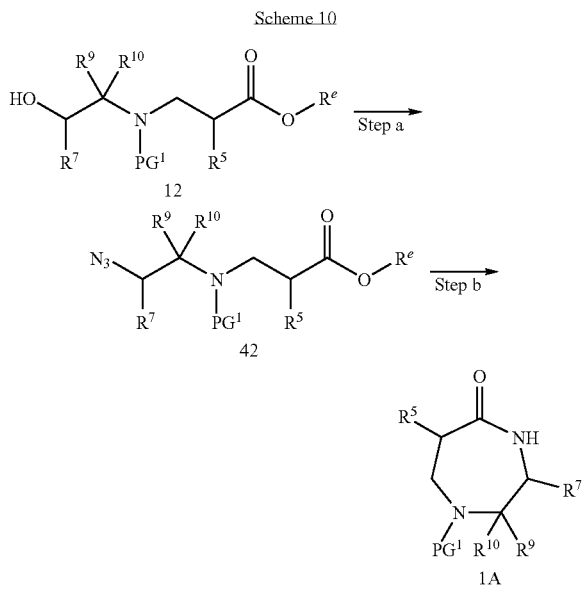

Scheme 10

In Scheme 10, $R^5$, $R^7$, $R^9$ and $R^{10}$ are as defined before. $R^e$ is lower alkyl, e.g., methyl or ethyl.

Intermediates 1A can also be synthesized as described in scheme 11. $PG^1$ is a suitable protective group such as tert-butoxycarbonyl or benzyloxycarbonyl.

In step a, scheme 11, aminoalcohol 10A is reacted with N-benzyloxyacrylamide 43, and the secondary amide intermediate is then transformed into compound 44, in analogy with scheme 3, step a.

In step b, scheme 11, hydroxyamide 44 is cyclized to cyclized to [1,4]diazepan-5-one 45 using methods well known in the art, e.g., Mitsunobu reaction. This reaction requires a phosphine, preferably triphenylphosphine, and a dialkyl-azodicarboxylate, e.g., diethyl azodicarboxylate or diisopropyl azodicarboxylate and is performed in an inert solvent, e.g., tetrahydrofuran or toluene, at temperatures between 0° C. and 100° C.

In step c, scheme 11, the benzyloxy group of 45 is removed, thus leading to 1A. This reaction is performed using reagents and methods known in the art, e.g., catalytic hydrogenation. For instance, the reaction is carried out under a hydrogen atmosphere at pressures between 1 bar and 100 bar, in a solvent such as methanol or ethanol, in the presence of a suitable catalyst, e.g., palladium on activated charcoal, at temperatures between 20° C. and 150° C.

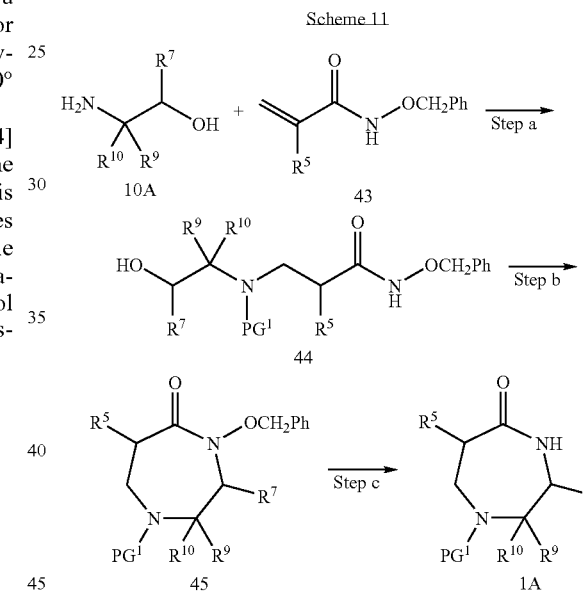

Scheme 11

In Scheme 11, $R^5$, $R^7$, $R^9$ and $R^{10}$ are as defined before.

Intermediate 1 in which $R^6$ is H, p is 1 and $Y^1$ is $S(O)_2$ is represented by the general formula 1B.

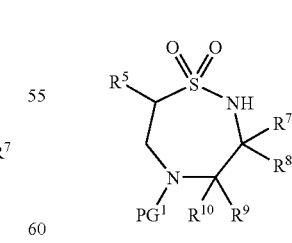

1B $R^5$, $R^7$, $R^8$, $R^9$ and $R^{10}$ are as defined before.

Intermediates 1B can be synthesized as outlined in scheme 12. $PG^1$ is a suitable orthogonal protective group, e.g., tert-butoxycarbonyl or benzyloxycarbonyl, $PG^2$ is a suitable protective group, e.g., tert-butoxycarbonyl, $LG^1$ and $LG^2$ are leaving groups, e.g., chlorine or iodine.

In step a, scheme 12, protected 1,2-diaminoethane derivative 46 is reacted with β-halosulfonyl halide 47 in the presence of a base, e.g., triethylamine, in a solvent such as dichloromethane or tetrahydrofuran, at temperatures between −20° C. and 20° C. The resultant β-halosulfonamide intermediate then undergoes base-mediated elimination of hydrogen halide, thus leading to vinylsulfonamide 48. Suitable bases to perform the elimination step are e.g., aqueous sodium carbonate or aqueous potassium carbonate.

In step b, scheme 12, the protective group of 48 is removed under suitable conditions. In the case where PG is tert-butoxycarbonyl, the deprotection is preferably performed with hydrogen chloride solution in a solvent such as 1,4-dioxane. The resultant N-(2-aminoethyl)-sulfonamide hydrochloride intermediate is then cyclized to [1,2,5]thiadiazepane-1,1-dioxide, using a base, e.g., triethylamine or potassium carbonate, in a solvent such as methanol or ethanol. Finally, protection of the [1,2,5]thiadiazepane-1,1-dioxide intermediate in analogy with scheme 4, step f, leads to 1B.

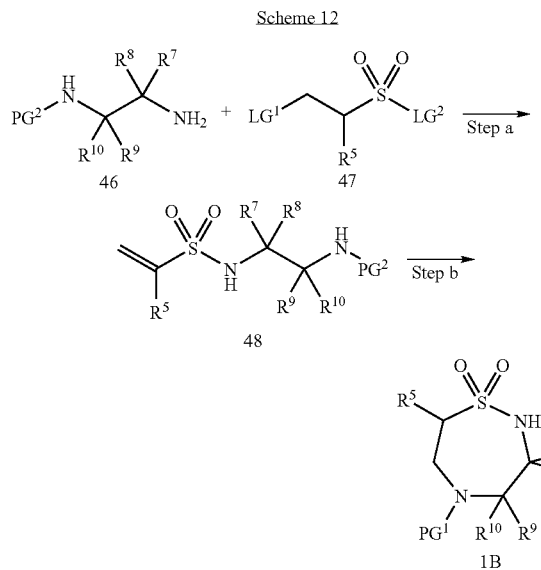

In Scheme 12, $R^5$, $R^7$, $R^8$, $R^9$ and $R^{10}$ are as defined before.

Intermediate 1 in which $R^6$ is H, p is 0 and $Y^1$ is $S(O)_2$ is represented by the general formula IC.

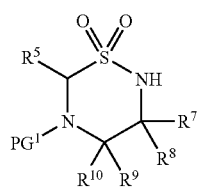

$R^5$, $R^7$, $R^8$, $R^9$ and $R^{10}$ are as defined before.

Intermediates 1C can be synthesized as outlined in scheme 13. $PG^1$ is a suitable protective group, e.g., tert-butoxycarbonyl or benzyloxycarbonyl, $LG^1$ is a leaving group, e.g., chlorine or iodine.

In step a, scheme 13, protected 1,2-diaminoethane derivative 46 is reacted with halomethyl-sulfonyl halide 49 in the presence of a base, e.g., triethylamine, in a solvent such as dichloromethane or tetrahydrofuran, at temperatures between −20° C. and 20° C., leading to sulfonamide 50.

In step b, scheme 13, sulfonamide 50 is cyclized to [1,2,5]thiadiazinane-1,1-dioxide 1C. This reaction is performed in the presence of at least two equivalents of a suitable base, e.g., sodium hydride or potassium tert-butylate, in a solvent such as tetrahydrofuran or N,N-dimethyl-formamide, at temperatures between 0° C. and 100° C.

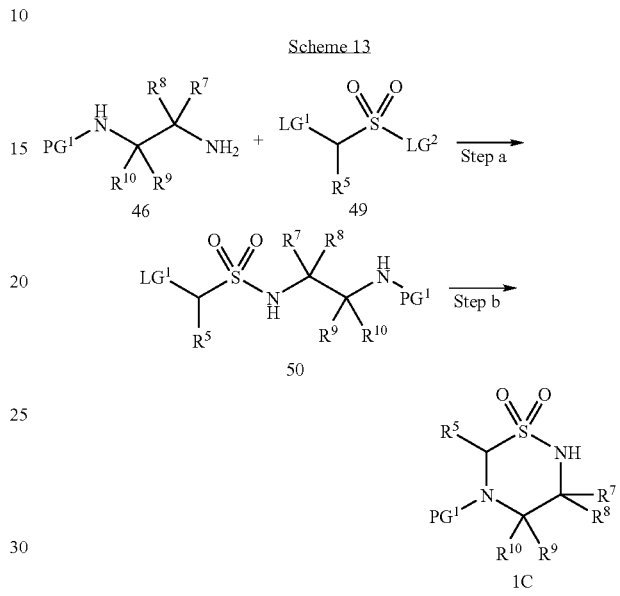

In Scheme 13, $R^5$, $R^7$, $R^8$, $R^9$ and $R^{10}$ are as defined before.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbent or eluent). The invention embraces all of these forms.

As described above, the compounds of formula (I) are CCR2 receptor antagonists, with some antagonist activity also at CCR3 and CCR5. These compounds consequently prevent migration of various leukocyte populations through the blockade of CCR2 stimulation. They therefore can be used for the treatment and/or prevention of inflammatory and/or allergic diseases, such as peripheral arterial occlusive disease, critical limb ischemia (CLI), vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis and/or burns/ulcers in diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and allergy, asthma.

The invention also relates to the use of compounds as described above for the preparation of medicaments for the therapeutic and/or prophylactic treatment of inflammatory and/or allergic diseases, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable bowel syndrome, Crohn's disease, multiple sclerosis, neuropathic pain, atherothrombosis, burns/ulcers in diabetes/CLI, and asthma. Such medicaments comprise a compound as described above.

The invention also relates to the process and the intermediates for manufacturing the compounds of formula (I) as well as the process for manufacturing the intermediates.

CCR2 receptor antagonistic activity by the compounds of the present invention can be demonstrated by the following assays.

Receptor Binding Assays

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a topcounter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 mM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds of formula (I) of the present invention exhibit $IC_{50}$ values in the Ca mobilisation assay of 1 nM to 10 µM, preferably 1 nM to 1.5 µM for CCR2. The following table shows measured values for some selected compounds of the present invention.

| Example | IC50 (µM) | Example | IC50 (µM) |
|---|---|---|---|
| 1 | 0.47 | 2 | 0.04 |
| 3 | 0.27 | 4 | 0.01 |
| 5 | 0.05 | 6 | 0.84 |
| 7 | 0.37 | 9 | 0.42 |
| 10 | 0.78 | 11 | 0.98 |
| 18 | 0.60 | 21 | 0.37 |
| 22 | 0.77 | 25 | 0.38 |
| 26 | 0.58 | 27 | 0.54 |
| 30 | 0.96 | 35 | 0.94 |
| 37 | 0.05 | 38 | 0.21 |
| 40 | 0.36 | 42 | 0.11 |
| 43 | 0.61 | 45 | 0.002 |
| 46 | 0.007 | 47 | 0.007 |
| 48 | 0.37 | 49 | 0.16 |
| 50 | 0.12 | 51 | 0.25 |
| 52 | 0.96 | 53 | 0.001 |
| 54 | 0.006 | 55 | 0.004 |
| 56 | 0.002 | 57 | 0.24 |
| 58 | 0.003 | 60 | 0.06 |
| 61 | 0.21 | 62 | 0.03 |
| 63 | 0.0051 | 65 | 0.021 |
| 66 | 0.033 | 68 | 0.003 |
| 69 | 0.005 | 70 | 0.004 |
| 71 | 0.002 | 72 | 0.008 |
| 73 | 0.021 | 74 | 0.064 |
| 75 | 0.003 | 76 | 0.003 |
| 77 | 0.11 | 78 | 0.002 |
| 79 | 0.003 | 80 | 0.001 |
| 81 | 0.009 | 82 | 0.004 |
| 83 | 0.009 | 84 | 0.042 |
| 85 | 0.18 | 86 | 0.192 |
| 87 | 0.005 | 88 | 0.097 |
| 89 | 0.025 | 90 | 0.001 |
| 91 | 0.006 | 92 | 0.624 |
| 93 | 0.002 | 94 | 0.293 |
| 95 | 0.565 | 99 | 0.024 |
| 101 | 0.316 | 104 | 0.382 |
| 106 | 0.001 | 107 | 0.002 |
| 108 | 0.002 | 109 | 0.010 |
| 110 | 0.005 | 111 | 0.017 |
| 112 | 0.002 | 113 | 0.001 |
| 114 | 0.006 | 115 | 0.010 |
| 116 | 0.005 | 118 | 0.003 |
| 119 | 0.004 | 120 | 0.002 |
| 121 | 0.006 | 122 | 0.023 |
| 123 | 0.248 | 124 | 0.004 |
| 125 | 0.016 | | |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

EXAMPLES

The following Examples serve to illustrate the present invention in more detail. They are, however, not intended to limit its scope in any manner.

Abbreviations:

The following are a list of abbreviations and/or acronyms with their corresponding definitions used in the following examples: aq.=aqueous, eq.=equivalents, FTIR=Fourier transform infrared spectroscopy, GC=gas chromatography, HPLC=high-pressure liquid chromatography, EPC=In-process control, ISP=ion spray, MS=mass spectrometry, NMR=nuclear magnetic resonance spectroscopy, sat=saturated, TEMPO=2,2,6,6-tetramethylpiperidin-1-oxyl, and TLC=thin layer chromatography.

Intermediate 1

(rac)-4-(tert-Butyl-dimethyl-silanyloxy)-2-iodo-butyric acid methyl ester

A) (S)-4-(tert-Butyl-dimethyl-silanyloxy)-2-methanesulfonyloxy-butyric acid methyl ester A solution of 2.48 g (10.00 mmol) of methyl (S)-4-(tert-butyldimethylsilyloxy)-2-hydroxybutanoate (*J. Am. Chem. Soc.* 2005, 127, 1090) in 50 ml of dichloromethane was treated with 2.09 ml (15.00 mmol, 1.5 eq) of triethylamine and at 0° C. during 5 min with 0.82 ml (10.50 mmol, 1.051 eq) of methanesulfonyl chloride. After 1 h at 0° C. the reaction was partitioned between 10% aq. potassium dihydrogenphosphate solution/diethyl ether (×3), the organic phases were washed with sat. aq. sodium hydrogencarbonate solution (freshly prepared) and 10% aq. sodium chloride solution, dried over $Na_2SO_4$ and evaporated to give 2.91 g (89%) of the title compound as yellow oil. MS: 327.1 ($MH^+$).

B) (rac)-4-(tert-Butyl-dimethyl-silanyloxy)-2-iodo-butyric acid methyl ester

A solution of 2.89 g (8.85 mmol) of (S)-4-(tert-butyl-dimethyl-silanyloxy)-2-methanesulfonyloxy-butyric acid methyl ester in 90 ml of 2-butanone was treated with 2.65 g (17.70 mmol) of sodium iodide and stirred at 90° C. for 1¼ h. The reaction was cooled, filtered and evaporated. The residue was suspended in dichloromethane treated with $Na_2SO_4$ and filtered to give after evaporation 2.94 g (93%) of the title compound as dark brown oil. MS: 343.0 $(M-CH_3)^+$.

Intermediate 2

(S)-6-Aza-spiro[2.5]octan-4-ol; hydrochloride a) 4-Hydroxy-6-aza-spiro[2,5]octane-6-carboxylic acid tert-butyl ester Method A To a solution of diethylzinc (1.1 M solution in toluene, 37.5 ml, 0.04 mmol) in 1,2-dichloroethane (80 ml) at 0° C. was added chloroiodomethane (5.99 ml, 0.08 mmol) under Ar. This mixture was stirred for 15 minutes before a solution of 3-hydroxy-4-methylene-piperidine-1-carboxylic acid tert-butyl ester (*J. Org. Chem.* 2001, 66, 2487) (4.19 g, 19.6 mmol) in 1,2-dichloroethane (10 ml) was added, after which time the reaction was stirred for 0.5 h at 0° C. and then allowed to reach room temperature, stirring for a further 1 h. The reaction was then quenched by addition of sat. aq. ammonium chloride solution, separated, and the organic dried ($Na_2SO_4$) and concentrated. Purification by flash column chromatography ($SiO_2$; ethyl acetate/heptane 2:8-1:1) afforded the title product (2.4 g, 54%) as a crystalline solid. MS: 228.2 ($MH^+$).

Method B 2.00 g (9.4 mmol, 1 eq.) 3-hydroxy-4-methylene-piperidine-1-carboxylic acid tert-butyl ester were dissolved in toluene at 25° C. 17.05 ml (2 eq.) 1.1 M diethyl zinc solution in toluene were added at such a rate as to maintain the reaction temperature below 30° C. After 15-30 min at 25° C., 2.29 ml (3 eq.) diiodomethane were added over 2-3 h maintaining the reaction temperature at 25° C. (the reaction is best followed by Tr-Tj measurements and/or in-line FTIR reaction monitoring). After 30-60 min after the end of addition, 4.57 ml 2-ethyl-hexanoic acid were added to the resulting white suspension at such a rate as to maintain the reaction temperature between 25-30° C. The heavy white suspension was stirred for 30 min. 10 ml heptane were added followed by a mixture consisting of 20 ml 25% aq. ammonia solution and 30 ml water. The organic phase was separated and washed with a mixture consisting of 10 ml 25% aq. ammonia solution and 30 ml water. The organic phases were washed with 20 ml half saturated aq. sodium chloride solution, combined, dried over sodium sulfate, filtered and concentrated under reduced pressure to an oil (may crystallize upon standing). The crude spiro-piperidinol was purified by crystallization in heptane or alternatively in tert-butyl methyl ether/heptane providing the title product in ca 80% yield as a white powder.

b) (S)-4-Hydroxy-6-aza-spiro[2.5]octane-6-carboxylic acid tert-butyl ester

Method A

The title compound was prepared by chiral separation of (rac)-4-hydroxy-6-aza-spiro[2.5]octane-6-carboxylic acid tert-butyl ester on a Chiralpak® AD column (heptane/2-propanol 95:5).

Method B

4-Hydroxy-6-aza-spiro[2.5]octane-6-carboxylic acid tert-butyl ester (3.00 g; 13.07 mmol) was dissolved in tert-butyl methyl ether (20.5 ml) and vinyl butyrate (6.5 ml). The solution was heated to 50° C. and the reaction started by the addition of Lipase TL (3.0 g; Meito Sangyo, Tokyo). The solution was stirred at 50° C. for 46 h until the enantiomeric excess of the retained alcohol was >99%. The enzyme was filtered off, the filter cake washed with tert-butyl methyl ether and the filtrate concentrated in vacuo. The residual oil was chromatographed on silicagel (80 g; 0.040-0.063 mm; dichloromethane→dichloromethane/acetone 9:1) to separate the formed optically enriched (R)-butyrate from the retained (S)-alcohol (1.18 g white crystals; 40%). Analytics: >99 GC; >99% ee (GC on BGB-176; 30 m×0.25 mm; $H_2$; 1.2 bar; 80° C. to 210° C. with 3° C./min; inj. 200° C.; Det. 215° C.; Retention times: (R)-alcohol 28.58 min, (S)-alcohol 29.00 min). $[\alpha]_D$=-43.35° (c=1.00, $CHCl_3$).

Method C

Step 1: 4-Oxo-6 aza-spiro[2.5]octane-6-carboxylic acid tert-butyl ester

The title compound was produced from 4-hydroxy-6-aza-spiro[2.5]octane-6-carboxylic acid tert-butyl ester, either by TEMPO/bleach oxidation or by Swern oxidation:

a) TEMPO/Bleach Oxidation

To a solution of 4-hydroxy-6-aza-spiro[2.5]octane-6-carboxylic acid tert-butyl ester (20.0 g, 88.0 mmol) in dichloromethane (170 ml) was added sodium bromide (1.092 g, 10.6 mmol), sodium bicarbonate (2.439 g, 29.0 mmol) and 2,2,6,6-tetramethylpiperidine 1-oxyl (237.1 mg, 1.49 mmol). The mixture was cooled to -5° C. and sodium hypochlorite solution (9.5% in water, 55.16 ml) was added within 10 min resulting in a red coloration and a temperature rise to 9° C. The mixture was stirred for 35 min at 0-5° C. and, as conversion was incomplete (2.5% starting material remaining), additional sodium hypochlorite solution (9.5% in water, 7.0 ml) was added within 30 min and the mixture stirred for another 30 min at 0° C. GC analysis indicated complete conversion (<0.1% starting material remaining). Sodium thiosulfate solution (10% in water, 100 ml) was added within 10 min resulting in decoloration. The organic phase was separated, washed with water (100 ml), dried over sodium sulfate (50 g), filtered and evaporated (15 mbar, 40° C.) to afford 4-oxo-6-aza-spiro[2.5]octane-6-carboxylic acid tert-butyl ester as yellowish powder (19.84 g), GC purity 99a %. The powder was dissolved in warm tert-butyl methyl ether (20 ml), heptane (60 ml) was added to induce crystallization and the white suspension stirred at 0-5° C. for 1.5 h. Filtration, washing with heptane (20 ml) and drying (10 mbar, 45° C.) afforded 4-oxo-6-aza-spiro[2.5]octane-6-carboxylic acid tert-butyl ester (17.25 g, 87%) as white crystalline material, GC purity 100a %. $^1$H-NMR ($CDCl_3$, 300 MHz): 4.08 (s, $CH_2$(5)), 3.66 (m, $CH_2$(7)), 1.88 (m, $CH_2$(8)), 1.48 (s, tert-Bu), 1.40 (m, 2H), 0.81 (m, 2H).

b) Swern Oxidation

To a solution of oxalyl chloride (42.35 ml, 0.480 mol) in dichloromethane (910 ml) was added a solution of dimethylsulfoxide (68.24 ml, 0.961 mol) in dichloromethane (910 ml) at -70° C. within 45 min. The solution was stirred for 15 min and a solution of 4-hydroxy-6-aza-spiro[2.5]octane-6-carboxylic acid tert-butyl ester (91.00 g, 0.400 mol) in dichloromethane (910 ml) was added within 40 min keeping the internal temperature at below -60°. The mixture was stirred for 35 min and triethylamine (280.4 ml, 2.00 mol) was added at below -60° C. within 10 min. The cooling bath was removed and the yellow suspension was stirred for 1 h then quenched with water (1.4 l). The organic phase was separated, washed with water (3×1 l) and sat. aq. sodium chloride solution (3 l) and evaporated. The residual orange powder was dissolved in tert-butyl methyl ether (1.40 l), the turbid solution filtered (Hyflo Speedex) to remove some insoluble material and the clear filtrate evaporated to provide crude 4-oxo-6-aza-spiro[2.5]octane-6-carboxylic acid tert-butyl ester as yellow powder (91.9 g). The material was re-dissolved in tert-butyl methyl ether (300 ml) and purified by filtration over silica gel (700 g) using a 3:1 heptane/tert-butyl methyl ether mixture (6.5 l). Evaporation and drying (10 mbar, 40° C.) afforded 4-oxo-6-aza-spiro[2.5]octane-6-carboxylic acid tert-butyl ester as whitish powder (80.58 g, 89%), GC purity 100a %.

Step 2:
(S)-4-Hydroxy-6-aza-spiro[2.5]octane-6-carboxylic acid tert-butyl ester

D(+)-glucose monoydrate (300 g) and magnesium chloride hexahydrate (1.0 g) were dissolved in 10 mM MES buffer pH 6.5 (2.4 L; Sigma M3671). After addition of 4-oxo-6-aza-spiro[2.5]octane-6-carboxylic acid tert-butyl ester (300 g; 1.33 mmol) and β-NAD (3.0 g; free acid; Roche Diagnostics Cat. No. 10 004 626) the pH was re-adjusted and the suspension heated to 35° C. The reaction was started by adding ketoreductase KRED-NADH-117 (3.0 g; former Biocatalytics, now Codexis) and glucose dehydrogenase GDH-102 (300 mg; Biocatalytics). The suspension was vigorously stirred at 35° C. keeping the pH constant at 6.5 by the controlled addition (pH-stat) of 1.0 M aq. sodium hydroxide solution. After a consumption of 1.307 L (corresponding to 98% conversion; after 17 h) the reaction mixture was extracted with ethyl acetate (10 L). The organic phase was dried over sodium sulfate and concentrated in vacuo (200 mbar/45° C.) until evaporation fell off. Upon cooling the oily residue (411 g) started to crystallize and was stirred with heptane (1 L) for 2 h. The crystals were filtered off and the filtrate evaporated to dryness, redissolved in ethyl acetate (150 ml) and concentrated in vacuo as described above. The crystal suspension formed again upon cooling was stirred with heptane (200 ml; 2 h) and the crystals filtered off. Both crops of crystals were washed with heptane and dried under high vacuum to yield the title compound in 93% yield (250.77 g and 34.60 g white crystals), each having a purity of >98.5% GC and 99.8% ee. $[\alpha]_D=-44.97°$ (c=1.00, CHCl$_3$).
Method D Step 1:
(S)-3-hydroxy-4-methylene-piperidine-1-carboxylic acid tert-butyl ester 3-Hydroxy-4-methylene-piperidine-1-carboxylic acid tert-butyl ester (4.50 g; 21.10 mmol) was dissolved in tert-butyl methyl ether (63 ml) and vinyl butyrate (22.5 ml). The solution was heated to 50° C. and the reaction started by the addition of Lipase TL IM (1.08 g (carrier-fixed); Novozymes, Denmark). The solution was stirred at 50° C. for 20 h until the enantiomeric excess of the retained alcohol was >99%. The enzyme was filtered off, the filter cake washed with tert-butyl methyl ether and the filtrate concentrated in vacuo. The residual oil was chromatographed on silicagel (100 g; 0.040-0.063 mm; dichloromethane→dichloromethane/acetone 9:1) to separate the formed optically enriched (R)-butyrate from the retained (S)-alcohol (1.83 g white crystals; 41%). Analytics: >99 GC; >99% ee (GC on BGB-176; 30 m×0.25 mm; H$_2$; 1.2 bar; 80° C. to 210° C. with 3° C./min; inj. 200° C.; Det. 210° C.; retention times: (R)-alcohol 29.60 min, (S)-alcohol 29.81 min). $[\alpha]_D=-17.70°$ (c=1.00, CHCl$_3$).

Step 2:
(S)-4-Hydroxy-6-aza-spiro[2.5]octane-6-carboxylic acid tert-butyl ester

The title compound is produced analogously to intermediate 2a, Method B from (S)-3-hydroxy-4-methylene-piperidine-1-carboxylic acid tert-butyl ester.

c) (S)-6-Aza-spiro[2.5]octan-4-ol; hydrochloride

A solution of (S)-4-hydroxy-6-aza-spiro[2.5]octane-6-carboxylic acid tert-butyl ester (3.26 g, 14.3 mmol) in ethanol (10 ml) was treated at room temperature with hydrogen chloride solution (4 M in 1,4-dioxane, 30 ml), then after 1 h tert-butyl methyl ether (40 ml) was added. The suspension was stirred for 1 h, then the precipitate was collected by filtration to afford the title compound (2.11 g, 90%). White solid, MS: 128.1 (M+H)$^+$.

Alternative preparation of
(S)-6-Aza-spiro[2.5]octan-4-ol: hydrochloride i) Cyclopropanecarboxylic Acid Tert-Butyl Ester 219.1 g (1.91 mol, 1 eq.) potassium tert-butylate were suspended in 2.5 L tert-butyl methyl ether and cooled to 0-5° C. 200 g (1 eq.) cyclopropanecarbonyl chloride were added over 60 min, maintaining the temperature between 0-5° C. (ice-ethanol bath cooling). In-line FTIR reaction monitoring indicates a feed controlled reaction. The reaction mixture was stirred 30 min at 0-5° C. and 1 L of 5% aq. sodium hydrogencarbonate solution was added. The aqueous phase was separated and extracted with 500 ml tert-butyl methyl ether. The organic phases were washed with 500 ml half saturated aq. sodium chloride solution, combined and concentrated under reduced pressure (30° C./150 mbar) to provide 271 g of the title compound (91% yield corrected for 8% residual tert-butyl methyl ether).

ii) 1-Allyl-cyclopropanecarboxylic acid tert-butyl ester 15.9 ml (1.15 eq.) diisopropylamine were dissolved in 65 ml tetrahydrofuran and cooled to ca –10° C. 65 ml (1.08 eq.) 1.6 M butyllithium solution in hexane were added over 25 min, maintaining the temperature between –10° C. and 0° C. After 50 min at ca. –5° C., the reaction mixture was cooled to –75° C. A solution of 15 g (96.7 mmol, 1 eq., 92% w/w purity) cyclopropanecarboxylic acid tert-butyl ester in 20 ml tetrahydrofuran was added over 15 min keeping the temperature between –75° C. and –70° C. The reaction mixture was stirred 5 h at –75° C. (milky reaction mixture obtained after 2.5 h). A solution of 12.87 g (1.10 eq.) allyl bromide was added over 20 min keeping the temperature between –75° C. and –60° C. The reaction mixture was stirred at –78° C. for 1 h, warmed to room temperature and stirred overnight. The reaction mixture was cooled to 0° C. 100 ml sat. aq. ammonium chloride solution were added followed by 30 ml water providing a clear biphasic mixture. The mixture was extracted 3 times with 50 ml tert-butyl methyl ether. The organic phases were combined, dried over sodium sulfate, filtered and concentrated under reduced pressure (40° C./20 mbar) to afford 16.44 g of crude product. The crude product was distilled (2 mbar; ca 40° C. distillation head temperature) to provide the title compound in ca 65% yield.

iii) 1-(2-Oxo-ethyl)-cyclopropanecarboxylic acid tert-butyl ester 6.9 g (36.34 mmol, 1 eq., 96% a % by GC) 1-allyl-cyclopropanecarboxylic acid tert-butyl ester were dissolved in 40 ml dichloromethane and 40 ml methanol. The solution was cooled to –72° C. and the ozone was bubbled through the reaction mixture until a blue color was obtained. Then nitrogen was bubbled to remove excess ozone until a colorless solution was obtained. 10 ml (3.68 eq.) dimethyl sulfide and 14 ml (2.76 eq.) triethylamine were added. The reaction mixture was warmed to room temperature and stirred overnight at that temperature (peroxide test negative, pH 7-8). The yellowish reaction mixture was added to 100 ml sat. aq. ammonium chloride solution (exothermic) and extracted 3 times with 70 ml dichloromethane. The organic phases were combined, dried over sodium sulfate, filtered and concentrated under reduced pressure to provide the crude aldehyde, which was purified by filtration over SiO$_2$ (dichloromethane; TLC: ethyl acetate/heptane 1:2) to provide 3.90 g (96% GC, 56% yield) of the title compound as an oil.

iv) 1-[2-(Benzyl-tert-butoxycarbonylmethyl-amino)-ethyl]-cyclopropanecarboxylic acid tert-butyl ester 10.5 g (54.7 mmol, 1 eq.) 1-(2-oxo-ethyl)-cyclopropanecarboxylic acid tert-butyl ester and 13.21 g (1.08 eq.) N-benzylglycine tert-butyl ester were dissolved in 140 ml toluene. 21 g (1.63 eq.) sodium triacetoxyborohydride were added (exotherm from 25° C. to 28° C.) and the reaction mixture was stirred 5 h at room temperature (IPC by GC). A solution of 2 ml (0.64 eq.) acetic acid in 15 ml toluene was added. After 30 min at room temperature, the reaction mixture was cooled to 0° C. and 100 ml sat. aq. sodium hydrogencarbonate solution was added over 40 min (foaming). 50 ml ethyl acetate were added. The mixture was stirred for 30 min at room temperature. The mixture was extracted with 200 ml and a second time with 50 ml ethyl acetate. The organic phases were washed with 50 ml sat. aq. sodium hydrogencarbonate solution followed by 50 ml sat. aq. sodium chloride solution. The organic phases were combined, dried over sodium sulfate, filtered and concentrated under reduced pressure to give 21.5 g of the title compound as an oil (ca. 95% yield, corrected for ca 3% residual toluene and 3% amine starting material).

v) 6-Benzyl-6-aza-spiro[2.5]octan-4-one hydrochloride 10.8 g (24.4 mmol, 1 eq.) 1-[2-(benzyl-tert-butoxycarbonylmethyl-amino)-ethyl]-cyclopropanecarboxylic acid tert-butyl ester were dissolved in 35 ml tetrahydrofuran. 50 ml (2.05 eq.) 1 M lithium hexamethyldisilazanide solution in tetrahydrofuran were added dropwise over 2.5 h maintaining the temperature between 20° C. and 25° C. After 2 h at room temperature (IPC by HPLC), the reaction mixture (containing the lithium salt of 6-benzyl-4-hydroxy-6-aza-spiro[2.5]oct-4-ene-5-carboxylic acid tert-butyl ester) was cooled to −10° C. (ice ethanol cooling bath) and 75 ml 1 M aq. sulfuric acid solution were added (temperature increased to 2° C.). The reaction mixture was warmed to room temperature and the tetrahydrofuran removed under reduced pressure at 40° C. The resulting reaction mixture was heated to 40° C. for 1 h, was stirred 15 h at room temperature and an additional 3 h at 40° C. to complete the reaction (IPC by GC; intermediate 6-benzyl-4-hydroxy-6-aza-spiro[2.5]oct-4-ene-5-carboxylic acid tert-butyl ester is hydrolyzed and decarboxylation follows). The reaction mixture was cooled to 0° C. and was neutralized to pH 7.4 by addition of 10 ml 2 M aq. sodium hydroxide solution and 50 ml 1 M aq. sodium hydrogencarbonate solution were added, setting the pH to 9.4. The crude solution was extracted with tert-butyl methyl ether and ethyl acetate. The organic phases were combined, dried over sodium sulfate and filtered over a plug of $SiO_2$. The solution was concentrated under reduced pressure (45° C./20 mbar) to give 4.56 g of the crude product as free base. The crude oil was dissolved in 8 ml ethyl acetate, cooled to 0° C. and 5.1 ml hydrogen chloride solution (4.3 M in ethyl acetate) were added dropwise (exotherm 2° C. to 18° C.). The reaction mixture was stirred overnight at room temperature (gummy crystals) and filtered. The filter cake was washed with 10 ml ethyl acetate and dried under reduced pressure until constant weight to give 4.54 g of the title compound as off-white crystals (74% yield).

vi) (S)-6-Benzyl-6-aza-spiro[2.5]octan-4-ol

A mixture of 300 mg of 6-benzyl-6-aza-spiro[2.5]octan-4-one hydrochloride (1.19 mmol, 1 eq.), 1.5 ml of 2-propanol and 28 ml of 30 mM aq. TRIS-HCl buffer (pH 8.1) was heated to 35° C. The pH was re-adjusted to 8.0. The reaction was started by adding □-NAD (1 mg; free acid; Roche Diagnostics Cat. No. 10 004 626) and ketoreductase KRED-NADH-117 (29.3 mg; Codexis [ex. Biocatalytics]). The suspension was stirred at 35° C. keeping the pH constant at 8.0 by the controlled addition (pH-stat) of 1.0 M aq. sodium hydroxide solution. After roughly 80 area % conversion and 1 d, further 2-propanol (0.3 ml), □-NAD (3 mg; free acid; Roche Diagnostics Cat. No. 10 004 626), ketoreductase KRED-NADH-1 17 (30 mg; Codexis [ex. Biocatalytics]) and magnesium chloride (12.7 mg) were added. After 4 d, 98.5 area % conversion and 5.9 ml consumption of 1.0 M aq. sodium hydroxide solution the reaction mixture was stopped by the addition of sodium chloride (9 g), ethyl acetate (30 ml) and filter aid (1 g Dicalite Speedex). The mixture was stirred 30 min. and filtered. The filtrate was extracted 3 times with 30 ml ethyl acetate. The combined organic phases were dried over sodium sulfate, filtered and concentrated under reduced pressure to provide the crude product in over 99.9% e.e. Purification by flash chromatography provided the title compound as a colorless oil.

vii) (S)-6-Aza-spiro[2.5]octan-4-ol 100 mg (S)-6-benzyl-6-aza-spiro[2.5]octan-4-ol were dissolved in 1 ml methanol and hydrogenated over palladium on barium sulfate. After de-benzylation (IPC by GC), the catalyst was filtered and the filtrate was concentrated under reduced pressure to provide the title compound. The amino alcohol was treated with di-tert-butyl-dicarbonate in methanol in the presence of triethylamine. The crude tert-butoxycarbonyl-protected amine product was analyzed by chiral GC (BGB-176; 30 m×0.25 mm; 80° C. to 210° C. in 43 min) and proved to be identical with intermediate 2b.

The hydrochloride salt of the title compound can be obtained by treating the aminoalcohol with HCl in ethyl acetate.

Preparation of N-Benzylglycine Tert-Butyl Ester 40 g (205 mmol, 1 eq.) tert-butyl bromoacetate were dissolved in 200 ml acetonitrile. The solution was cooled to 0-5° C. and 47 g benzylamine (2.14 eq.) in solution in 90 ml acetonitrile were added over 15 min. After 5 min, the reaction mixture was warmed to room temperature and stirred for 3 h (IPC by GC). The resulting suspension was filtered and evaporated to constant weight to give 49 g of a yellow oil. The oil was dissolved in 200 ml heptane and washed 3 times with 50 ml aq. sodium hydrogencarbonate solution. The organic phase was dried over sodium sulfate, filtered and evaporated to give 35.8 g of the crude product. Distillation under high vacuum afforded 27.2 g of the title product (95% pure by GC).

Intermediate 3

(3S,4S)-4-Methyl-piperidin-3-ol; hydrochloride a) (rac, trans)-3-Hydroxy-4-methyl-piperidine-1-carboxylic acid tert-butyl ester (rac, trans)-1-Benzyl-4-methyl-piperidin-3-ol (*Tetrahedron. Lett.* 2000, 41, 5817) (13.0 g, 63 mmol) was dissolved in methanol with palladium hydroxide (20% on activated charcoal, 4 g) and stirred under a hydrogen atmosphere (balloon) for 16 h after which time di-tert-butyl dicarbonate (13.8 g, 63 mmol) was added, the reaction stirred for 1 h, filtered through Hyflo and concentrated to afford the title product (13.3 g, 98%) as a crystalline solid. MS: 216.2 ($MH^+$).

b) (rac, trans)-4-Methyl-3-(4-nitro-benzoyloxy)-piperidine-1-carboxylic acid tert-butyl ester (rac, trans)-3-Hydroxy-4-methyl-piperidine-1-carboxylic acid tert-butyl ester (6.0 g, 28 mmol) was dissolved in tetrahydrofuran (40 ml) with triphenylphosphine (8.9 g, 34 mmol), 4-nitrobenzoic acid (5.7 g, 34 mmol) and cooled to 0° C. before dropwise addition of diisopropyl azodicarboxylate (6.9 g, 34 mmol). The ice bath was removed and the reaction allowed to come to room temperature, stirring for 16 h. The reaction was then directly absorbed onto silica gel and purified by flash column chromatography (ethyl acetate/heptane 2:8) to afford the title product (4.0 g, 40%) as a white solid. MS: 365.2 ($MH^+$).

c) (rac, cis)-3-Hydroxy-4-methyl-piperidine-1-carboxylic acid tert-butyl ester (rac, trans)-4-Methyl-3-(4-nitro-benzoyloxy)-piperidine-1-carboxylic acid tert-butyl ester (5.0 g, 14 mmol) was dissolved in methanol (70 ml) and 6 M aq. sodium hydroxide solution (4.5 ml, 27 mmol) was added. The reaction was stirred for 1 h after which time the solvent removed under vacuum, the residue portioned between water and dichloromethane and the organic collected, dried ($Na_2SO_4$) and concentrated to afford the title product (2.6 g, 87%) as a crystalline solid. MS: 216.1 ($MH^+$).

d) (3S,4S)-4-Methyl-piperidin-3-ol; hydrochloride (rac, cis)-3-Hydroxy-4-methyl-piperidine-1-carboxylic acid tert-butyl ester was separated on a Chiralpak AD column (Isopropanol/Heptane 5:95) and subsequently, the (−)-enantiomer was deprotected with hydrogen chloride solution in dioxane to afford the title compound as a white powder. MS:116.2 ($MH^+$).

Intermediate 4

(3S,5S)-5-Methyl-piperidin-3-ol; hydrochloride a) (S)-3-(Benzyl-ethoxycarbonylmethyl-amino)-butyric acid ethyl ester

To ethanol (55 ml) cooled to 0° C. was added acetyl bromide (41 ml, 0.6 mol) dropwise, followed by a solution of (S)-4-methyl-dihydro-furan-2-one (*Tetrahedron* 1983, 39, 3107; 18.6 g, 0.2 mol) in ethanol (20 ml). The ice bath was removed and the reaction allowed to reach room temperature. After 2 h of stirring the reaction was concentrated, the residue redissolved in dichloromethane, washed with sat. aq. sodium hydrogencarbonate solution, dried ($Na_2SO_4$) and concentrated affording (S)-4-bromo-3-methyl-butyric acid ethyl ester (33.6 g, quantitative). This was redissolved in ethanol (100 ml), cooled to 0° C. and N-benzylglycine ethyl ester (28.2 g, 0.14 mol) and triethylamine (22.4 ml, 0.16 mmol) were added. The reaction was then warmed to 75° C. for 4 d after which time the reaction was concentrated, the residue redissolved in dichloromethane, washed with sat. aq. sodium hydrogencarbonate solution, dried ($Na_2SO_4$) and concentrated. Purification by flash column chromatography (ethyl acetate/heptane 5:95) afforded the titled product as a light gold oil (20.3 g, 43%). MS (ISP)=322.2 ($M+H^+$).

b) (S)-1-Benzyl-5-methyl-piperidin-3-one

To a suspension of sodium hydride (55% dispersion in mineral oil, 6.4 g, 14 mmol) in toluene (90 ml) was added (S)-3-(benzyl-ethoxycarbonylmethyl-amino)-butyric acid ethyl ester (20.3 g, 0.06 mol) in toluene (10 ml), followed by ethanol (1 ml). A vigorous reaction ensued, after 15 minutes the reaction was diluted with ethyl acetate, washed with 10% aq. citric acid solution, dried ($Na_2SO_4$) and concentrated. The residue was purified by flash column chromatography (ethyl acetate/heptane 1:9) affording a complex mixture of diastereomers (7.2 g, 42%). A portion of this material (3.5 g, 13 mmol) was dissolved in 25% aq. hydrochloric acid solution (20 ml) and heated in a loosely closed tube at 120° C. for 36 h. The solvent was evaporated, the residue redissolved in dichloromethane, washed with sat. aq. sodium hydrogencarbonate solution, dried ($Na_2SO_4$) and concentrated. Purification by flash column chromatography (ethyl acetate/heptane 1:4) afforded the titled product as a crystalline solid (1.1 g, 43%). MS (ISP)=204.3 ($M+H^+$).

c) (3S,5S)-1-Benzyl-5-methyl-piperidin-3-ol

To a solution of (S)-1-benzyl-5-methyl-piperidin-3-one (1.1 g, 5 mmol) in dry tetrahydrofuran (15 ml) at −78° C. was added K-selectride (10.8 ml, 11 mmol, 1 M solution in tetrahydrofuran). After 2 h at −78° C. a few drops of water were cautiously added, the reaction allowed to reach room temperature, the tetrahydrofuran removed by evaporation and the residue the residue redissolved in dichloromethane, washed with sat. aq. sodium hydrogencarbonate solution, dried ($Na_2SO_4$) and concentrated. Purification by flash column chromatography (ethyl acetate/heptane 1:4) afforded the titled product as a crystalline solid (0.9 g, 43%). MS (ISP)=204.3 ($M+H^+$).

d) (3S,5S)-5-Methyl-piperidin-3-ol; hydrochloride

To a solution of (S)-1-benzyl-5-methyl-piperidin-3-one (0.9 g, 4 mmol) was dissolved in methanol, 25% aq. hydrochloric acid solution added until the pH was acidic, followed by palladium (10% on activated charcoal, 0.2 g). The mixture was stirred under 1 atmosphere of hydrogen (balloon) for 6 h. The reaction was then filtered through Hyflo and concentrated to afford the title product as a white powder (0.66 g, quantitative). MS (ISP)=116.1 ($M+H^+$).

Intermediate 5

(R,S)-4-((S)-4-Hydroxy-6-aza-spiro[2.5]oct-6-yl)-2-(7-oxo-[1,4]diazepan-1-yl)-butyric acid methyl ester; dihydrochloride

A) (rac)-4-[3-(tert-Butyl-dimethyl-silanyloxy)-1-methoxycarbonyl-propyl]-5-oxo-[1,4]diazepane-1-carboxylic acid benzyl ester A solution of 6.95 g (28.0 mmol) of 5-oxo-[1,4]diazepane-1-carboxylic acid benzyl ester in 85 ml of N,N-dimethylformamide was treated at 0° C. with 1.47 g (33.6 mmol) of NaH (55% in oil) in three portions. After 30 min, 10.0 g (28.0 mmol) of (rac)-4-(tert-butyl-dimethyl-silanyloxy)-2-iodo-butyric acid methyl ester (intermediate 1) were added during 5 min. The solution was stirred 2¼ h at 0° C. and neutralized with cold 10% aq. potassium hydrogensulfate solution and extracted with diethyl ether (3×). The organic phases were washed with sat. aq. sodium hydrogencarbonate solution, 10% aq. sodium chloride solution, dried over $Na_2SO_4$ evaporated and purified by flash silica gel column (n-heptane/ethyl acetate 4:1 to 2:1) to yield 8.45 g (63%) of the title compound as yellow viscous oil. MS: 479.2 ($MH^+$).

B) (rac)-4-(3-Hydroxy-1-methoxycarbonyl-propyl)-5-oxo-[1,4]diazepane-1-carboxylic acid benzyl ester A solution of 1.53 g (3.20 mmol) of (rac)-4-[3-(tert-butyl-dimethyl-silanyloxy)-1-methoxycarbonyl-propyl]-5-oxo-[1, 4]diazepane-1-carboxylic acid benzyl ester (evaporated twice with toluene) in 25 ml of dichloromethane was treated at 0° C. with 3.20 ml (3.20 mmol, 1 M in dichloromethane) of boron trichloride and kept 1 h at this temperature. The solution was stirred 17 h at room temperature and then extracted with cold sat. aq. sodium hydrogencarbonate solution and ethyl acetate (3×). The organic phases were washed with sat. aq. sodium hydrogencarbonate solution, 10% aq. sodium chloride solution, dried over $Na_2SO_4$ evaporated to give 1.34 g (quantitative) of the title compound as yellow viscous oil. MS: 365.1 ($MH^+$).

C) (rac)-4-(1-Methoxycarbonyl-3-oxo-propyl)-5-oxo-[1,4]diazepane-1-carboxylic acid benzyl ester To a solution of 0.31 ml (3.60 mmol) of oxalyl chloride in 7.7 ml dichloromethane at −50 to −60° C. was added a solution of 0.53 ml (7.51 mmol) dimethylsulfoxide in 1.6 ml of dichloromethane within 10 min. The solution was stirred for 5 min and a solution of 1.14 (3.13 mmol) (rac)-4-(3-hydroxy-1-methoxycarbonyl-propyl)-5-oxo-[1,4]diazepane-1-carboxylic acid benzyl ester in 6.8 ml dichloromethane was added within 10 min. The mixture was stirred for 15 min and 2.18 ml (15.64 mmol) of triethylamine were added within 20 min. The suspension was stirred for 1¼ h and slowly warmed to 0° C. The reaction was neutralized with cold 10% aq. potassium dihydrogenphosphate solution (adjusted with 10% aq. potassium hydrogensulfate solution to pH 4-5) and extracted with diethyl ether (3x). The organic phases were washed with 10% aq. potassium dihydrogenphosphate solution, sat. aq. sodium hydrogencarbonate solution, 10% aq. sodium chloride solution, dried over $Na_2SO_4$ evaporated to yield 1.25 g (quantitative) of the title compound as yellow oil. MS: 363.2 ($MH^+$).

D) (R,S)-4-[3-((S)-4-Hydroxy-6-aza-spiro[2.5]oct-6-yl)-1-methoxycarbonyl-propyl]-5-oxo-[1,4]diazepane-1-carboxylic acid benzyl ester 1.09 g (3.01 mmol) of (rac)-4-(1-methoxycarbonyl-3-oxo-propyl)-5-oxo-[1,4]diazepane-1-carboxylic acid benzyl ester and 0.59 g (3.61 mmol) of (S)-6-aza-spiro[2.5]octan-4-ol; hydrochloride (intermediate 2) were dissolved in 1,2-dichloroethane/ethanol 1:1 (22 ml) and treated with 0.50 ml (3.61 mmol) of triethylamine, 0.79 ml of acetic acid and 0.79 ml (6.32 mmol, 8 M in pyridine) of pyridine-borane complex (cooling with a water bath to room temperature). The reaction was stirred at room temperature over 1¾ h, then partitioned between cold sat. aq. sodium hydrogencarbonate solution and ethyl acetate (3x). The organic phases were washed with sat. aq. sodium hydrogencarbonate solution, 10% aq. sodium chloride solution, dried over $Na_2SO_4$ evaporated and purified by flash silica gel column (dichloromethane/methanol 96:4 to 9:1) to yield 1.11 g (78%) of the title compound as light yellow foam. MS: 474.3 ($MH^+$).

E) (R,S)-4-((S)-4-Hydroxy-6-aza-spiro[2.5]oct-6-yl)-2-(7-oxo-[1,4]diazepan-1-yl)-butyric acid methyl ester; dihydrochloride A solution of 0.99 g (2.08 mmol) (R,S)-4-[3-((S)-4-hydroxy-6-aza-spiro[2.5]oct-6-yl)-1-methoxycarbonyl-propyl]-5-oxo-[1,4]diazepane-1-carboxylic acid benzyl ester in 30 ml of methanol was treated with a solution of 4.16 ml of 1 M aq. hydrochloric acid solution and 0.099 g of Pd/C (10%) and was stirred over $H_2$-atmosphere for 30 min. After filtration, the solution was evaporated, dissolved in dichloromethane/methanol, dried with $Na_2SO_4$, filtered and evaporated again under reduced pressure to yield 1.00 g (quantitative) of the title compound as a white powder. MS: 340.2 ($MH^+$).

Intermediate 6

(R,S)-4-[3-((S)-4-Hydroxy-6-aza-spiro[2.5]oct-6-yl)-1-methoxymethyl-propyl]-[1,4]diazepan-5-one

A) (rac)-4-[3-(tert-Butyl-dimethyl-silanyloxy)-1-hydroxymethyl-propyl]-5-oxo-[1,4]diazepane-1-carboxylic acid benzyl ester A solution of 1.53 g (3.20 mmol) of (rac)-4-[3-(tert-butyl-dimethyl-silanyloxy)-1-methoxycarbonyl-propyl]-5-oxo-[1,4]diazepane-1-carboxylic acid benzyl ester (intermediate 5A) in 32 ml of ethanol was treated at 0° C. with 0.14 g (6.40 mmol) of lithium borohydride. The reaction was stirred 10 min at 0° C. and 1.5 h at room temperature, then neutralized with cold 10% aq. potassium hydrogensulfate solution and extracted with diethyl ether (3x). The organic phases were washed with 10% aq. potassium hydrogensulfate solution, 10% aq. sodium chloride solution, dried over $Na_2SO_4$ evaporated to yield 1.29 g (89%) of the title compound as light yellow viscous oil. MS: 451.2 ($MH^+$).

B) (rac)-4-[3-(tert-Butyl-dimethyl-silanyloxy)-1-methoxymethyl-propyl]-5-oxo-[1,4]diazepane-1-carboxylic acid benzyl ester 1.37 g (3.04 mmol) of the above prepared (rac)-4-[3-(tert-butyl-dimethyl-silanyloxy)-1-hydroxymethyl-propyl]-5-oxo-[1,4]diazepane-1-carboxylic acid benzyl ester and 0.95 ml (15.20 mmol) of methyl iodide were dissolved in 4.8 ml of N,N-dimethylformamide. After cooling (0° C.), 0.16 g (3.65 mmol) of NaH (55% in oil) was added. The reaction was stirred for 3 h at this temperature, then poured onto crushed ice/10% aq. potassium hydrogensulfate solution and extracted with diethyl ether (3x). The organic layers were washed with 10% aq. potassium hydrogensulfate solution and 10% aq. sodium chloride solution, dried over $Na_2SO_4$ and evaporated to dryness to yield 1.36 g (96%) of the title compound as light yellow oil. MS: 465.3 ($MH^+$).

C) (rac)-4-(3-Hydroxy-1-methoxymethyl-propyl)-5-oxo-[1,4]diazepane-1-carboxylic acid benzyl ester 3.22 ml (3.22 mmol, 1 M in tetrahydrofuran) tetrabutylammonium fluoride were added to a cooled solution (0° C.) of 1.36 g (2.93 mmol) (rac)-4-[3-(tert-butyl-dimethyl-silanyloxy)-1-methoxymethyl-propyl]-5-oxo-[1,4]diazepane-1-carboxylic acid benzyl ester in 29 ml tetrahydrofuran. After 50 min water was added and extracted with ethyl acetate (3x). The organic phases were washed with water (2x), dried over $Na_2SO_4$ and evaporated. Flash chromatography on silica gel with a gradient 2% to 4% methanol in dichloromethane yielded 0.79 g (77%) of the title compound as a colorless oil, MS: 263 (M).

D) (rac)-4-(1-Methoxymethyl-3-oxo-propyl)-5-oxo-[1,4]diazepane-1-carboxylic acid benzyl ester In analogy to the procedure described for intermediate 5C, (rac)-4-(3-hydroxy-1-methoxymethyl-propyl)-5-oxo-[1,4]diazepane-1-carboxylic acid benzyl ester gave the title compound in 91% yield as light yellow oil. MS: 349.2 ($MH^+$).

E) (R,S)-4-[3-((S)-4-Hydroxy-6-aza-spiro[2.5]oct-6-yl)-1-methoxymethyl-propyl]-5-oxo-[1,4]diazepane-1-carboxylic acid benzyl ester In analogy to the procedure described for intermediate 5D, (rac)-4-(1-methoxymethyl-3-oxo-propyl)-5-oxo-[1,4]diazepane-1-carboxylic acid benzyl ester and (S)-6-aza-spiro[2.5]octan-4-ol; hydrochloride (intermediate 2) gave the title compound in 78% yield as colorless viscous oil. MS: 460.3 ($MH^+$).

F) (R,S)-4-[3-((S)-4-Hydroxy-6-aza-spiro[2.5]oct-6-yl)-1-methoxymethyl-propyl]-[1,4]diazepan-5-one In analogy to the procedure described for intermediate 5E, (R,S)-4-[3-((S)-4-hydroxy-6-aza-spiro[2.5]oct-6-yl)-1-methoxymethyl-propyl]-5-oxo-[1,4]diazepane-1-carboxylic acid benzyl ester in methanol with only 0.1 eq. of aq. 1 M hydrochloric acid solution, gave the title compound in 98% yield as colorless viscous oil. MS: 326.3 (MH$^+$).

Intermediate 7

(S)-2-Amino-4-benzyloxy-butyric acid methyl ester; hydrochloride 15.5 ml of acetyl chloride was added dropwise to 95 ml of methanol cooled in ice. The solution was stirred for 5 min and 15.47 g (73.91 mmol) O-benzyl-L-homoserine was added in one portion (in analogy to Synthesis 1997, 1146). The mixture was stirred at room temperature for 1 h, and warmed for 2½ h at reflux. The solution was cooled and the solvent removed by evaporation under reduced pressure. The residue was dissolved in dichloromethane and evaporated and dried under reduced pressure overnight to give 19.4 g (quantitative) of the title compound as white solid. MS: 224.1 (MH$^+$).

Intermediate 8

(S)-4-((S)-4-Hydroxy-6-aza-spiro[2.5]oct-6-yl)-2-(7-oxo-[1,4]diazepan-1-yl)-butyric acid methyl ester; dihydrochloride A) 3-[Benzyloxycarbonyl-(2-hydroxy-ethyl)-amino]-propionic acid tert-butyl ester 6.11 g (100 mmol) of ethanolamine were cooled (0° C.), treated with 14.52 ml (100 mmol) of ter-butyl-acrylate and stirred 15 min at this temperature. During warming up to room temperature the reaction started and was kept with cooling at 25-30° C. and then stirred 18 h at room temperature. The oil was dissolved in 500 ml of tetrahydrofuran and 500 ml of water, 27.42 (110 mmol) of N-(benzyloxycarbonyloxy)succinimide were added at 0° C. followed by 27.88 ml (200 mmol) of triethlamine. The reaction was stirred at room temperature over 3 h, then partitioned between 10% aq. potassium hydrogensulfate solution and diethyl ether (3×). The organic phases were washed with 10% aq. potassium hydrogensulfate solution, sat. aq. sodium hydrogencarbonate solution, 10% aq. sodium chloride solution, dried over Na$_2$SO$_4$ evaporated and purified by flash silica gel column (n-heptane/ethyl acetate 4:1 to 1:1) to yield 27.53 g (85%) of the title compound as light yellow oil. MS: 324.2 (MH$^+$).

B) 3-[Benzyloxycarbonyl-(2-oxo-ethyl)-amino]-propionic acid tert-butyl ester

To a solution of 4.53 ml (35.65 mmol) of oxalyl chloride in 76 ml dichloromethane at −50 to −60° C. was added a solution of 5.81 ml (74.40 mmol) dimethylsulfoxide in 16 ml of dichloromethane within 20 min. The solution was stirred for 5 min and a solution of 10.03 g (31.0 mmol) 3-[benzyloxycarbonyl-(2-hydroxy-ethyl)-amino]-propionic acid tert-butyl ester in 67 ml dichloromethane was added within 20 min. The mixture was stirred for 15 min and 21.6 ml (155 mmol) of triethylamine were added within 25 min. The suspension was stirred for 2 h and slowly warmed to 0° C. The reaction was neutralized with cold 10% aq. potassium dihydrogenphosphate solution (adjusted with solid potassium dihydrogenphosphate to pH 4-5) and extracted with diethyl ether (3×). The organic phases were washed with 10% aq. potassium dihydrogenphosphate solution, sat. aq. sodium hydrogencarbonate solution, 10% aq. sodium chloride solution, dried over Na$_2$SO$_4$ evaporated to yield 9.94 g (99.8%) of the title compound as yellow oil. MS: 322.1 (MH$^+$).

C) (S)-4-Benzyloxy-2-{2-[benzyloxycarbonyl-(2-tert-butoxycarbonyl-ethyl)-amino]-ethylamino}-butyric acid methyl ester 3.71 g (11.55 mmol) of 3-[benzyloxycarbonyl-(2-oxo-ethyl)-amino]-propionic acid tert-butyl ester and 3.00 g (11.55 mmol) of (S)-2-amino-4-benzyloxy-butyric acid methyl ester; hydrochloride (intermediate 7) were dissolved in 1,2-dichloroethane/ethanol 1:1 80 ml) and treated with 1.93 ml (13.86 mmol) of triethylamine, 3.03 ml of acetic acid and 3.03 ml (24.25 mmol, 8 M in pyridine) of pyridine-borane complex (cooling with a water bath to room temperature). The reaction was stirred at room temperature over 1¼ h, then partitioned between aq. sodium hydrogencarbonate solution and diethyl ether (3×). The organic phases were washed with sat. aq. sodium hydrogencarbonate solution, 10% aq. sodium chloride solution, dried over Na$_2$SO$_4$ evaporated and purified by flash silica gel column (dichloromethane/n-heptane 1:1 to dichloromethane, then dichloromethane/ethyl acetate 4:1 to ethyl acetate) to yield 4.81 g (79%) of the title compound as colorless oil. MS: 529.2 (MH$^+$).

D) (S)-4-Benzyloxy-2-{2-[benzyloxycarbonyl-(2-carboxy-ethyl)-amino]-ethylamino}-butyric acid methyl ester; hydrochloride A solution of 4.58 g (8.66 mmol) of (S)-4-benzyloxy-2-{2-[benzyloxycarbonyl-(2-tert-butoxycarbonyl-ethyl)-amino]-ethylamino}-butyric acid methyl ester in 17 ml of dioxane was cooled (10° C.), treated with 21.7 ml (86.7 mmol) of 4 M hydrogen chloride solution in dioxane, 10 drops of water and stirred at room temperature for 12 h. The solution was evaporated, suspended in acetonitrile and evaporated (2×), dissolved in dichloromethane, treated with Na$_2$SO$_4$, filtered and evaporated to yield 4.42 g (quantitative) of the title compound as light yellow foam. MS: 471.2 (M−H$^−$).

E) 4-((S)-3-Benzyloxy-1-methoxycarbonyl-propyl)-5-oxo-[1,4]diazepane-1-carboxylic acid benzyl ester A solution of 4.40 g (8.64 mmol) of (S)-4-benzyloxy-2-{2-[benzyloxycarbonyl-(2-carboxy-ethyl)-amino]-ethylamino}-butyric acid methyl ester; hydrochloride in 85 ml dichloromethane was treated with 1.20 (8.64 mmol) of triethylamine and at 0° C. with 1.99 g (10.37 mmol) of N-(3-dimethylaminopropyl)-N'-ethylcarbodiimide hydrochloride. The cooling bath was allowed to come to room temperature and after 15 h the reaction was extracted with 10% aq. potassium hydrogensulfate solution/diethyl ether (3×). The organic phases were washed with 10% aq. potassium hydrogensulfate solution, 10% sodium chloride solution and dried over Na$_2$SO$_4$ to yield after evaporation of the solvent 3.74 g (95%) of the title compound as a light yellow oil. MS: 455.2 (MH$^+$).

F) 4-((S)-3-Hydroxy-1-methoxycarbonyl-propyl)-5-oxo-[1,4]diazepane-1-carboxylic acid benzyl ester A solution of 0.50 g (1.10 mmol) of 4-((S)-3-benzyloxy-1-methoxycarbonyl-propyl)-5-oxo-[1,4]diazepane-1-carboxylic acid benzyl ester (evaporated twice with toluene) in 9 ml dichloromethane was treated with 1.10 ml (1.10 mmol, 1 M in dichloromethane) of boron trichloride. The solution was stirred 6.5 h at room temperature, cooled (0° C.) and treated with 0.99 ml (0.90 mmol, 1 M in dichloromethane) of boron trichloride, after 15 h at room temperature, additional 0.28 ml (0.28 mmol, 1 M in dichloromethane) of boron trichloride were added to the cooled (0° C.) reaction. After 24 h at room temperature, the mixture was extracted with cold sat. aq. sodium hydrogencarbonate solution and ethyl acetate (3×). The organic phases were washed with sat. aq. sodium hydrogencarbonate solution, 10% aq. sodium chloride solution, dried over $Na_2SO_4$ evaporated to give 0.298 g (75%) of the title compound as light yellow oil. MS: 365.0 ($MH^+$).

G) 4-((S)-1-Methoxycarbonyl-3-oxo-propyl)-5-oxo-[1,4]diazepane-1-carboxylic acid benzyl ester In analogy to the procedure described for intermediate 5C, 4-((S)-3-hydroxy-1-methoxy-carbonyl-propyl)-5-oxo-[1,4] diazepane-1-carboxylic acid benzyl ester gave the title compound in 83% yield as yellow oil. MS: 362.9 ($MH^+$).

H) 4-[(S)-3-((S)-4-Hydroxy-6-aza-spiro[2.5]oct-6-yl)-1-methoxycarbonyl-propyl]-5-oxo-[1,4]diazepane-1-carboxylic acid benzyl ester In analogy to the procedure described for intermediate 5D, 4-((S)-1-methoxycarbonyl-3-oxo-propyl)-5-oxo-[1,4]diazepane-1-carboxylic acid benzyl ester and (S)-6-aza-spiro [2.5]octan-4-ol; hydrochloride (intermediate 2) gave the title compound in 51% yield as light yellow foam. MS: 474.3 ($MH^+$).

I) (S)-4-((S)-4-Hydroxy-6-aza-spiro[2.5]oct-6-yl)-2-(7-oxo-[1,4]diazepan-1-yl)-butyric acid methyl ester: dihydrochloride In analogy to the procedure described for intermediate 5E, 4-[(S)-3-((S)-4-hydroxy-6-aza-spiro[2.5]oct-6-yl)-1-methoxycarbonyl-propyl]-5-oxo-[1,4]diazepane-1-carboxylic acid benzyl ester gave the title compound in quantitative yield as white powder. MS: 340.2 ($MH^+$).

Intermediate 9

Imidazole-1-carboxylic acid 3,4-dichloro-phenyl ester

A solution of 5.00 g (30.7 mmol) of 3,4-dichlorophenol in 160 ml of dichloromethane was treated with 6.47 g (39.9 mmol) of 1,1'-carbonyldiimidazol. The reaction was stirred at room temperature over 3.5 h, then partitioned between aq. 0.5 M citric acid and dichloromethane (3×). The organic phase was dried over $Na_2SO_4$ evaporated and crystallized from diethyl ether to yield 5.03 g (64%) of the title compound as white crystals. MS: 256.8 ($MH^+$, 2Cl).

Intermediate 10

4-(3-Piperidin-1-yl-propyl)-[1,4]diazepan-5-one; dihydrochloride

A) 5-Oxo-4-(3-piperidin-1-yl-propyl)-[1,4]diazepane-1-carboxylic acid tert-butyl ester A solution of 8.52 g (39.75 mmol) of 5-oxo-[1,4]diazepane-1-carboxylic acid tert-butyl ester in 200 ml of N,N-dimethylacetamide was treated at 0° C. with 2.60 g (59.62 mmol) of NaH (55% in oil) in small portions. The reaction was stirred 1 h at this temperature, then the free 1-(3-chloropropyl)piperidine in 200 ml toluene was dropped in [49.6 g (250 mmol, 6.3 eq.) 1-(3-chloropropyl)piperidine hydrochloride were dissolved in 262 ml of 1 M aq. sodium hydroxide solution and extracted with toluene (200 ml). The organic phase was dried over $Na_2SO_4$]. The reaction was warmed up to room temperature and stirred over night. After 2 h at 50° C. and cooling to room temperature, the reaction was neutralized with water (50 ml), evaporated and then dissolved in sat. aq. sodium hydrogencarbonate solution/diethyl ether. After reextraction with diethyl ether, the organic phase was dried ($Na_2SO_4$), evaporated and crystallized from pentane to yield 12.08 g (90%) of the title compound as white crystals. MS: 340.2 ($MH^+$).

B) 4-(3-Piperidin-1-yl-propyl)-[1,4]diazepan-5-one: dihydrochloride

A solution of 7.3 g (21.50 mmol) of 5-oxo-4-(3-piperidin-1-yl-propyl)-[1,4]diazepane-1-carboxylic acid tert-butyl ester was dissolved in 140 ml dichloromethane, cooled to 0° C. and treated with 54 ml (215.03 mmol) of 4 M hydrogen chloride solution in dioxane, then warmed to room temperature. After 3 h, 40 ml of methanol were added to dissolve the precipitation and stirring was continued over night. The solution was evaporated, dissolved in toluene and evaporated (2×) to yield 7.71 g (quantitative) of the title compound as a white solid. MS: 240.1 ($MH^+$).

Intermediate 11

4-(2-Pyrrolidin-1-yl-ethyl)-[1,4]di-azepan-5-one; dihydrochloride

A) 5-Oxo-4-(2-pyrrolidin-1-yl-ethyl)-[1,4]diazepane-1-carboxylic acid tert-butyl ester In analogy to the procedure described in intermediate 10A, 5-oxo-[1,4]diazepane-1-carboxylic acid tert-butyl ester and 1-(2-chloro-ethyl)-pyrrolidine gave the title compound as light yellow solid. MS: 312.0 ($MH^+$).

B) 4-(2-Pyrrolidin-1-yl-ethyl)-[1,4]di-azepan-5-one; dihydrochloride

In analogy to the procedure described in intermediate 10B, 5-oxo-4-(2-pyrrolidin-1-yl-ethyl)-[1,4]diazepane-1-carboxylic acid tert-butyl ester gave the title compound as off-white powder. MS: 212.1 ($MH^+$).

Intermediate 12

1-(2-Pyrrolidin-1-yl-ethyl)-piperazin-2-one-dihydrochloride

A) 3-Oxo-4-(2-pyrrolidin-1-yl-ethyl)-piperazine-1-carboxylic acid tert-butyl ester Sodium hydride (55% dispersion in mineral oil, 1.96 g, 45 mmol) was added portionwise at room temperature to a solution of 3-oxo-piperazine-1-carboxylic acid tert-butyl ester (6.01 g, 30.0 mmol) in N,N-dimethylacetamide (150 ml), then a solution of 1-(2-chloroethyl)-pyrrolidine in toluene [prepared from commercially available 1-(2-chloroethyl)-pyrrolidine hydrochloride (16.1 g, 94.5 mmol) by partitioning between toluene (70 ml) and 1 M aq. sodium hydroxide solution (70 ml) and drying of the organic layer with $Na_2SO_4$] was added dropwise. The reaction mixture was stirred at room temperature for 16 h, then heated at 75° C. for 80 min. After cooling, the reaction mixture was partitioned between diethyl ether and sat. aq. sodium hydrogen-carbonate solution. The organic layer was dried (Na$_2$SO$_4$) and evaporated. Crystallization of the residue from diethyl ether afforded the title compound (3.74 g, 42%). White solid, MS (ISP)=298.2 (M+H)$^+$.

B) 1-(2-Pyrrolidin-1-yl-ethyl)-piperazin-2-one-dihydrochloride

In analogy to the procedure described in intermediate 10B, 3-oxo-4-(2-pyrrolidin-1-yl-ethyl)-piperazine-1-carboxylic acid tert-butyl ester gave the title compound as off-white powder. MS: 198.0 (MH$^+$).

Intermediate 13

2-(3-Piperidin-1-yl-propyl)-[1,2,5]thiadiazepane 1,1-dioxide dihydrochloride

The title compound, m/e=276.2 (M+H)$^+$, was produced in analogy with intermediate 10, steps A and B. Thus, 1,1-dioxo-[1,2,5]thiadiazepane-5-carboxylic acid tert-butyl ester (U.S. Pat. No. 6,921,759) was alkylated in step A with 1-(3-chloropropyl)piperidine, leading to 1,1-dioxo-2-(3-piperidin-1-yl-propyl)-[1,2,5]thiadiazepane-5-carboxylic acid tert-butyl ester, which was deprotected in step B.

Intermediate 14

6-Methyl-4-(3-piperidin-1-yl-propyl)-[1,4]diazepan-5-one; dihydrochloride

A) 3-[tert-Butoxycarbonyl-(2-hydroxy-ethyl)-amino]-2-methyl-propionic acid ethyl ester The title compound was produced in analogy with intermediate 15A from ethyl methacrylate, ethanolamine, and di-tert-butyl-dicarbonate. Yellow oil, MS (ISP)=276.3 (M+H)$^+$.

B) 6-Methyl-5-oxo-[1,4]diazepane-1-carboxylic acid tert-butyl ester

The title compound was produced in analogy with intermediate 15B from 3-[tert-butoxycarbonyl-(2-hydroxy-ethyl)-amino]-2-methyl-propionic acid ethyl ester. White solid, MS (ISP)=229.4 (M+H)$^+$.

C) 6-Methyl-5-oxo-4-(3-piperidin-1-yl-propyl)-[1,4]diazepane-1-carboxylic acid tert-butyl ester The title compound was produced in analogy with intermediate 10A from 6-methyl-5-oxo-[1,4]diazepane-1-carboxylic acid tert-butyl ester and 1-(3-chloropropyl)piperidine. Colorless oil, MS (ISP)=354.3 (M+H)$^+$.

D) 6-Methyl-4-(3-piperidin-1-yl-propyl)-[1,4]diazepan-5-one; dihydrochloride

The title compound was produced in analogy with intermediate 10B from 6-methyl-5-oxo-4-(3-piperidin-1-yl-propyl)-[1,4]diazepane-1-carboxylic acid tert-butyl ester. White foam, MS (ISP)=254.2 (M+H)$^+$.

Intermediate 15

(R)-2-Methyl-4-(3-piperidin-1-yl-propyl)-[1,4]diazepan-5-one; dihydrochloride

A) 3-[tert-Butoxycarbonyl-((R)-2-hydroxy-1-methyl-ethyl)-amino]-propionic acid ethyl ester At 0° C. ethyl acrylate (1.33 g, 13.3 mmol) was added to D-alaninol (1.00 g, 13.3 mmol). The homogeneous solution was stirred at room temperature for 16 h, then dichloromethane (20 ml) and di-tert-butyl-dicarbonate (3.20 g, 14.7 mmol) were added, then after 4 h the solution was evaporated. Chromatography (SiO$_2$; heptane/ethyl acetate gradient) produced the title compound (3.50 g, 95%). Colorless liquid, MS (ISP)=276.2 (M+H)$^+$.

B) (R)-2-Methyl-5-oxo-[1,4]diazepane-1-carboxylic acid tert-butyl ester

Triphenylphosphine (12.0 g, 45.9 mmol) and diisopropyl azodicarboxylate (9.88 g, 45.9 mmol) were added at room temperature to a solution of 3-[tert-butoxycarbonyl-((R)-2-hydroxy-1-methyl-ethyl)-amino]-propionic acid ethyl ester in tetrahydrofuran (600 ml), then after 2 min diphenylphorphoryl azide (12.6 g, 45.9 mmol) was added. After 16 h the reaction mixture was concentrated and the residue purified by chromatography (SiO$_2$; heptane-ethyl acetate gradient) to afford slightly impure 3-[tert-butoxycarbonyl-((R)-2-azido-1-methyl-ethyl)-amino]-propionic acid ethyl ester (8.82 g). This was dissolved in methanol (880 ml), then after addition of palladium (10% on activated charcoal, 1.6 g) and potassium carbonate (42.6 g, 308 mmol) the reaction mixture was hydrogenated at room temperature and atmospheric pressure for 16 h. Insoluble material was removed by filtration and the filtrate concentrated. Chromatography (SiO$_2$; heptane/ethyl acetate 1:1, then dichloromethane/methanol/25% aq. ammonia solution 97.5:2.5:0.25) produced the title compound (2.20 g, 21%). White solid, MS (ISP)=229.4 (M+H)$^+$.

C) (R)-2-Methyl-5-oxo-4-(3-piperidin-1-yl-propyl)-[1,4]diazepane-1-carboxylic acid tert-butyl ester The title compound was produced in analogy with intermediate 10A from (R)-2-methyl-5-oxo-[1,4]diazepane-1-carboxylic acid tert-butyl ester and 1-(3-chloropropyl)piperidine. Colorless oil, MS (ISP)=354.3 (M+H)$^+$.

D) (R)-2-Methyl-4-(3-piperidin-1-yl-propyl)-[1,4]diazepan-5-one; dihydrochloride The title compound was produced in analogy with intermediate 10B from (R)-2-methyl-5-oxo-4-(3-piperidin-1-yl-propyl)-[1,4]diazepane-1-carboxylic acid tert-butyl ester. Light yellow solid, White solid, MS (ISP)=254.2 (M+H)$^+$.

Intermediate 16

(R)-2-Benzyl-5-oxo-4-(3-piperidin-1-yl-propyl)-[1,4]diazepane-1-carboxylic acid tert-butyl ester A) (2-Benzyloxycarbamoyl-ethyl)-((R)-1-hydroxymethyl-2-phenyl-ethyl)-carbamic acid tert-butyl ester D-Phenylalaninol (880 mg, 5.64 mmol) was added at room temperature to a solution of N-benzyloxy-acrylamide (*Tetrahedron Letters* 1994, 35, 5157; 1.00 g, 5.64 mmol) in methanol (2 ml). The homogeneous solution was stirred for 5 days at room temperature, then heated at 50° C. for 2 h. After evaporation of volatile material the residue was taken up in dichloromethane (30 ml), then after addition of di-tert-butyl-dicarbonate (1.36 g, 6.21 mmol) the reaction mixture was stirred at room temperature for 16 h. After concentration, the residue was purified by chromatography (SiO$_2$; heptane-ethyl acetate gradient) to afford the title compound (1.24 g, 51%). Colorless oil, MS (ISP)=429.3 (M+H)$^+$.

B) (R)-2-Benzyl-4-benzyloxy-5-oxo-[1,4]diazepane-1-carboxylic acid tert-butyl ester Diisopropyl azodicarboxylate (806 mg, 3.75 mmol) was added at <10° C. to a solution of triphenylphosphine (983 mg, 3.75 mmol) in tetrahydrofuran (60 ml), followed by addition of a solution of (2-benzyloxycarbamoyl-ethyl)-((R)-1-hydroxymethyl-2-phenyl-ethyl)-carbamic acid tert-butyl ester (1.24 g, 2.88 mmol) in tetrahydrofuran (12 ml). The reaction mixture was stirred at <10° C. for 16 h, then concentrated. The residue was purified by chromatography (SiO$_2$; heptane/ethyl acetate 7:3) to afford the title compound (800 mg, 68%). Light yellow oil, MS (ISP)=411.3 (M+H)$^+$.

C) (R)-2-Benzyl-5-oxo-[1,4]diazepane-1-carboxylic acid tert-butyl ester (R)-2-Benzyl-4-benzyloxy-5-oxo-[1,4]diazepane-1-carboxylic acid tert-butyl ester (795 mg, 1.94 mmol) was dissolved in methanol (21 ml) and stirred for 16 h at 70° C. under a hydrogen pressure of 8 bar. After cooling insoluble material was removed by filtration and the filtrate concentrated, to afford the title compound (486 mg, 82%). White foam, MS (ISP)=305.3 (M+H)$^+$.

D) (R)-2-Benzyl-5-oxo-4-(3-piperidin-1-yl-propyl)-[1,4]diazepane-1-carboxylic acid tert-butyl ester The title compound was produced in analogy with intermediate 10A from (R)-2-benzyl-5-oxo-[1,4]diazepane-1-carboxylic acid tert-butyl ester and 1-(3-chloropropyl)piperidine. Light yellow oil, MS (ISP)=430.4 (M+H)$^+$.

Intermediate 17

(R)-5-Oxo-4-(3-piperidin-1-yl-propyl)-2-(3-trifluoromethyl-benzyl)-[1,4]diazepane-1-carboxylic acid tert-butyl ester A) (R)-2-Amino-3-(3-trifluoromethyl-phenyl)-propan-1-ol Borane-tetrahydrofuran complex (1 M in tetrahydrofuran, 21.4 ml, 21.4 mmol) was added at 0° C. to a solution of D-3-trifluoromethylphenylalanine (2.00 g, 8.57 mmol) in tetrahydrofuran (45 ml). The reaction mixture was allowed to reach room temperature over 3 h, then partitioned between sat. aq. sodium carbonate solution and ethyl acetate. The organic layer was washed with brine, dried (MgSO$_4$), filtered, and evaporated. Chromatography (SiO$_2$; dichloromethane/methanol/25% aq. ammonia solution 90:10:0.25) afforded the title compound (1.58 g, 84%). Colorless oil, MS (ISP)=220.3 (M+H)$^+$.

B) (2-Benzyloxycarbamoyl-ethyl)-[(R)-1-hydroxymethyl-2-(3-trifluoromethyl-phenyl)-ethyl]-carbamic acid tert-butyl ester The title compound was produced in analogy with intermediate 16A from (R)-2-amino-3-(3-trifluoromethyl-phenyl)-propan-1-ol and N-benzyloxyacrylamide. White foam, MS (ISP)=497.4 (M+H)$^+$.

C) (R)-4-Benzyloxy-5-oxo-2-(3-trifluoromethyl-benzyl)-[1,4]diazepane-1-carboxylic acid tert-butyl ester The title compound was produced in analogy with intermediate 16B from (2-benzyloxy-carbamoyl-ethyl)-[(R)-1-hydroxymethyl-2-(3-trifluoromethyl-phenyl)-ethyl]-carbamic acid tert-butyl ester. Light yellow gum, MS (ISP)=479.1 (M+H)$^+$.

D) (R)-5-Oxo-2-(3-trifluoromethyl-benzyl)-[1.4]diazepane-1-carboxylic acid tert-butyl ester The title compound was produced in analogy with intermediate 16C from (R)-4-benzyloxy-5-oxo-2-(3-trifluoromethyl-benzyl)-[1,4]diazepane-1-carboxylic acid tert-butyl ester. Off-white foam, MS (ISP)=373.3 (M+H)$^+$.

E) (R)-5-Oxo-4-(3-piperidin-1-yl-propyl)-2-(3-trifluoromethyl-benzyl)-[1,4]diazepane-1-carboxylic acid tert-butyl ester The title compound was produced in analogy with intermediate 10A from (R)-5-oxo-2-(3-trifluoromethyl-benzyl)-[1,4]diazepane-1-carboxylic acid tert-butyl ester and 1-(3-chloropropyl)piperidine. Colorless oil, MS (ISP)=520.0 (M+Na)$^+$.

Intermediate 18

(R)-5-Oxo-2-phenyl-4-(3-piperidin-1-yl-propyl)-[1,4]diazepane-1-carboxylic acid tert-butyl ester The title compound, m/e=416.4, was produced in analogy with intermediate 16, steps A to D. Thus, D-phenylglycinol was elaborated to (2-benzyloxycarbamoyl-ethyl)-((R)-2-hydroxy-1-phenyl-ethyl)-carbamic acid tert-butyl ester in step A, then cyclized in step B, leading to (R)-4-benzyloxy-5-oxo-2-phenyl-[1,4]diazepane-1-carboxylic acid tert-butyl ester. Hydrogenation in step C gave (R)-5-oxo-2-phenyl-[1,4]diazepane-1-carboxylic acid tert-butyl ester, which was alkylated with 1-(3-chloropropyl)piperidine in step D.

Intermediate 19

(R)-5-Oxo-2-phenethyl-4-(3-piperidin-1-yl-propyl)-[1,4]diazepane-1-carboxylic acid tert-butyl ester The title compound, m/e=444.3, was produced in analogy with intermediate 16, steps A to D. Thus, (R)-2-amino-4-phenylbutan-1-ol was elaborated to (2-benzyloxycarbamoyl-ethyl)-((R)-2-hydroxy-1-phenethyl-ethyl)-carbamic acid tert-butyl ester in step A, then cyclized in step B, leading to (R)-4-benzyloxy-5-oxo-2-phenethyl-[1,4]diazepane-1-carboxylic acid tert-butyl ester. Hydrogenation in step C gave (R)-5-oxo-2-phenethyl-[1,4]diazepane-1-carboxylic acid tert-butyl ester, which was alkylated with 1-(3-chloropropyl)piperidine in step D.

Intermediate 20

(S)-3-Methyl-1-(3-piperidin-1-yl-propyl)-piperazin-2-one

A) 2-(3-Benzyloxy-propylamino)-ethanol

Sodium iodide (1.67 g, 11.1 mmol) was added to a solution of benzyl 3-bromopropyl ether (26.0 g, 111 mmol) and ethanolamine (35.0 g, 556 mmol) in ethanol (250 ml). The reaction mixture was heated at reflux for 1 h, then cooled to room temperature and evaporated under vacuum. The residue was partitioned between sat. aq. ammonium chloride solution and ethyl acetate. The aqueous layer was basified with 40% aq. sodium hydroxide solution and extracted three times with ethyl acetate. The organic phases were pooled, dried (MgSO$_4$), filtered, and evaporated to afford the title compound (20.9 g, 90%). Light yellow liquid, MS (ISP)=210.2 (M+H)$^+$.

B) {(S)-1-[(3-Benzyloxy-propyl)-(2-hydroxy-ethyl)-carbamoyl]-ethyl}-carbamic acid tert-butyl ester A solution of N-(tert-butoxycarbonyl)-L-alanine (90 mg, 0.48 mmol), 2-(3-benzyloxy-propylamino)-ethanol (100 mg, 0.48 mg), N,N-diisopropylethylamine (185 mg, 1.43 mmol), 1-hydroxybenzotriazole (71 mg, 0.52 mmol), and N-ethyl-N'-(3-dimethylaminopropyl)-carbodiimide hydrochloride (101 mg, 0.52 mmol) in N,N-dimethylformamide (2 ml) was stirred at room temperature for 18 h, then partitioned between 1 M aq. hydrochloric acid solution and ethyl acetate. The organic layer was dried (MgSO$_4$), filtered, and evaporated. Chromatography (SiO$_2$; heptane-ethyl acetate gradient) produced the title compound (121 mg, 67%). Colorless oil, MS (ISP)=381.4 (M+H)$^+$.

C) (S)-1-(3-Benzyloxy-propyl)-3-methyl-piperazin-2-one

Dimethyl sulfoxide (7.60 g, 97.2 mmol) was added dropwise at −78° C. to a solution of oxalyl chloride (6.17 g, 48.6 mmol) in dichloromethane (300 ml) then after 10 min a solution of {(S)-1-[(3-benzyloxy-propyl)-(2-hydroxy-ethyl)-carbamoyl]-ethyl}-carbamic acid tert-butyl ester (16.8 g, 44.2 mmol) in dichloromethane (300 ml) was added at a temperature below −70° C. After 1 h, triethylamine (16.1 g, 159 mmol) was added, then after 15 min the ice bath was removed. The reaction mixture was allowed to reach room temperature, then washed with sat. aq. sodium hydrogencarbonate solution and brine, dried (MgSO$_4$), filtered, and evaporated. The residue was taken up in dichloromethane (300 ml), then triethylsilane (10.3 g, 88.4 mmol) and trifluoroacetic acid (75.6 g, 663 mmol) were added at room temperature. The reaction mixture was stirred at room temperature for 16 h, then evaporated. The residue was dissolved in dichloromethane (100 ml), then triethylamine (60 ml) was added at 0° C. over 30 min, then after 45 min the reaction mixture was concentrated. The residue was dissolved in ethyl acetate and water, then 2 M aq. sodium carbonate solution was added under ice cooling. The organic layer was separated, washed with brine, dried (MgSO$_4$), filtered, and evaporated. Chromatography (SiO$_2$; dichloromethane/methanol/25% aq. ammonia solution 90:10:0.25) produced the title compound (9.07 g, 78%). Colorless oil, MS (ISP)=263.4 (M+H)$^+$.

D) (S)-1-(3-Hydroxy-propyl)-3-methyl-piperazin-2-one

A solution of (S)-1-(3-benzyloxy-propyl)-3-methyl-piperazin-2-one (9.07 g, 34.6 mmol) in methanol (320 ml) was heated for 14 h at 70° C. under a hydrogen atmosphere (7 bar) in the presence of palladium (10% on activated charcoal, 7.36 g). After cooling, insoluble material was removed by filtration and the filtrate evaporated to produce the title compound (5.90 g, 99%). Colorless oil, MS (ISP)=173.1 (M+H)$^+$.

E) (S)-4-(3-Hydroxy-propyl)-2-methyl-3-oxo-piperazine-1-carboxylic acid tert-butyl ester Di-tert-butyl-dicarbonate (2.56 g, 11.6 mmol) was added to a solution of (S)-1-(3-hydroxy-propyl)-3-methyl-piperazin-2-one (2.00 g, 11.6 mmol) in dichloromethane (20 ml). The solution was stirred at room temperature for 72 h. After evaporation, the residue was chromatographed (SiO$_2$; dichloromethane/methanol/25% aq. ammonia solution 90:10:0.25) to afford the title compound (3.16 g, 100%). Colorless oil, MS (ISP)=273.3 (M+H)$^+$.

F) (S)-2-Methyl-3-oxo-4-(3-piperidin-1-yl-propyl)-piperazine-1-carboxylic acid tert-butyl ester Saturated aq. sodium hydrogencarbonate solution (1.25 ml) was added to a solution of (S)-4-(3-hydroxy-propyl)-2-methyl-3-oxo-piperazine-1-carboxylic acid tert-butyl ester (1.00 g, 3.67 mmol), potassium bromide (44 mg, 0.37 mmol), and 2,2,6,6-tetramethylpiperidin-1-oxyl (6 mg, 0.04 mmol) in dichloromethane (50 ml). Sodium hypochlorite solution (10% in water, 2.2 ml, 3.7 mmol) was added portionwise at 0° C., and the course of the oxidation was monitored by thin layer chromatography. After all starting material had reacted, the reaction mixture was washed with sat. aq. sodium hydrogencarbonate solution, and the aqueous layer was extracted twice with dichloromethane. The organic phases were pooled, dried (MgSO$_4$), filtered, and evaporated, thus affoding (S)-4-(3-oxo-propyl)-2-methyl-3-oxo-piperazine-1-carboxylic acid tert-butyl ester (950 mg). This was dissolved in dichloromethane (20 ml) and added over 20 min to a suspension of piperidine (297 mg, 3.49 mmol) triethylamine (353 mg, 3.49 mmol), acetic acid (419 mg, 6.98 mmol) and sodium triacetoxyborohydride (90% purity; 908 mg, 3.85 mmol) in dichloromethane (20 ml). After 16 h the reaction mixture was washed with 2 M aq. sodium carbonate solution, the organic layer was dried (MgSO$_4$), filtered, and evaporated. Chromatography (SiO$_2$; dichloromethane/methanol/25% aq. ammonia solution 90:10:0.25) produced the title compound (1.07 g, 86%). Light yellow oil, MS (ISP)=340.2 (M+H)$^+$.

G) (S)-3-Methyl-1-(3-piperidin-1-yl-propyl)-piperazin-2-one

A solution of (S)-2-methyl-3-oxo-4-(3-piperidin-1-yl-propyl)-piperazine-1-carboxylic acid tert-butyl ester (1.07 g, 3.15 mmol) in 1,4-dioxane (10 ml) was treated at room temperature with hydrogen chloride solution (4 M in 1,4-dioxane, 2.4 ml, 9.6 mmol), then after 4 h the reaction mixture was partitioned between 2 M aq. sodium carbonate solution and dichloromethane. The organic layer was washed with brine, dried (MgSO$_4$), filtered, and evaporated to afford the title compound (697 mg, 92%). Colorless gum, MS (ISP)=240.3 (M+H)$^+$.

Intermediate 21

(S)-4-(3-Hydroxy-propyl)-2-methyl-3-oxo-piperazine-1-carboxylic acid (3,4-dichloro-phenyl)-amide 3,4-Dichlorophenyl isocyanate (334 mg, 1.74 mmol) was added at 0° C. to a solution of (S)-1-(3-hydroxy-propyl)-3- methyl-piperazin-2-one (intermediate 20D; 300 mg, 1.74 mmol) in tetrahydrofuran (3 ml), then after 2.5 h the reaction mixture was evaporated. Chromatography (SiO$_2$; dichloromethane/methanol/25% aq. ammonia solution 90:10:0.25) produced the title compound (577 mg, 92%). White foam, MS (ISP)=360.1 (M+H)$^+$.

Intermediate 22

(S)-1-[3-((S)-4-Hydroxy-6-aza-spiro[2.5]oct-6-yl)-propyl]-3-methyl-piperazin-2-one A) (S)-4-(3-Hydroxy-propyl)-2-methyl-3-oxo-piperazine-1-carboxylic acid benzyl ester Sodium hydrogencarbonate (976 mg, 11.6 mmol) was added to a solution of (S)-1-(3-hydroxy-propyl)-3-methyl-piperazin-2-one (example 20D; 1.00 g, 5.81 mmol) in acetone (5 mL) and water (5 mL), then a solution of benzyl chloroformate (1.04 g, 5.81 mmol) in acetone (1 mL) was added at 0° C. The reaction mixture was allowed to reach room temperature over 16 h, then partitioned between ethyl acetate and water. The organic layer was dried (MgSO$_4$), filtered, and evaporated to afford the title compound (1.79 g), which was directly used in the next step.

B) (S)-4-[3-((S)-4-Hydroxy-6-aza-spiro[2.5]oct-6-yl)-propyl]-2-methyl-3-oxo-piperazine-1-carboxylic acid benzyl ester In analogy to the procedure described in intermediate 20F, the title compound was produced by oxidation of (S)-4-(3-hydroxy-propyl)-2-methyl-3-oxo-piperazine-1-carboxylic acid benzyl ester, followed by reductive amination of the aldehyde intermediate (S)-4-(3-oxo-propyl)-2-methyl-3-oxo-piperazine-1-carboxylic acid benzyl ester with (S)-6-aza-spiro[2.5]octan-4-ol hydrochloride (intermediate 2). Yellow gum, MS (ISP)=416.3 (M+H)$^+$.

C) (S)-1-[3-((S)-4-Hydroxy-6-aza-spiro[2.5]oct-6-yl)-propyl]-3-methyl-piperazin-2-one A solution of (S)-4-[3-((S)-4-hydroxy-6-aza-spiro[2.5]oct-6-yl)-propyl]-2-methyl-3-oxo-piperazine-1-carboxylic acid benzyl ester (950 mg, 2.29 mmol) in methanol (25 ml) was stirred for 5 h under a hydrogen atmosphere (1 bar) in the presence of palladium (10% on activated charcoal, 243 mg), then insoluble material was removed by filtration and the filtrate evaporated to produce the title compound (642 mg, 100%). Orange oil, MS (ISP)=282.3 (M+H)$^+$.

Intermediate 23

(S)-4-[(S)-3-((S)-4-Hydroxy-6-aza-spiro[2.5]oct-6-yl)-1-methoxymethyl-propyl]-2-methyl-3-oxo-piperazine-1-carboxylic acid tert-butyl ester A) (S)-2-amino-4-benzyloxy-butan-1-ol Borane-tetrahydrofuran complex (1 M in tetrahydrofuran, 60 mL, 60 mmol) was added at 0° C. to a suspension of O-benzyl-L-homoserine (5.06 g, 24.1 mmol) in tetrahydrofuran (100 mL). The ice bath was removed, and the reaction mixture was stirred for 72 h at room temperature, then the reaction was stopped by careful addition of methanol (40 mL). After evaporation of volatile material, the residue was taken up in 5% methanolic sulfuric acid solution (50 mL). The solution was heated at reflux for 2 h, then concentrated in vacuo. The residue was partitioned between ethyl acetate and 1 M aq. sodium hydroxide solution, the aqueous layer was saturated with sodium chloride and extracted with ethyl acetate three times. The combined organic phases were dried (MgSO$_4$), filtered, and evaporated to afford the title compound (5.02 g), which was directly used in the next step. Colorless oil, MS (ISP)=196.1 (M+H)$^+$.

B) ((S)-3-Benzyloxy-1-hydroxymethyl-propyl)-carbamic acid tert-butyl ester

The title compound was produced in analogy with the procedure described in intermediate 20E from (S)-2-amino-4-benzyloxy-butan-1-ol. Light yellow oil, MS (ISP)=318.3 (M+Na)$^+$.

C) ((S)-3-Benzyloxy-1-methoxymethyl-propyl)-carbamic acid tert-butyl ester

Silver(I) oxide (4.49 g, 19.4 mmol) and iodomethane (2.75 g, 19.4 mmol) were added at room temperature to a solution or ((S)-3-benzyloxy-1-hydroxymethyl-propyl)-carbamic acid tert-butyl ester (2.60 g, 8.81 mmol) in N,N-dimethylformamide (8 mL). The reaction mixture was heated at 40° C. for 2.5 h, then insoluble material was removed by filtration through diatomaceous earth. After evaporation of the filtrate, the residue was taken up in ethyl acetate and washed with water. The organic layer was washed with brine, dried (MgSO$_4$), filtered, and evaporated to afford the title compound (2.72 g, 100%), which was used without further purification. Colorless liquid, MS (ISP)=310.3 (M+H)$^+$.

D) (S)-3-Benzyloxy-1-methoxymethyl-propylamine

Trifluoroacetic acid (17.1 g, 150 mmol) was added at 0° C. to a solution of ((S)-3-benzyl-oxy-1-methoxymethyl-propyl)-carbamic acid tert-butyl ester (3.09 g, 10.0 mmol) in dichloromethane (30 mL). The ice bath was removed, then after 90 min the reaction mixture was evaporated. The residue was taken up in ethyl acetate and water and washed with 2 M aq. sodium carbonate solution. The organic layer was washed with brine, dried (MgSO$_4$), filtered, and evaporated. Chromatography (SiO$_2$; dichloromethane/methanol/25% aq. ammonia solution 95:5:0.25) furnished the title compound (1.34 g, 64%). Light yellow liquid, MS (ISP)=210.2 (M+H)$^+$.

E) ((S)-3-Benzyloxy-1-methoxymethyl-propyl)-(2,2-dimethoxy-ethyl)-amine

To a solution of (S)-3-benzyloxy-1-methoxymethyl-propylamine (1.34 g, 6.40 mmol) in methanol (25 mL) were added dimethoxyacetaldehyde solution (45% in tert-butyl methyl ether, 1.81 mL, 7.04 mmol), magnesium sulfate (6.94 g, 57.6 mmol), acetic acid (1.54 g, 25.6 mmol), and sodium cyanoborohydride (551 mg, 8.32 mmol), then after 4 h the reaction mixture was cooled to 0° C. and treated with another portion of dimethoxyacetaldehyde solution (45% in tert-butyl methyl ether, 0.22 mL, 0.96 mmol). The ice bath was removed, then after 2 h the reaction was stopped by careful addition of sat. aq. sodium hydrogencarbonate solution. The reaction mixture was partitioned between sat. aq. sodium hydrogencarbonate solution and ethyl acetate, the organic layer was washed with brine, dried (MgSO$_4$), filtered, and evaporated. Chromatography (SiO$_2$; dichloromethane/ methanol 19:1) furnished the title compound (1.60 g, 84%). Light yellow liquid, MS (ISP)=298.3 (M+H)+.

F) {(S)-1-[((S)-3-Benzyloxy-1-methoxymethyl-propyl)-(2,2-dimethoxy-ethyl)-carbamoyl]-ethyl}-carbamic acid tert-butyl ester To a solution of N-(tert-butoxycarbonyl)-L-alanine (1.12 g, 5.92 mmol) and ((S)-3-benzyloxy-1-methoxymethyl-propyl)-(2,2-dimethoxy-ethyl)-amine (1.60 g, 5.38 mmol) in N,N-dimethylformamide (16 mL) were added 4-methylmorpholine (1.63 g, 16.1 mmol) and O-(7-azabenzotriazol-1-yl)-1,1,3,3-tetramethyluronium hexafluorophosphate (3.07 g, 8.06 mmol) at room temperature. The reaction mixture was stirred at room temperature was stirred at room temperature for 16 h, then partitioned between water and heptane/ethyl acetate 1:1. The organic layer was dried (MgSO4), filtered, and evaporated. Chromatography (SiO2; heptane-ethyl acetate gradient) furnished the title compound (2.20 g, 87%). Colorless oil, MS (ISP)=469.4 (M+H)+.

G) (S)-1-((S)-3-Benzyloxy-1-methoxymethyl-propyl)-3-methyl-piperazin-2-one

Trifluoroacetic acid (8.03 g, 70.4 mmol) was added at 0° C. to a solution of {(S)-1-[((S)-3-benzyloxy-1-methoxymethyl-propyl)-(2,2-dimethoxy-ethyl)-carbamoyl]-ethyl}-carbamic acid tert-butyl ester (2.20 g, 4.69 mmol) in dichloromethane (40 mL). The reaction mixture was allowed to reach room temperature over 2 h, then triethylsilane (2.73 g, 70.4 mmol) was added. The reaction mixture was stirred for 16 h at room temperature, then cooled to 0° C. and treated with triethylamine (7.24 g, 70.4 mmol). After 10 min the ice bath was removed and the reaction mixture evaporated. The residue was taken up in ethyl acetate/water and neutralized with 2 M aq. sodium carbonate solution. The organic layer was washed with brine, dried (MgSO4), filtered, and evaporated. Chomatography (SiO2; dichloromethane-methanol gradient) afforded the title compound (735 mg, 51%). Light yellow oil, MS (ISP)=307.3 (M+H)+.

H) (S)-4-((S)-3-Benzyloxy-1-methoxymethyl-propyl)-2-methyl-3-oxo-piperazine-1-carboxylic acid tert-butyl ester The title compound was produced in analogy with the procedure described in intermediate 20E from (S)-1-((S)-3-benzyloxy-1-methoxymethyl-propyl)-3-methyl-piperazin-2-one. Colorless oil, MS (ISP)=407.4 (M+H)+.

I) (S)-4-((S)-3-Hydroxy-1-methoxymethyl-propyl)-2-methyl-3-oxo-piperazine-1-carboxylic acid tert-butyl ester The title compound was produced in analogy with the procedure described in intermediate 22C from (S)-4-((S)-3-benzyloxy-1-methoxymethyl-propyl)-2-methyl-3-oxo-piperazine-1-carboxylic acid tert-butyl ester. Grey oil, MS (ISP)=317.2 (M+H)+.

J) (S)-4-[(S)-3-((S)-4-Hydroxy-6-aza-spiro[2.5]oct-6-yl)-1-methoxymethyl-propyl]-2-methyl-3-oxo-piperazine-1-carboxylic acid tert-butyl ester In analogy to the procedure described in intermediate 20F, the title compound was produced by oxidation of (S)-4-((S)-3-hydroxy-1-methoxymethyl-propyl)-2-methyl-3-oxo-piperazine-1-carboxylic acid tert-butyl ester, followed by reductive amination of the aldehyde intermediate (S)-4-((S)-3-oxo-1-methoxymethyl-propyl)-2-methyl-3-oxo-piperazine-1-carboxylic acid tert-butyl ester with (S)-6-aza-spiro[2.5]octan-4-ol hydrochloride (intermediate 2). Colorless oil, MS (ISP)=426.3 (M+H)+.

Intermediate 24

(S)-4-((S)-1-Methoxymethyl-3-piperidin-1-yl-propyl)-2-methyl-3-oxo-piperazine-1-carboxylic acid tert-butyl ester In analogy to the procedure described in intermediate 20F, the title compound was produced by oxidation of (S)-4-((S)-3-hydroxy-1-methoxymethyl-propyl)-2-methyl-3-oxo-piperazine-1-carboxylic acid tert-butyl ester (intermediate 23I), followed by reductive amination of the aldehyde intermediate (S)-4-((S)-3-oxo-1-methoxymethyl-propyl)-2-methyl-3-oxo-piperazine-1-carboxylic acid tert-butyl ester with piperidine. Colorless gum, MS (ISP)=384.3 (M+H)+.

Intermediate 25

(R)-4-[(S)-3-((S)-4-hydroxy-6-aza-spiro[2.5]oct-6-yl)-1-methoxymethyl-propyl]-2-methyl-3-oxo-piperazine-1-carboxylic acid tert-butyl ester The title compound was produced in analogy with intermediate 23, steps F-J from ((S)-3-benzyloxy-1-methoxymethyl-propyl)-(2,2-dimethoxy-ethyl)-amine (intermediate 23E). Thus, amide coupling with N-(tert-butoxycarbonyl)-D-alanine in step F gave {(R)-1-[((S)-3-benzyloxy-1-methoxymethyl-propyl)-(2,2-dimethoxy-ethyl)-carbamoyl]-ethyl}-carbamic acid tert-butyl ester, which was cyclized in step G to (R)-1-((S)-3-benzyloxy-1-methoxymethyl-propyl)-3-methyl-piperazin-2-one. This was protected in step H to (R)-4-((S)-3-benzyloxy-1-methoxymethyl-propyl)-2-methyl-3-oxo-piperazine-1-carboxylic acid tert-butyl ester, which was debenzylated in step I, leading to (R)-4-((S)-3-hydroxy-1-methoxymethyl-propyl)-2-methyl-3-oxo-piperazine-1-carboxylic acid tert-butyl ester. Finally, oxidation in step J furnished aldehyde (R)-4-((S)-3-oxo-1-methoxymethyl-propyl)-2-methyl-3-oxo-piperazine-1-carboxylic acid tert-butyl ester, which then underwent a reductive amination reaction with (S)-6-aza-spiro[2.5]octan-4-ol hydrochloride (intermediate 2). Colorless oil, MS (ISP)=426.3 (M+H)+.

Intermediate 26

(S)-4-((S)-1-Hydroxymethyl-3-piperidin-1-yl-propyl)-2-methyl-3-oxo-piperazine-1-carboxylic acid tert-butyl ester A) (S)-3-Benzyloxy-1-(tert-butyl-diphenyl-silanyloxymethyl)-propylamine To a solution of (S)-2-amino-4-benzyloxy-butan-1-ol (intermediate 23A; 200 mg, 1.02 mmol) in N,N-dimethylformamide (1 mL) were added imidazole (77 mg, 1.21 mmol) and tert-butyldiphenylsilyl chloride (319 mg, 1.21 mmol) at room temperature. After 16 h the reaction mixture was partitioned between ethyl acetate and water. The aqueous phase was extracted with ethyl acetate. The organic layers were combined, washed with brine, dried (MgSO4), filtered, and evaporated. Chromatography (SiO$_2$; ethyl acetate) produced the title compound (294 mg, 71%). Colorless oil, MS (ISP)=434.3 (M+H)$^+$.

B) [(S)-3-Benzyloxy-1-(tert-butyl-diphenyl-silanyloxymethyl)-propyl]-(2,2-dimethoxy-ethyl)-amine The title compound was produced in analogy with the procedure described in intermediate 23E from (S)-3-benzyloxy-1-(tert-butyl-diphenyl-silanyloxymethyl)-propyl amine. Colorless oil, MS (ISP)=522.4 (M+H)$^+$.

C) {(S)-1-[[(S)-3-Benzyloxy-1-(tert-butyl-diphenyl-silanyloxymethyl)-propyl]-(2,2-dimethoxy-ethyl)-carbamoyl]-ethyl}-carbamic acid tert-butyl ester The title compound was produced in analogy with the procedure described in intermediate 23F from [(S)-3-benzyloxy-1-(tert-butyl-diphenyl-silanyloxymethyl)-propyl]-(2,2-dimethoxy-ethyl)-amine and N-(tert-butoxycarbonyl)-L-alanine. Colorless oil, MS (ISP)=693.3 (M+H)$^+$.

D) (S)-1-[(S)-3-Benzyloxy-1-(tert-butyl-diphenyl-silanyloxymethyl)-propyl]-3-methyl-piperazin-2-one The title compound was produced in analogy with the procedure described in intermediate 23G from {(S)-1-[[(S)-3-benzyloxy-1-(tert-butyl-diphenyl-silanyloxymethyl)-propyl]-(2,2-dimethoxy-ethyl)-carbamoyl]-ethyl}-carbamic acid tert-butyl ester. Light brown oil, MS (ISP)=531.2 (M+H)$^+$.

E) (S)-4-[(S)-3-benzyloxy-1-(tert-butyl-diphenyl-silanyloxymethyl)-propyl]-2-methyl-3-oxo-piperazine-1-carboxylic acid tert-butyl ester The title compound was produced in analogy with the procedure described in intermediate 20E from (S)-1-[(S)-3-benzyloxy-1-(tert-butyl-diphenyl-silanyloxymethyl)-propyl]-3-methyl-piperazin-2-one. Colorless oil, MS (ISP)=631.4 (M+H)$^+$.

F) (S)-4-[(S)-1-(tert-Butyl-diphenyl-silanyloxymethyl)-3-hydroxy-propyl]-2-methyl-3-oxo-piperazine-1-carboxylic acid tert-butyl ester The title compound was produced in analogy with the procedure described in intermediate 22C from (S)-4-[(S)-3-benzyloxy-1-(tert-butyl-diphenyl-silanyloxymethyl)-propyl]-2-methyl-3-oxo-piperazine-1-carboxylic acid tert-butyl ester. Colorless gum, MS (ISP)=541.3 (M+H)$^+$.

G) (S)-4-[(S)-1-(tert-Butyl-diphenyl-silanyloxymethyl)-3-piperidin-1-yl-propyl]-2-methyl-3-oxo-piperazine-1-carboxylic acid tert-butyl ester In analogy to the procedure described in intermediate 20F, the title compound was produced by oxidation of (S)-4-[(S)-1-(tert-butyl-diphenyl-silanyloxymethyl)-3-hydroxy-propyl]-2-methyl-3-oxo-piperazine-1-carboxylic acid tert-butyl ester, followed by reductive amination of the aldehyde intermediate (S)-4-[(S)-1-(tert-butyl-diphenyl-silanyloxymethyl)-3-oxo-propyl]-2-methyl-3-oxo-piperazine-1-carboxylic acid tert-butyl ester with piperidine. Colorless oil, MS (ISP)=608.2 (M+H)$^+$.

H) (S)-4-((S)-1-Hydroxymethyl-3-piperidin-1-yl-propyl)-2-methyl-3-oxo-piperazine-1-carboxylic acid tert-butyl ester Tetrabutylammonium fluoride solution (1 M in tetrahydrofuran, 0.14 mL, 0.14 mmol) was added at room temperature to a solution of (S)-4-[(S)-1-(tert-butyl-diphenyl-silanyloxymethyl)-3-piperidin-1-yl-propyl]-2-methyl-3-oxo-piperazine-1-carboxylic acid tert-butyl ester (75 mg, 0.12 mmol) in tetrahydrofuran (1 mL), then after 16 h another portion of tetrabutylammonium fluoride solution (1 M in tetrahydrofuran, 20 µL, 20 µmol) was added. The reaction mixture was stirred at room temperature for another 60 min, then evaporated. Chromatography (SiO$_2$; dichloromethane dichloromethane/methanol/25% aq. ammonia solution 90:10:0.25) produced the title compound (42 mg, 92%). Colorless gum, MS (ISP)=370.3 (M+H)$^+$.

Intermediate 27

(S)-1-[4-((S)-4-Hydroxy-6-aza-spiro[2.5]oct-6-yl)-butyl]-3-methyl-piperazin-2-one A) (S)-2-(2,2-Dimethoxy-ethylamino)-propionic acid methyl ester To a solution of L-alanine methyl ester hydrochloride (5.00 g, 35.8 mmol) in methanol (100 mL) were added at 0° C. dimethoxyaldehyde (45% solution in tert-butyl methyl ether, 12.0 mL, 47 mmol) magnesium sulfate (38.8 g, 322 mmol), and sodium cyanoborohydride (3.08 g, 46.6 mmol). The ice bath was removed, then after 16 h the excess reagent was destroyed by careful addition of sat. aq. sodium hydrogencarbonate solution at 0° C. The reaction mixture was partitioned between sat. aq. sodium hydrogencarbonate solution and ethyl acetate. The organic layer was washed with brine, dried (MgSO$_4$), filtered, and evaporated to afford the title compound (5.50 g, 80%). Light yellow liquid, MS (ISP)=192.2 (M+H)$^+$.

B) (S)-2-[Benzyloxycarbonyl-(2,2-dimethoxy-ethyl)-amino]-propionic acid methyl ester Benzyl chloroformate (4.46 g, 24.8 mmol) was added at 0° C. to a mixture of (S)-2-(2,2-dimethoxy-ethylamino)-propionic acid methyl ester (4.75 g, 24.8 mmol) and sodium hydrogencarbonate (4.17 g, 49.7 mmol) in acetone (25 mL) and water (25 mL). The ice bath was removed, then after 2 h the reaction mixture was poured onto ice water and extracted with ethyl acetate. The organic layer was dried (MgSO$_4$), filtered, and evaporated. Chromatography (SiO$_2$; heptane-ethyl acetate gradient afforded the title compound (5.84 g, 72%). Yellow oil, MS (ISP)=348.2 (M+Na)$^+$.

C) (S)-2-[Benzyloxycarbonyl-(2-oxo-ethyl)-amino]-propionic acid methyl ester

A solution of (S)-2-[benzyloxycarbonyl-(2,2-dimethoxy-ethyl)-amino]-propionic acid methyl ester (26.0 g, 80.0 mmol) and pyridinium toluene-4-sulfonate (10.0 g, 40.0 mmol) in 2-butanone (260 mL) and water (8.6 mL, 0.48 mol) was heated under reflux for 16 h, then the solution was partitioned between ethyl acetate and water. The organic layer was washed with brine, dried (MgSO$_4$), filtered, and evaporated to afford the title compound (24.3 g), which was directly used in the next step. Yellow oil, MS (ISP)=348.3 (M+Na)$^+$.

D) (S)-4-(4-Hydroxy-butyl)-2-methyl-3-oxo-piperazine-1-carboxylic acid benzyl ester A solution of (S)-2-[benzyloxycarbonyl-(2-oxo-ethyl)-amino]-propionic acid methyl ester (24.3 g, 80 mmol) in dichloromethane (130 mL) was added at room temperature over 15 min to a suspension of 4-amino-1-butanol (7.12 g, 80 mmol), acetic acid (9.6 g, 0.16 mol), and sodium triacetoxyborohydride (25.4 g, 0.12 mol), then after 16 h triethylamine (16.2 g, 0.16 mol) was added, and the reaction mixture was concentrated under vacuum. The residue was partitioned between 2 M aq. sodium carbonate solution and ethyl acetate. The organic layer was dried (MgSO$_4$), filtered, and evaporated. Chromatography (SiO$_2$; dichloromethane, then dichloromethane/methanol/25% aq. ammonia solution 90:10:0.25) afforded the title compound (16.8 g, 66%). Yellow oil, MS (ISP)=321.2 (M+H)$^+$.

E) (S)-4-[4-((S)-4-hydroxy-6-aza-spiro[2.5]oct-6-yl)-butyl]-2-methyl-3-oxo-piperazine-1-carboxylic acid benzyl ester To a solution of (S)-4-(4-hydroxy-butyl)-2-methyl-3-oxo-piperazine-1-carboxylic acid benzyl ester (1.67 g, 5.21 mmol) in dichloromethane (18 mL) were added at room temperature trichloroisocyanuric acid (1.28 g, 5.21 mmol) and 2,2,6,6-tetramethylpiperidin-1-oxyl (8 mg, 0.05 mmol), upon which an exothermic reaction (T$_{max}$=36° C.) under gas evolution started. The reaction mixture was stirred for 5 min, then insoluble material was removed by filtration. The filtrate was washed with 1 M aq. sodium thiosulfate solution and brine, dried (MgSO$_4$), filtered, and evaporated to afford (S)-4-(4-oxo-butyl)-2-methyl-3-oxo-piperazine-1-carboxylic acid benzyl ester (1.56 g). This aldehyde (MS (ISP)=319.1 (M+H)$^+$) was taken up in dichloromethane (9 mL) and added at room temperature to a suspension of (S)-6-aza-spiro[2.5]octan-4-ol hydrochloride (intermediate 2; 853 mg, 5.21 mmol), triethylamine (527 mg, 5.21 mmol), acetic acid (626 mg, 10.4 mmol), and sodium triacetoxyborohydride (1.21 g, 5.73 mmol) in dichloromethane (9 mL). The reaction mixture was stirred for 30 min, then cooled to 0° C. and treated with 25% aq. ammonia solution (1.07 mL), then allowed to reach room temperature and concentrated in vacuo. Chromatography (SiO$_2$; dichloromethane→dichloromethane/methanol/25% aq. ammonia solution 90:10:0.25) afforded the title compound (1.26 g, 56%). Colorless gum, MS (ISP)=430.3 (M+H)$^+$.

F) (S)-1-[4-((S)-4-Hydroxy-6-aza-spiro[2.5]oct-6-yl)-butyl]-3-methyl-piperazin-2-one The title compound was produced in analogy with the procedure described in intermediate 22C from (S)-4-[4-((S)-4-hydroxy-6-aza-spiro[2.5]oct-6-yl)-butyl]-2-methyl-3-oxo-piperazine-1-carboxylic acid benzyl ester. Yellow oil, MS (ISP)=296.4 (M+H)$^+$.

Intermediate 28

(3-Pyridin-3-yl-phenyl)-carbamic acid phenyl ester

A solution of 3-pyridin-3-ylaniline (500 mg, 2.94 mmol) in tetrahydrofuran (6 mL) was added at room temperature to a solution of phenyl chloroformate (450 mg, 2.94 mmol), then triethylamine (288 mg, 2.84 mmol) was added. After 15 min the reaction mixture was concentrated under vacuum, then the residue was partitioned between ethyl acetate and 1 M aq. sodium hydrogencarbonate solution. The organic layer was dried (MgSO$_4$) and evaporated. The residue was taken up in tetrahydrofuran (1 mL), then heptane (10 mL) was added. The slurry was stirred for 30 min, then the precipitate was collected by filtration to afford the title compound (566 mg, 68%). Off-white solid, MS (ISP)=291.1 (M+H)$^+$.

Intermediate 29

(3-Pyridin-4-yl-phenyl)-carbamic acid phenyl ester

The title compound was produced in analogy with the procedure described in intermediate 28 from 3-pyridin-4-ylaniline. Off-white solid, MS (ISP)=291.1 (M+H)$^+$.

Intermediate 30

Quinolin-6-yl-carbamic acid phenyl ester

The title compound was produced in analogy with the procedure described in intermediate 28 from 6-aminoquinoline. Off-white solid, MS (ISP)=265.2 (M+H)$^+$.

Intermediate 31

Quinolin-7-yl-carbamic acid phenyl ester

The title compound was produced in analogy with the procedure described in intermediate 28 from 7-aminoquinoline. Light yellow solid, MS (ISP)=265.2 (M+H)$^+$.

Intermediate 32

Isoquinolin-7-yl-carbamic acid phenyl ester

The title compound was produced in analogy with the procedure described in intermediate 28 from 7-aminoisoquinoline. Off-white solid, MS (ISP)=265.2 (M+H)$^+$.

Intermediate 33

(5-Trifluoromethyl-pyridin-2-yl)-carbamic acid phenyl ester

The title compound was produced in analogy with the procedure described in intermediate 28 from 2-amino-5-(trifluoromethyl)pyridine. White solid, MS (ISP)=281.1 (M+H)$^+$.

Intermediate 34

(4-Trifluoromethyl-pyridin-2-yl)-carbamic acid phenyl ester

The title compound was produced in analogy with the procedure described in intermediate 28 from 2-amino-4-(trifluoromethyl)pyridine. Light yellow solid, $^1$H-NMR (300 MHz, CDCl$_3$): 8.88 (d, J=5.1 Hz, 1H), 8.6-8.5 (m, 2H), 7.70 (d, J=5.1 Hz, 1H), 7.65 (s, 1H), 7.49 (s, 1H), 7.25-7.2 (m, 2H), 6.86 (dd, J=7.5 Hz, 1.8 Hz, 1H).

Intermediate 35

(6-Trifluoromethyl-pyridin-2-yl)-carbamic acid phenyl ester

The title compound was produced in analogy with the procedure described in intermediate 28 from 2-amino-6-(trifluoromethyl)pyridine. White solid, MS (ISP)=281.2 (M+H)+.

Intermediate 36

Isoquinolin-6-yl-carbamic acid phenyl ester

The title compound was produced in analogy with the procedure described in intermediate 28 from 6-aminoisoquinoline. White solid, MS (ISP)=265.1 (M+H)+.

Intermediate 37

(S)-4-[2-((S)-4-Hydroxy-6-aza-spiro[2.5]oct-6-yl)-ethyl]-1-methyl-3-oxo-piperazine-1-carboxylic acid benzyl ester A) (S)-4-(2-Hydroxy-ethyl)-2-methyl-3-oxo-piperazine-1-carboxylic acid benzyl ester The title compound was produced in analogy with the procedure described in intermediate 27D from (S)-2-[benzyloxycarbonyl-(2-oxo-ethyl)-amino]-propionic acid methyl ester (intermediate 27C) and ethanolamine. Colorless oil, MS (ISP)=293.1 (M+H)+.

B) (S)-4-[2-((S)-4-hydroxy-6-aza-spiro[2.5]oct-6-yl)-ethyl]-2-methyl-3-oxo-piperazine-1-carboxylic acid benzyl ester In analogy to the procedure described in intermediate 27E, the title compound was produced by oxidation of (S)-4-(2-hydroxy-ethyl)-2-methyl-3-oxo-piperazine-1-carboxylic acid benzyl ester, followed by reductive amination of the aldehyde intermediate (S)-4-(2-oxo-ethyl)-2-methyl-3-oxo-piperazine-1-carboxylic acid benzyl ester with (S)-6-aza-spiro[2.5]octan-4-ol hydrochloride (intermediate 2). Colorless gum, MS (ISP)=402.4 (M+H)+.

Intermediate 38

(S)-4-[3-((S)-4-Hydroxy-6-aza-spiro[2.5]oct-6-ylmethyl)-oxetan-3-ylmethyl]-2-methyl-3-oxo-piperazine-1-carboxylic acid benzyl ester A) (S)-4-(3-Hydroxymethyl-oxetan-3-ylmethyl)-2-methyl-3-oxo-piperazine-1-carboxylic acid benzyl ester A solution of (S)-2-[benzyloxycarbonyl-(2-oxo-ethyl)-amino]-propionic acid methyl ester (intermediate 27C; 258 mg, 0.92 mmol) in dichloromethane (1 mL) was added at room temperature to a suspension of (3-(aminomethyl)oxetan-3-yl)methanol (108 mg, 0.92 mmol), sodium triacetoxyborohyride (222 mg, 1.01 mmol) and acetic acid (111 mg, 1.85 mmol) in dichloromethane (1 mL). The reaction mixture was heated at 40° C. for 16 h, then partitioned between 1 M aq. sodium carbonate solution and ethyl acetate. The organic layer was washed with brine, dried (MgSO4), and evaporated. The residue was taken up in methanol (2 mL), then after addition of potassium carbonate (255 mg, 1.85 mmol) the suspension was stirred for 2 h. The reaction mixture was partitioned between sat. aq. ammonium chloride solution and ethyl acetate. The organic layer was washed with brine, dried (MgSO4), and evaporated. Chromatography (SiO2; dichloromethane/methanol/25% aq. ammonia solution 90:10:0.25) afforded the title compound (45 mg, 14%). Light yellow oil, MS (ISP)=349.3 (M+H)+.

B) (S)-4-[3-((S)-4-Hydroxy-6-aza-spiro[2.5]oct-6-ylmethyl)-oxetan-3-ylmethyl]-2-methyl-3-oxo-piperazine-1-carboxylic acid benzyl ester In analogy to the procedure described in intermediate 27E, the title compound was produced by oxidation of (S)-4-(3-hydroxymethyl-oxetan-3-ylmethyl)-2-methyl-3-oxo-piperazine-1-carboxylic acid benzyl ester, followed by reductive amination of the aldehyde intermediate (S)-4-(3-oxomethyl-oxetan-3-ylmethyl)-2-methyl-3-oxo-piperazine-1-carboxylic acid benzyl ester with (S)-6-aza-spiro[2.5]octan-4-ol hydrochloride (intermediate 2). Colorless gum, MS (ISP)=458.3 (M+H)+.

Intermediate 39

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid benzyl ester A) (S)-4-(2-Hydroxy-ethyl)-2,2-dimethyl-oxazolidine-3-carboxylic acid benzyl ester A solution of (S)—N-(benzyloxycarbonyl)-2-aminobutane-1,4-diol (8.00 g, 33.4 mmol) and toluene-4-sulfonic acid monohydrate (318 mg, 1.67 mmol) in 2,2-dimethoxypropane (320 mL) was stirred at room temperature, then after 2 h 2-methoxypropene (7.71 g, 107 mmol) was added, then after 72 h the reaction mixture was partitioned between ethyl acetate and sat. aq. sodium hydrogencarbonate solution. The organic layer was dried (MgSO4), filtered, and evaporated. The residue was taken up in dichloromethane (200 mL), then after addition of SiO2 (80 g) and water (4.8 mL) the slurry was stirred for 64 h at room temperature. After dilution with dichloromethane and addition of anhydrous magnesium sulfate, insoluble material was removed by filtration through diatomaceous earth. The filtrate was evaporated and chromatographed (SiO2; heptane/ethyl acetate 1:1) to afford the title compound (8.92 g, 96%). Light yellow oil, MS (ISP)=280.1 (M+H)+.

B) (S)-2,2-Dimethyl-4-(2-oxo-ethyl)-oxazolidine-3-carboxylic acid benzyl ester

A solution of dimethyl sulfoxide (6.39 g, 81.8 mmol) in dichloromethane (25 mL) as added at −70° C. to a solution of oxalyl chloride (5.59 g, 44.1 mmol) in dichloromethane (90 mL), then after 15 min a solution of (S)-4-(2-hydroxy-ethyl)-2,2-dimethyl-oxazolidine-3-carboxylic acid benzyl ester (8.79 g, 31.5 mmol) in dichloromethane (45 mL) was added dropwise. After 60 min triethylamine (15.9 g, 157 mmol) was added, then after 20 min the cooling bath was removed and the reaction mixture was stirred for 2 h. The reaction mixture was poured onto water and extracted five times with dichloromethane. The combined organic phases were dried (MgSO4), filtered, and evaporated. Chromatography (SiO2;

C) (S)-4-[2-((S)-4-hydroxy-6-aza-spiro[2.5]oct-6-yl)-ethyl]-2,2-dimethyl-oxazolidine-3-carboxylic acid benzyl ester To a solution of (S)-2,2-dimethyl-4-(2-oxo-ethyl)-oxazolidine-3-carboxylic acid benzyl ester (8.51 g, 30.7 mmol) in dichloromethane (140 mL) were added (S)-6-aza-spiro[2.5]octan-4-ol hydrochloride (intermediate 2; 5.03 g, 30.7 mmol), triethylamine (3.11 g, 30.7 mmol) and sodium triacetoxyborohydride (9.11 g, 43.0 mmol) at room temperature. After 1 h the reaction mixture was partitioned between sat. aq. sodium hydrogencarbonate solution and dichloromethane. The aqueous layer was extracted twice with dichloromethane, the combined organic phases were dried (MgSO$_4$), filtered, and evaporated to afford the title compound (11.6 g, 97%). Light yellow gum, MS (ISP)=389.3 (M+H)$^+$.

D) [(S)-3-((S)-4-Hydroxy-6-aza-spiro[2.5]oct-6-yl)-1-hydroxymethyl-propyl]-carbamic acid benzyl ester A solution of (S)-4-[2-((S)-4-hydroxy-6-aza-spiro[2.5]oct-6-yl)-ethyl]-2,2-dimethyl-oxazolidine-3-carboxylic acid benzyl ester (5.00 g, 12.9 mmol) in methanol/water 9:1 (50 mL) was stirred at room temperature in the presence of Amberlite® IR-120 resin (15.8 g). After 16 h the resin was collected by filtration and washed with methanol. The filtrate was discarded, and the product was recovered by digesting the Amberlite® resin three times in 7 M methanolic ammonia solution (60 mL) at room temperature over 15 min. The ammonia solutions were combined and evaporated to afford the title compound (4.27 g, 95%). Colorless oil, MS (ISP)=349.3 (M+H)$^+$.

E) (S)-6-((S)-3-Amino-4-hydroxy-butyl)-6-aza-spiro[2.5]octan-4-ol

The title compound was produced in analogy with the procedure described in intermediate 22C from [(S)-3-((S)-4-hydroxy-6-aza-spiro[2.5]oct-6-yl)-1-hydroxymethyl-propyl]-carbamic acid benzyl ester. Colorless gum, MS (ISP)=215.3 (M+H)$^+$.

F) (S)-4-[(S)-3-((S)-4-Hydroxy-6-aza-spiro[2.5]oct-6-yl)-1-hydroxymethyl-propyl]-2-methyl-3-oxo-piperazine-1-carboxylic acid benzyl ester A solution of (S)-2-[benzyloxycarbonyl-(2-oxo-ethyl)-amino]-propionic acid methyl ester (intermediate 27C, 2.35 g, 8.42 mmol) in dichloromethane (15 mL) was added at room temperature to a suspension of (S)-6-((S)-3-amino-4-hydroxy-butyl)-6-aza-spiro[2.5]octan-4-ol (1.81 g, 8.42 mmol), sodium triacetoxyborohyride (2.21 g, 1.01 mmol) and acetic acid (1.01 g, 16.8 mmol) in dichloromethane (15 mL). The reaction mixture was heated at 40° C. for 72 h, then partitioned between 1 M aq. sodium carbonate solution and ethyl acetate. The organic layer was washed with brine, dried (MgSO$_4$), and evaporated. Chromatography (SiO$_2$; dichloromethane→dichloromethane/methanol/25% aq. ammonia solution 90:10:0.25) produced the title compound (2.18 g, 58%). White foam, MS (ISP)=446.2 (M+H)$^+$.

Intermediate 40

(S)-4-[(S)-2-Hydroxy-3-((S)-4-hydroxy-6-aza-spiro[2.5]oct-6-yl)-propyl]-2-methyl-3-oxo-piperazine-1-carboxylic acid benzyl ester

A) [(R)-2-Hydroxy-3-((S)-4-hydroxy-6-aza-spiro[2,5]oct-6-yl)-propyl]-carbamic acid benzyl ester In analogy to the procedure described in intermediate 27E, the title compound was produced by oxidation of ((R)-2,3-dihydroxy-propyl)-carbamic acid benzyl ester (*J. Am. Chem. Soc.* 2007, 129, 14811), followed by reductive amination of the aldehyde intermediate ((R)-2-hydroxy-3-oxo-propyl)-carbamic acid benzyl ester with (S)-6-aza-spiro[2.5]octan-4-ol hydrochloride (intermediate 2). Orange oil, MS (ISP)=335.4 (M+H)$^+$.

B) (S)-6-((R)-3-Amino-2-hydroxy-propyl)-6-aza-spiro[2.5]octan-4-ol

The title compound was produced in analogy with the procedure described in intermediate 22C from [(R)-2-hydroxy-3-((S)-4-hydroxy-6-aza-spiro[2.5]oct-6-yl)-propyl]-carbamic acid benzyl ester. Colorless gum, MS (ISP)=201.3 (M+H)$^+$.

C) (S)-4-[(S)-2-Hydroxy-3-((S)-4-hydroxy-6-aza-spiro[2.5]oct-6-yl)-propyl]-2-methyl-3-oxo-piperazine-1-carboxylic acid benzyl ester The title compound was produced in analogy with the procedure described in intermediate 39F from (S)-2-[benzyloxycarbonyl-(2-oxo-ethyl)-amino]-propionic acid methyl ester (intermediate 27C) and (S)-6-((R)-3-amino-2-hydroxy-propyl)-6-aza-spiro[2.5]octan-4-ol. White foam, MS (ISP)=432.3 (M+H)$^+$.

Intermediate 41

(S)-4-[(R)-2-Hydroxy-3-((S)-4-hydroxy-6-aza-spiro[2.5]oct-6-yl)-propyl]-2-methyl-3-oxo-piperazine-1-carboxylic acid benzyl ester The title compound was produced in analogy with intermediate 40, steps A-C. Thus, ((S)-2,3-dihydroxy-propyl)-carbamic acid benzyl ester (*J. Am. Chem. Soc.* 2007, 129, 14811) was oxidized in step A to ((R)-2-hydroxy-3-oxo-propyl)-carbamic acid benzyl ester, followed by reductive amination with (S)-6-aza-spiro[2.5]octan-4-ol hydrochloride (intermediate 2), leading to [(S)-2-hydroxy-3-((S)-4-hydroxy-6-aza-spiro[2.5]oct-6-yl)-propyl]-carbamic acid benzyl ester. This was hydrogenated in step B to (S)-6-((R)-3-amino-2-hydroxy-propyl)-6-aza-spiro[2.5]octan-4-ol followed by reaction with (S)-2-[benzyloxycarbonyl-(2-oxo-ethyl)-amino]-propionic acid methyl ester (intermediate 27C) in step C. White foam, MS (ISP)=432.4 (M+H)$^+$.

Intermediate 42

(S)-4-[(S)-1-Dimethylcarbamoyl-3-((S)-4-hydroxy-6-aza-spiro[2.5]oct-6-yl)-propyl]-2-methyl-3-oxo-piperazine-1-carboxylic acid benzyl ester

A) ((S)-1-Dimethylcarbamoyl-3-hydroxy-propyl)-carbamic acid benzyl ester

To a solution of N-benzyloxycarbonyl-L-homoserine lactone (2.59 g, 11.0 mmol) in tetrahydrofuran (50 mL) was added dimethylamine solution (33% in ethanol, 5.9 mL, 33.0 mmol) at room temperature, then after 16 h volatile material was removed by evaporation under vacuum to afford the title compound (3.33 g), which was directly used in the next step. Brown oil, MS (ISP)=281.1 (M+H)+.

B) ((S)-1-Dimethylcarbamoyl-3-oxo-propyl)-carbamic acid benzyl ester

The title compound was produced in analogy with the procedure described in intermediate 39B from ((S)-1-dimethylcarbamoyl-3-hydroxy-propyl)-carbamic acid benzyl ester. Light yellow oil, MS (ISP)=279.1 (M+H)+.

C [(S)-1-Dimethylcarbamoyl-3-((S)-4-hydroxy-6-aza-spiro[2.5]oct-6-yl)-propyl]-carbamic acid benzyl ester The title compound was produced in analogy with the procedure described in intermediate 39C from ((S)-1-dimethylcarbamoyl-3-oxo-propyl)-carbamic acid benzyl ester and (S)-6-aza-spiro[2.5]octan-4-ol hydrochloride (intermediate 2). White foam, MS (ISP)=390.3 (M+H)+.

D) (S)-2-Amino-4-((S)-4-hydroxy-6-aza-spiro[2.5]oct-6-yl)-N,N-dimethyl-butyramide The title compound was produced in analogy with the procedure described in intermediate 22C from [(S)-1-dimethylcarbamoyl-3-((S)-4-hydroxy-6-aza-spiro[2.5]oct-6-yl)-propyl]-carbamic acid benzyl ester. Light yellow gum, MS (ISP)=256.3 (M+H)+.

E) (S)-4-[(S)-1-Dimethylcarbamoyl-3-((S)-4-hydroxy-6-aza-spiro[2.5]oct-6-yl)-propyl]-2-methyl-3-oxo-piperazine-1-carboxylic acid benzyl ester The title compound was produced in analogy with the procedure described in intermediate 39F from (S)-2-[benzyloxycarbonyl-(2-oxo-ethyl)-amino]-propionic acid methyl ester (intermediate 27C) and (S)-2-amino-4-((S)-4-hydroxy-6-aza-spiro[2.5]oct-6-yl)-N,N-dimethyl-butyramide. Light yellow gum, MS (ISP)=487.4 (M+H)+.

Intermediate 43

(S)-4-[(S)-4-((S)-4-Hydroxy-6-aza-spiro[2.5]oct-6-yl)-1-hydroxymethyl-butyl]-2-methyl-3-oxo-piperazine-1-carboxylic acid benzyl ester A) (S)-4-(3-Hydroxy-propyl)-2,2-dimethyl-oxazolidine-3-carboxylic acid benzyl ester The title compound was produced in analogy with intermediate 39A from (S)—N-(benzyloxycarbonyl)-2-aminopentane-1,5-diol. Light yellow liquid.

B) (S)-2,2-Dimethyl-4-(3-oxo-propyl)-oxazolidine-3-carboxylic acid benzyl ester

The title compound was produced in analogy with intermediate 27E from (S)-4-(3-hydroxy-propyl)-2,2-dimethyl-oxazolidine-3-carboxylic acid benzyl ester. Light yellow liquid.

C) (S)-4-[3-((S)-4-Hydroxy-6-aza-spiro[2,5]oct-6-yl)-propyl]-2,2-dimethyl-oxazolidine-3-carboxylic acid benzyl ester The title compound was produced in analogy with intermediate 39C from (S)-2,2-dimethyl-4-(3-oxo-propyl)-oxazolidine-3-carboxylic acid benzyl ester. Light yellow gum, MS (ISP)=403.3 (M+H)+.

D) [(S)-4-((S)-4-hydroxy-6-aza-spiro[2.5]oct-6-yl)-1-hydroxymethyl-butyl]-carbamic acid benzyl ester The title compound was produced in analogy with intermediate 39D from (S)-4-[3-((S)-4-hydroxy-6-aza-spiro[2.5]oct-6-yl)-propyl]-2,2-dimethyl-oxazolidine-3-carboxylic acid benzyl ester. Colorless oil, MS (ISP)=363.4 (M+H)+.

E) (S)-6-((S)-4-amino-5-hydroxy-pentyl)-6-aza-spiro[2.5]octan-4-ol

The title compound was produced in analogy with the procedure described in intermediate 22C from [(S)-4-((S)-4-hydroxy-6-aza-spiro[2.5]oct-6-yl)-1-hydroxymethyl-butyl]-carbamic acid benzyl ester. Yellow gum, MS (ISP)=229.3 (M+H)+.

F) (S)-4-[(S)-4-((S)-4-Hydroxy-6-aza-spiro[2.5]oct-6-yl)-1-hydroxymethyl-butyl]-2-methyl-3-oxo-piperazine-1-carboxylic acid benzyl ester The title compound was produced in analogy with intermediate 39F from (S)-2-[benzyloxycarbonyl-(2-oxo-ethyl)-amino]-propionic acid methyl ester (intermediate 27C) and (S)-6-((S)-4-amino-5-hydroxy-pentyl)-6-aza-spiro[2.5]octan-4-ol. Light yellow gum, MS (ISP)=460.5 (M+H)+.

Example 1

(R,S)-2-[4-(3-Chloro-phenylcarbamoyl)-7-oxo-[1,4]diazepan-1-yl]-4-((S)-4-hydroxy-6-aza-spiro[2.5]oct-6-yl)-butyric acid methyl ester

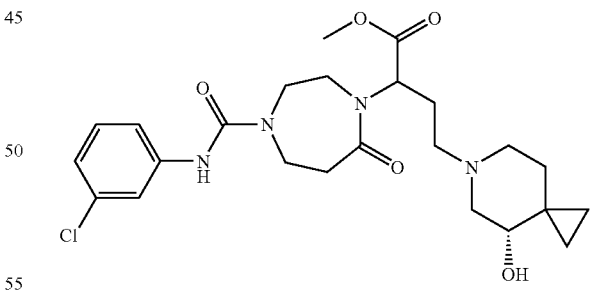

A solution of 0.165 g (0.40 mmol) of (R,S)-4-((S)-4-hydroxy-6-aza-spiro[2.5]oct-6-yl)-2-(7-oxo-[1,4]diazepan-1-yl)-butyric acid methyl ester; dihydrochloride (intermediate 5) in 2.5 ml of N,N-dimethylformamide was treated at room temperature with 0.055 ml (0.44 mmol) of 3-chlorophenyl isocyanate and 0.22 ml (2.00 mmol) of 4-methylmorpholine. The reaction was stirred for 3 h at room temperature and then partitioned between sat. aq. sodium hydrogencarbonate solution and ethyl acetate (3×). The organic phases were washed with sat. aq. sodium hydrogencarbonate solution, 10% aq. sodium chloride solution, dried over Na2SO4 evaporated and purified by flash silica gel column (dichloromethane/methanol 96:4 to 94:6) to yield after precipitation with n-pentane 0.175 g (89%) of the title compound as white powder. MS: 493.3 (MH+, 1Cl).

Example 2

(R,S)-4-[3-((S)-4-Hydroxy-6-aza-spiro[2.5]oct-6-yl)-1-hydroxymethyl-propyl]-5-oxo-[1,4]diazepane-1-carboxylic acid (3-chloro-phenyl)-amide

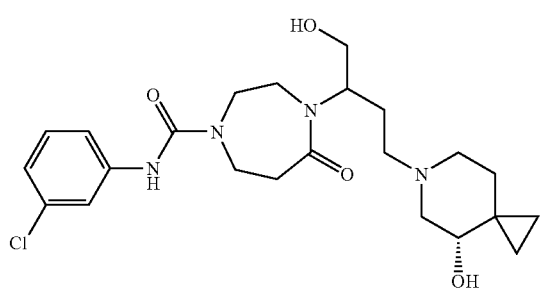

A solution of 0.060 g (0.12 mmol) of (R,S)-2-[4-(3-chlorophenylcarbamoyl)-7-oxo-[1,4]diazepan-1-yl]-4-((S)-4-hydroxy-6-aza-spiro[2.5]oct-6-yl)-butyric acid methyl ester in 0.6 ml of ethanol was treated at 0° C. with 0.06 g (0.24 mmol) of lithium borohydride. The reaction was stirred 10 min at 0° C. and 15 h at room temperature, and then partitioned between sat. aq. sodium hydrogencarbonate solution and ethyl acetate (3×). The organic phases were washed with sat. aq. sodium hydrogencarbonate solution, 10% aq. sodium chloride solution, dried over Na$_2$SO$_4$ evaporated and purified by flash silica gel column (dichloromethane/methanol 9:1 to 4:1) to yield 0.019 g (34%) of the title compound as white powder. MS: 465.3 (MH+, 1Cl).

Example 3

(S)-2-[4-(3-Chloro-phenylcarbamoyl)-7-oxo-[1,4]diazepan-1-yl]-4-((S)-4-hydroxy-6-aza-spiro[2.5]oct-6-yl)-butyric acid methyl ester

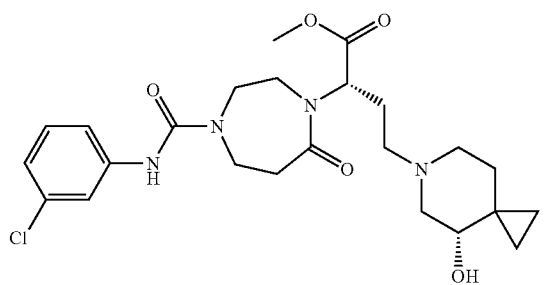

In analogy to the procedure described in Example 1, (S)-4-((S)-4-hydroxy-6-aza-spiro[2.5]oct-6-yl)-2-(7-oxo-[1,4]diazepan-1-yl)-butyric acid methyl ester; dihydrochloride (intermediate 8) and 3-chlorophenyl isocyanate gave the title compound in 75% yield as an off-white powder. MS: 493.3 (MH+, 1Cl).

Example 4

4-[(S)-3-((S)-4-Hydroxy-6-aza-spiro[2.5]oct-6-yl)-1-hydroxymethyl-propyl]-5-oxo-[1,4]diazepane-1-carboxylic acid (3-chloro-phenyl)-amide

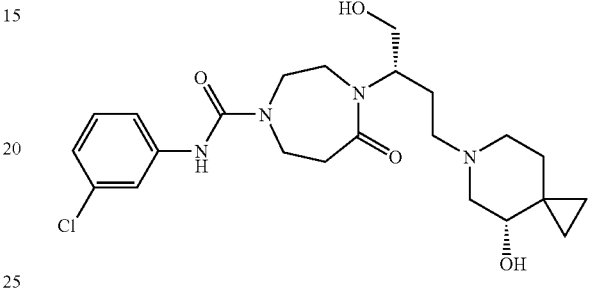

In analogy to the procedure described in Example 2, (S)-2-[4-(3-chloro-phenyl-carbamoyl)-7-oxo-[1,4]diazepan-1-yl]-4-((S)-4-hydroxy-6-aza-spiro[2.5]oct-6-yl)-butyric acid methyl ester and lithium borohydride gave the title compound in 27% yield as an off-white powder. MS: 465.3 (MH+, 1Cl).

Example 5

(R,S)-4-[3-((S)-4-Hydroxy-6-aza-spiro[2.5]oct-6-yl)-1-methoxymethyl-propyl]-5-oxo-[1,4]diazepane-1-carboxylic acid (3-chloro-phenyl)-amide

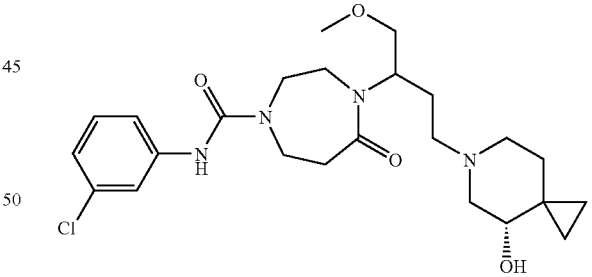

A solution of 0.057 g (0.18 mmol) of (R,S)-4-[3-((S)-4-hydroxy-6-aza-spiro[2.5]oct-6-yl)-1-methoxymethyl-propyl]-[1,4]diazepan-5-one (intermediate 6) 1.1 ml of N,N-dimethylformamide was treated at room temperature with 0.024 ml (0.19 mmol) of 3-chlorophenyl isocyanate and 0.048 ml (0.44 mmol) of 4-methylmorpholine. The reaction was stirred for 3 h at room temperature and then partitioned between sat. aq. sodium hydrogencarbonate solution and ethyl acetate (3×). The organic phases were washed with sat. aq. sodium hydrogencarbonate solution, 10% aq. sodium chloride solution, dried over Na$_2$SO$_4$ evaporated and purified by flash silica gel column (dichloromethane/methanol 95:5 to 9:1) to yield after precipitation with n-pentane 0.056 g (67%) of the title compound as white foam. MS: 479.3 (MH⁺, 1Cl).

Example 6

(R,S)-4-[3-((S)-4-Hydroxy-6-aza-spiro[2.5]oct-6-yl)-1-methoxymethyl-propyl]-5-oxo-[1,4]diazepane-1-carboxylic acid 3,4-dichloro-benzylamide

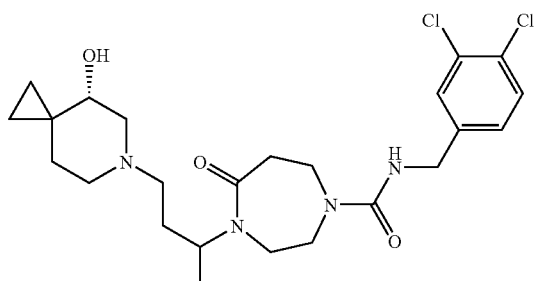

In analogy to the procedure described in Example 5, (R,S)-4-[3-((S)-4-hydroxy-6-aza-spiro[2.5]oct-6-yl)-1-methoxymethyl-propyl]-[1,4]diazepan-5-one (intermediate 6) and 3,4-dichlorobenzyl isocyanate gave the title compound in 68% yield as an off-white foam. MS: 527.3 (MH⁺, 2Cl).

Example 7

(R,S)-4-[3-((S)-4-Hydroxy-6-aza-spiro[2.5]oct-6-yl)-1-methoxymethyl-propyl]-5-oxo-[1,4]diazepane-1-carboxylic acid 3,4-dichloro-phenyl ester

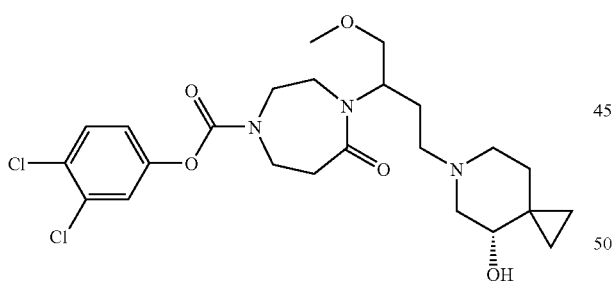

A solution of 0.051 g (0.20 mmol) of imidazole-1-carboxylic acid 3,4-dichloro-phenyl ester (intermediate 9) in 1.2 ml of acetonitrile was treated at room temperature with 0.02 ml (0.21 mmol) of dimethyl sulphate and heated for 2 h at 80° C. The reaction was cooled to room temperature, then 0.059 g (0.18 mmol) (R,S)-4-[3-((S)-4-hydroxy-6-aza-spiro[2.5]oct-6-yl)-1-methoxymethyl-propyl]-[1,4]diazepan-5-one (intermediate 6) in 0.6 ml acetonitrile was dropped in followed by 0.04 ml (0.23 mmol) of N-ethyldiisopropylamine. The reaction was stirred at room temperature for 2 h, and then partitioned between sat. aq. sodium hydrogencarbonate solution and ethyl acetate (×3). The organic phases were washed with sat. aq. sodium hydrogencarbonate solution, 10% aq. sodium chloride solution, dried over Na₂SO₄, evaporated and purified by flash silica gel column (dichloromethane/methanol 97:3 to 94:6) to yield after precipitation with n-pentane 0.055 g (59%) of the title compound as white foam. MS: 514.3 (MH⁺, 2Cl).

Example 8

(R,S)-4-[3-((S)-4-Hydroxy-6-aza-spiro[2.5]oct-6-yl)-1-methoxycarbonyl-propyl]-5-oxo-[1,4]diazepane-1-carboxylic acid 3,4-dichloro-phenyl ester

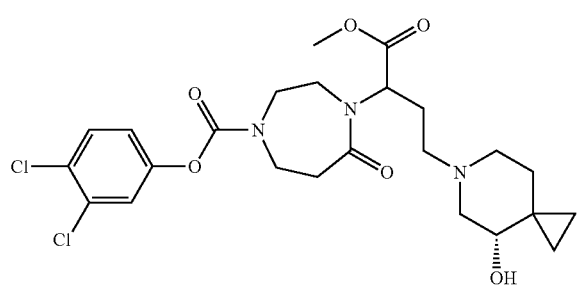

In analogy to the procedure described in Example 7, imidazole-1-carboxylic acid 3,4-dichloro-phenyl ester (intermediate 9) and (R,S)-4-((S)-4-hydroxy-6-aza-spiro[2.5]oct-6-yl)-2-(7-oxo-[1,4]diazepan-1-yl)-butyric acid methyl ester; dihydrochloride (intermediate 5) gave the title compound in 57% yield as white foam. MS: 528.2 (MH⁺, 2Cl).

Example 9

(R,S)-4-[3-((S)-4-Hydroxy-6-aza-spiro[2.5]oct-6-yl)-1-hydroxymethyl-propyl]-5-oxo-[1,4]diazepane-1-carboxylic acid 3,4-dichloro-phenyl ester

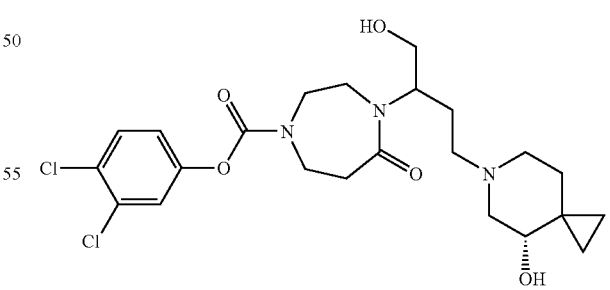

In analogy to the procedure described in Example 2, (R,S)-4-[3-((S)-4-hydroxy-6-aza-spiro[2.5]oct-6-yl)-1-methoxycarbonyl-propyl]-5-oxo-[1,4]diazepane-1-carboxylic acid 3,4-dichloro-phenyl ester and lithium borohydride gave after 3¾ h the title compound in 72% yield as white powder. MS: 500.2 (MH⁺, 2Cl).

Example 10

(R,S)-4-[1-Dimethylcarbamoyl-3-((S)-4-hydroxy-6-aza-spiro[2.5]oct-6-yl)-propyl]-5-oxo-[1,4]diazepane-1-carboxylic acid (3-chloro-phenyl)-amide

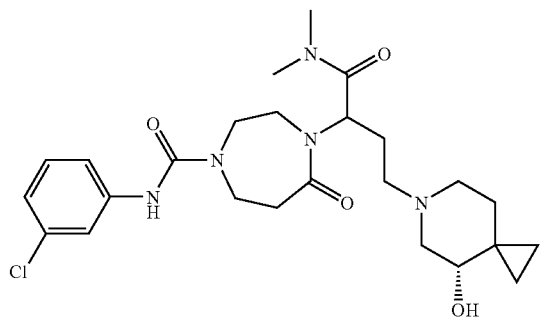

A) Lithium; (R,S)-2-[4-(3-chloro-phenylcarbamoyl)-7-oxo-[1,4]diazepan-1-yl]-4-((S)-4-hydroxy-6-aza-spiro[2.5]oct-6-yl)-butyrate A solution of 0.064 g (0.13 mmol) of (R,S)-2-[4-(3-chlorophenylcarbamoyl)-7-oxo-[1,4]diazepan-1-yl]-4-((S)-4-hydroxy-6-aza-spiro[2.5]oct-6-yl)-butyric acid methyl ester (Example 1) in 0.36 ml of tetrahydrofuran/methanol (1:1) was treated at 0° C. with 0.13 ml (0.13 mmol) of 1 M aq. lithium hydroxide solution, and kept 1.5 h at this temperature and 1¼ h at ambient temperature. The reaction was evaporated, dissolved in acetonitrile and evaporated again (3×) to give 0.06 g (95%) of the title compound as white powder. MS: 479.3 (MH⁺, Cl).

B) (R,S)-4-[1-Dimethylcarbamoyl-3-((S)-4-hydroxy-6-aza-spiro[2.5]oct-6-yl)-propyl]-5-oxo-[1,4]diazepane-1-carboxylic acid (3-chloro-phenyl)-amide 0.053 g (0.11 mmol) of lithium; (R,S)-2-[4-(3-chloro-phenylcarbamoyl)-7-oxo-[1,4]diazepan-1-yl]-4-((S)-4-hydroxy-6-aza-spiro[2.5]oct-6-yl)-butyrate was suspended at room temperature in 0.6 ml of N,N-dimethylformamide followed by addition of 0.044 g (0.12 mmol) dimethylamine hydrochloride, 0.061 ml (0.44 mmol) of triethylamine and at 0° C. with 0.047 g (0.12 µmmol) of O-(7-azabenzotriazol-1-yl)-1,1,3,3-tetramethyluronium hexafluorophosphate. The solution was stirred overnight and warmed up to room temperature. The reaction was poured on a solution of sat. aq. sodium hydrogencarbonate, followed by extraction with ethyl acetate (3 times). The organic phases were washed with a solution of sat. aq. sodium hydrogencarbonate and with a solution of 10% aq. sodium chloride. The combined organic phases were dried over Na₂SO₄ and the solvent was removed under vacuum. The crude product was purified by flash chromatography (20 g amine-silica, ethyl acetate/n-heptane 9:1, 4:1 and ethyl acetate) to yield after precipitation with n-pentane 0.046 g (83%) of the title compound as a white powder. MS: 506.4 (MH⁺, Cl).

Example 11

5-Oxo-4-(3-piperidin-1-yl-propyl)-[1,4]diazepane-1-carboxylic acid (3,4-dichloro-phenyl)-amide

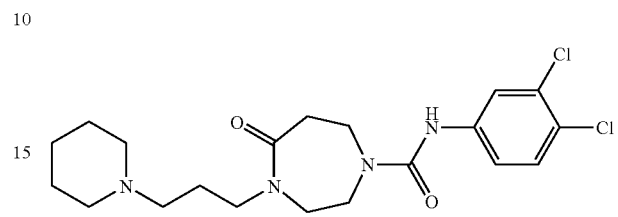

In analogy to the procedure described in Example 1,4-(3-piperidin-1-yl-propyl)-[1,4]diazepan-5-one dihydrochloride (intermediate 10) and 3,4-dichlorophenyl isocyanate gave the title compound in 93% yield as an off-white powder. MS: 427.2 (MH⁺, 2Cl).

Example 12

5-Oxo-4-(3-piperidin-1-yl-propyl)-[1,4]diazepane-1-carboxylic acid (3-trifluoromethyl-phenyl)-amide

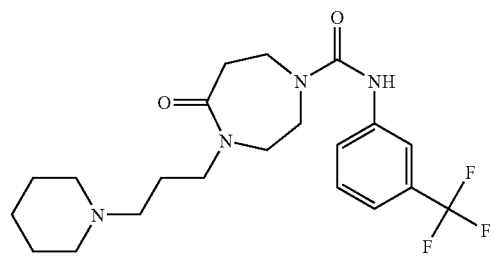

In analogy to the procedure described in Example 1,4-(3-piperidin-1-yl-propyl)-[1,4]diazepan-5-one dihydrochloride (intermediate 10) and 3-trifluoroophenyl isocyanate gave the title compound in 36% yield as an off-white powder. MS: 427.2 (MH⁺).

Example 13

5-Oxo-4-(3-piperidin-1-yl-propyl)-[1,4]diazepane-1-carboxylic acid (3-chloro-phenyl)-amide

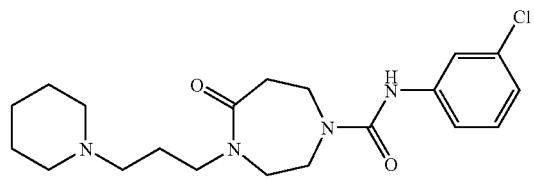

In analogy to the procedure described in Example 1,4-(3-piperidin-1-yl-propyl)-[1,4]diazepan-5-one dihydrochloride (intermediate 10) and 3-chlorophenyl isocyanate gave the title compound in 72% yield as an off-white powder. MS: 393.2 (MH⁺, Cl).

Example 14

5-Oxo-4-(3-piperidin-1-yl-propyl)-[1,4]diazepane-1-carboxylic acid (4-chloro-3-trifluoromethyl-phenyl)-amide

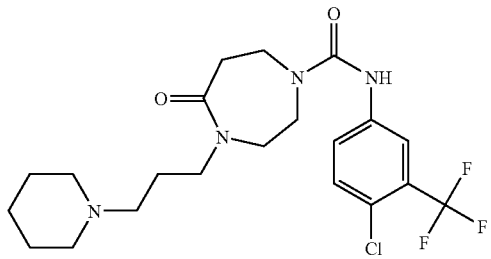

In analogy to the procedure described in Example 1,4-(3-piperidin-1-yl-propyl)-[1,4]diazepan-5-one dihydrochloride (intermediate 10) and 4-chloro-3-(trifluoromethyl)phenyl isocyanate gave the title compound in 61% yield as an off-white powder. MS: 461.2 (MH$^+$, Cl).

Example 15

5-Oxo-4-(3-piperidin-1-yl-propyl)-[1,4]diazepane-1-carboxylic acid (4-fluoro-3-trifluoromethyl-phenyl)-amide

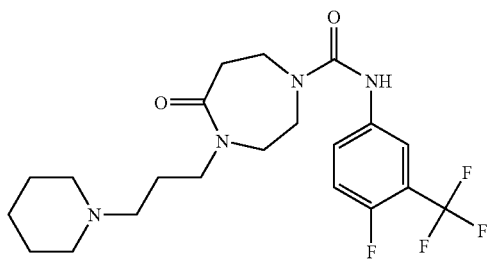

In analogy to the procedure described in Example 1,4-(3-piperidin-1-yl-propyl)-[1,4]diazepan-5-one dihydrochloride (intermediate 10) and 4-fluoro-3-(trifluoromethyl)phenyl isocyanate gave the title compound in 70% yield as an off-white powder. MS: 445.2 (MH$^+$).

Example 16

5-Oxo-4-(3-piperidin-1-yl-propyl)-[1,4]diazepane-1-carboxylic acid (4-trifluoromethyl-phenyl)-amide

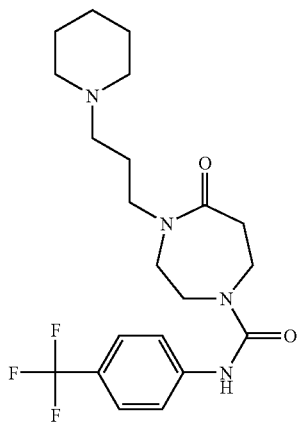

In analogy to the procedure described in Example 1,4-(3-piperidin-1-yl-propyl)-[1,4]diazepan-5-one dihydrochloride (intermediate 10) and 4-(trifluoromethyl)phenyl isocyanate gave the title compound in 79% yield as an off-white powder. MS: 427.3 (MH$^+$).

Example 17

5-Oxo-4-(3-piperidin-1-yl-propyl)-[1,4]diazepane-1-carboxylic acid (4-trifluoromethoxy-phenyl)-amide

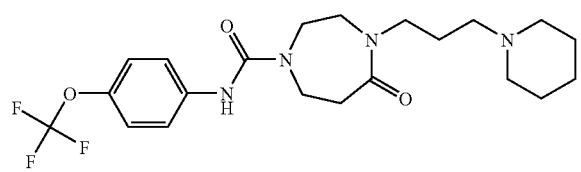

In analogy to the procedure described in Example 1,4-(3-piperidin-1-yl-propyl)-[1,4]diazepan-5-one dihydrochloride (intermediate 10) and 4-(trifluoromethoxy)phenyl isocyanate gave the title compound in 82% yield as an off-white powder. MS: 443.3 (MH$^+$).

Example 18

5-Oxo-4-(3-piperidin-1-yl-propyl)-[1,4]diazepane-1-carbothioic acid (3,4-dichloro-phenyl)-amide

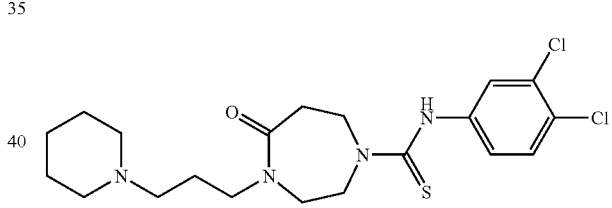

In analogy to the procedure described in Example 1,4-(3-piperidin-1-yl-propyl)-[1,4]diazepan-5-one dihydrochloride (intermediate 10) and 3,4-dichlorophenyl isothiocyanate gave the title compound in 99% yield as an off-white powder. MS:443.3 (MH$^+$, 2Cl).

Example 19

5-Oxo-4-(2-pyrrolidin-1-yl-ethyl)-[1,4]diazepane-1-carboxylic acid (3,4-dichloro-phenyl)-amide

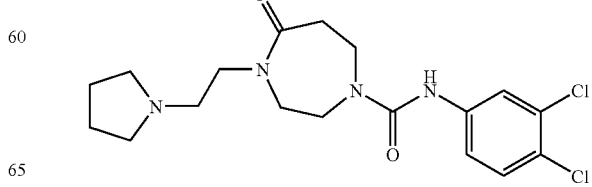

In analogy to the procedure described in Example 1, 4-(2-pyrrolidin-1-yl-ethyl)-[1,4]di-azepan-5-one; dihydrochloride (intermediate 11) and 3,4-dichlorophenyl isocyanate gave the title compound in 60% yield as an off-white powder. MS: 399.5 (MH+, 2Cl).

Example 20

3-Oxo-4-(2-pyrrolidin-1-yl-ethyl)-piperazine-1-carboxylic acid (3,4-dichloro-phenyl)-amide

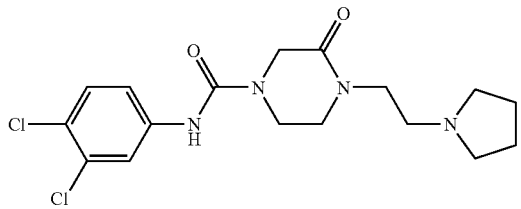

In analogy to the procedure described in Example 1, 1-(2-pyrrolidin-1-yl-ethyl)-piperazin-2-one-dihydrochloride (intermediate 12) and 3,4-dichlorophenyl isocyanate gave the title compound in 72% yield as an off-white powder. MS: 385.5 (MH+, 2Cl).

Example 21

1,1-Dioxo-2-(3-piperidin-1-yl-propyl)-[1,2,5]thiadiazepane-5-carboxylic acid (3,4-dichloro-phenyl)-amide

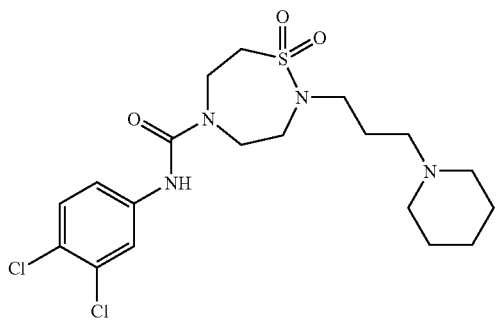

A solution of 3,4-dichlorophenyl isocyanate (59 mg, 0.31 mmol) in tetrahydrofuran (0.5 ml) was added dropwise at room temperature to a suspension of 2-(3-piperidin-1-yl-propyl)-[1,2,5]thiadiazepane 1,1-dioxide dihydrochloride (intermediate 13; 100 mg, 0.29 mmol) and triethylamine (116 mg, 1.15 mmol) in tetrahydrofuran (2 ml). The reaction mixture was stirred for 16 h, then partitioned between sat. aq. ammonium chloride solution and ethyl acetate. The organic layer was dried (MgSO4), filtered, and evaporated. Chromatography (SiO2; dichloro-methane/methanol/25% aq. ammonia solution 95:5:0.25) produced the title compound (117 mg, 88%). White solid, MS (ISP)=463.0 (M+H)+.

Example 22

1,1-Dioxo-2-(3-piperidin-1-yl-propyl)-[1,2,5]thiadiazepane-5-carbothioic acid (3,4-dichloro-phenyl)-amide

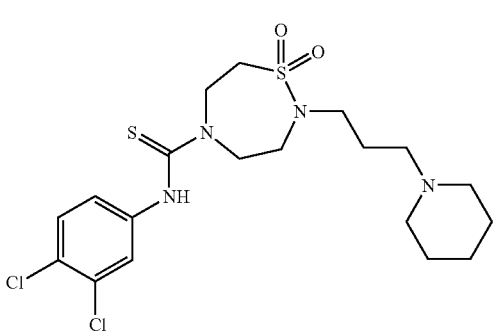

The title compound was produced in analogy to example 21 from 2-(3-piperidin-1-yl-propyl)-[1,2,5]thiadiazepane 1,1-dioxide dihydrochloride (intermediate 13) and 3,4-dichlorophenyl isothiocyanate. Colorless oil, MS (ISP)=479.0 (M+H)+.

Example 23

6-Methyl-5-oxo-4-(3-piperidin-1-yl-propyl)-[1,4]diazepane-1-carboxylic acid (3,4-dichloro-phenyl)-amide

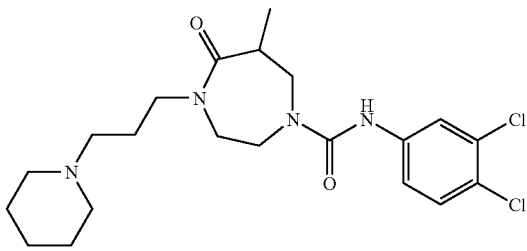

The title compound was produced in analogy to example 21 from 6-methyl-4-(3-piperidin-1-yl-propyl)-[1,4]diazepan-5-one dihydrochloride (intermediate 14) and 3,4-dichlorophenyl isocyanate. White solid, MS (ISP)=441.2 (M+H)+.

Example 24

6-Methyl-5-oxo-4-(3-piperidin-1-yl-propyl)-[1,4]diazepane-1-carbothioic acid (3,4-dichloro-phenyl)-amide

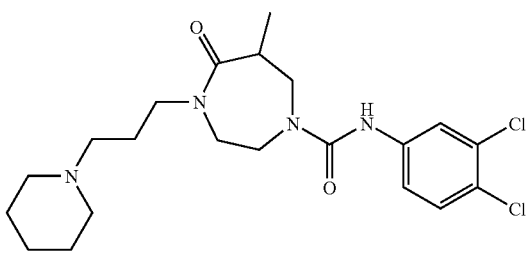

The title compound was produced in analogy to example 21 from 6-methyl-4-(3-piperidin-1-yl-propyl)-[1,4]diazepan-5-one dihydrochloride (intermediate 14) and 3,4-dichlorophenyl isothiocyanate. White foam, MS (ISP)=457.2 (M+H)+.

Example 25

(R)-2-Methyl-5-oxo-4-(3-piperidin-1-yl-propyl)-[1,4]diazepane-1-carboxylic acid (3,4-dichloro-phenyl)-amide

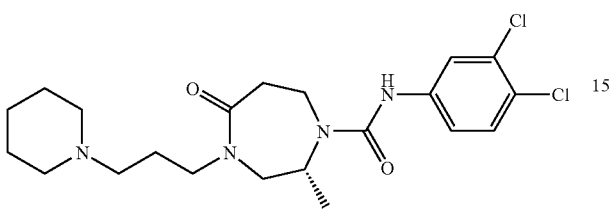

The title compound was produced in analogy to example 21 from (R)-2-methyl-4-(3-piperidin-1-yl-propyl)-[1,4]diazepan-5-one dihydrochloride (intermediate 15) and 3,4-dichlorophenyl isocyanate. White solid, MS (ISP)=441.2 (M+H)+.

Example 26

(R)-2-Methyl-5-oxo-4-(3-piperidin-1-yl-propyl)-[1,4]diazepane-1-carbothioic acid (3,4-dichloro-phenyl)-amide

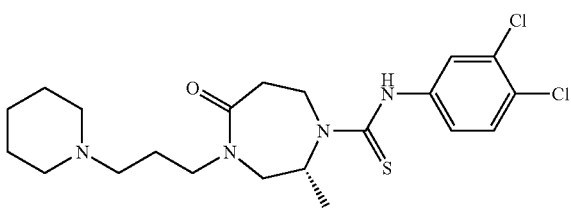

The title compound was produced in analogy to example 21 from (R)-2-methyl-4-(3-piperidin-1-yl-propyl)-[1,4]diazepan-5-one dihydrochloride (intermediate 15) and 3,4-dichlorophenyl isothiocyanate. White solid, MS (ISP)=457.2 (M+H)+.

Example 27

(R)-2-Benzyl-5-oxo-4-(3-piperidin-1-yl-propyl)-[1,4]diazepane-1-carboxylic acid (3,4-dichloro-phenyl)-amide

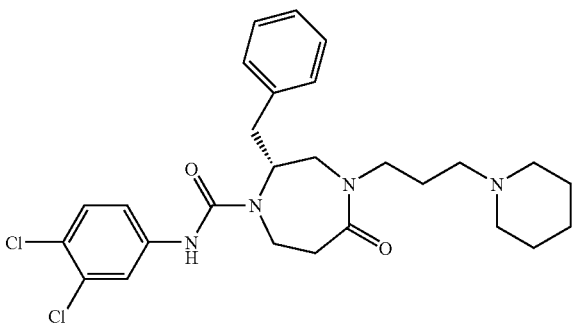

The title compound was produced from (R)-2-benzyl-5-oxo-4-(3-piperidin-1-yl-propyl)-[1,4]diazepane-1-carboxylic acid tert-butyl ester (intermediate 16) by Boc-deprotection in analogy with intermediate 10B, followed by reaction with 3,4-dichlorophenyl isocyanate in analogy with example 21. Colorless oil, MS (ISP)=517.4 (M+H)+.

Example 28

(R)-5-Oxo-4-(3-piperidin-1-yl-propyl)-2-(3-trifluoromethyl-benzyl)-[1,4]diazepane-1-carboxylic acid (3,4-dichloro-phenyl)-amide

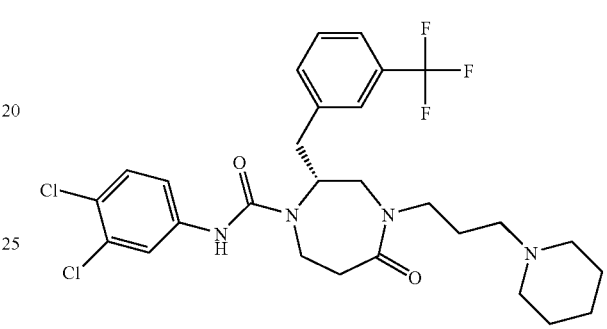

The title compound was produced from (R)-2-(3-trifluoromethyl-benzyl)-5-oxo-4-(3-piperidin-1-yl-propyl)-[1,4]diazepane-1-carboxylic acid tert-butyl ester (intermediate 17) by Boc-deprotection in analogy with intermediate 10B, followed by reaction with 3,4-dichlorophenyl isocyanate in analogy with example 21. Light yellow oil, MS (ISP)=584.7 (M+H)+.

Example 29

(R)-5-Oxo-4-(3-piperidin-1-yl-propyl)-2-(3-trifluoromethyl-benzyl)-[1,4]diazepane-1-carbothioic acid (3,4-dichloro-phenyl)-amide

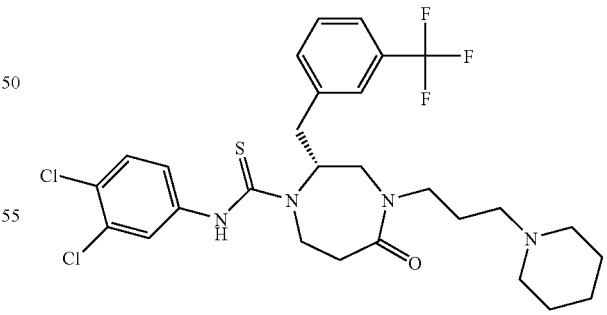

The title compound was produced from (R)-2-(3-trifluoromethyl-benzyl)-5-oxo-4-(3-piperidin-1-yl-propyl)-[1,4] diazepane-1-carboxylic acid tert-butyl ester (intermediate 17) by Boc-deprotection in analogy with intermediate 10B, followed by reaction with 3,4-dichlorophenyl isothiocyanate in analogy with example 21. Light yellow oil, MS (ISP)=600.8 (M+H)+.

Example 30

(R)-5-Oxo-2-phenyl-4-(3-piperidin-1-yl-propyl)-[1,4]diazepane-1-carboxylic acid (3,4-dichloro-phenyl)-amide

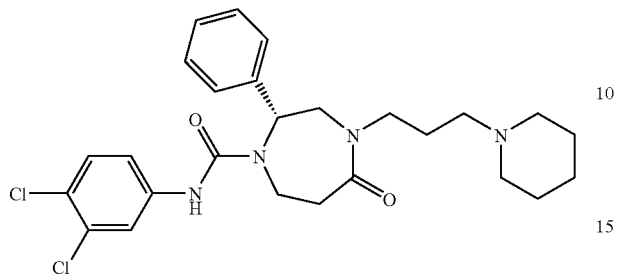

The title compound was produced from (R)-2-phenyl-5-oxo-4-(3-piperidin-1-yl-propyl)-[1,4]diazepane-1-carboxylic acid tert-butyl ester (intermediate 18) by Boc-deprotection in analogy with intermediate 10B, followed by reaction with 3,4-dichlorophenyl isocyanate in analogy with example 21. Colorless oil, MS (ISP)=503.0 (M+H)$^+$.

Example 31

(R)-5-Oxo-2-phenyl-4-(3-piperidin-1-yl-propyl)-[1,4]diazepane-1-carboxylic acid (3-chloro-phenyl)-amide

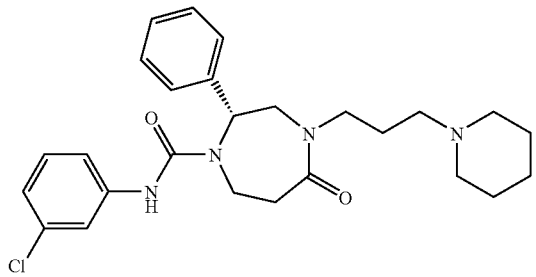

The title compound was produced from (R)-2-phenyl-5-oxo-4-(3-piperidin-1-yl-propyl)-[1,4]diazepane-1-carboxylic acid tert-butyl ester (intermediate 18) by Boc-deprotection in analogy with intermediate 10B, followed by reaction with 3-chlorophenyl isocyanate in analogy with example 21. Colorless oil, MS (ISP)=469.1 (M+H)$^+$.

Example 32

(R)-5-Oxo-2-phenyl-4-(3-piperidin-1-yl-propyl)-[1,4]diazepane-1-carbothioic acid (3,4-dichloro-phenyl)-amide

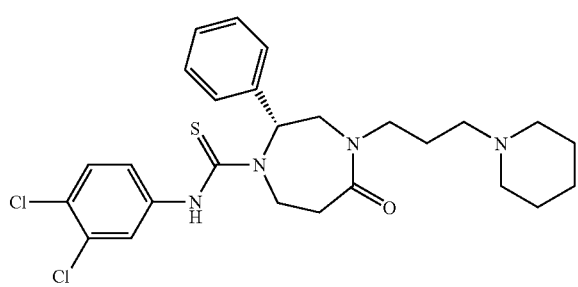

The title compound was produced from (R)-2-phenyl-5-oxo-4-(3-piperidin-1-yl-propyl)-[1,4]diazepane-1-carboxylic acid tert-butyl ester (intermediate 18) by Boc-deprotection in analogy with intermediate 10B, followed by reaction with 3,4-dichlorophenyl isothiocyanate in analogy with example 21. Colorless oil, MS (ISP)=518.9 (M+H)$^+$.

Example 33

(R)-5-Oxo-2-phenethyl-4-(3-piperidin-1-yl-propyl)-[1,4]diazepane-1-carboxylic acid (3,4-dichloro-phenyl)-amide

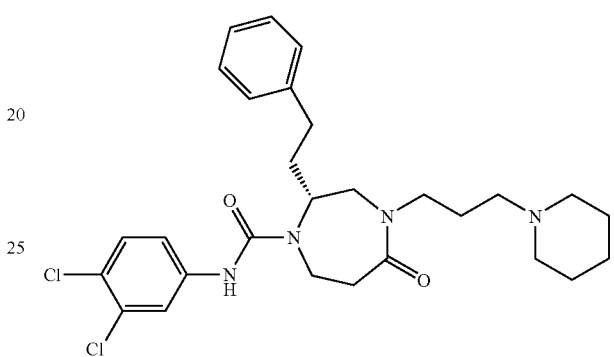

The title compound was produced from (R)-2-phenethyl-5-oxo-4-(3-piperidin-1-yl-propyl)-[1,4]diazepane-1-carboxylic acid tert-butyl ester (intermediate 19) by Boc-deprotection in analogy with intermediate 10B, followed by reaction with 3,4-dichlorophenyl isocyanate in analogy with example 21. Colorless oil, MS (ISP)=530.9 (M+H)$^+$.

Example 34

(R)-5-Oxo-2-phenethyl-4-(3-piperidin-1-yl-propyl)-[1,4]diazepane-1-carbothioic acid (3,4-dichloro-phenyl)-amide

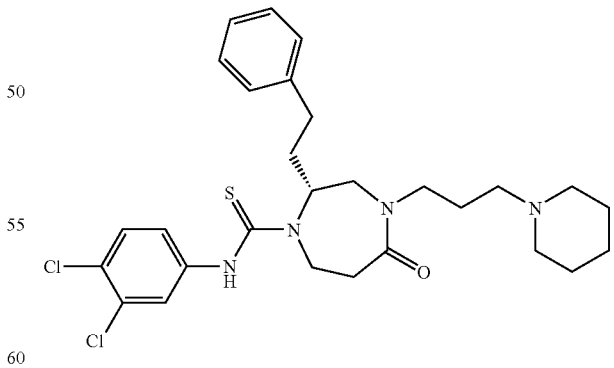

The title compound was produced from (R)-2-phenethyl-5-oxo-4-(3-piperidin-1-yl-propyl)-[1,4]diazepane-1-carboxylic acid tert-butyl ester (intermediate 19) by Boc-deprotection in analogy with intermediate 10B, followed by reaction with 3,4-dichlorophenyl isothiocyanate in analogy with example 21. Colorless oil, MS (ISP)=546.8 (M+H)$^+$.

Example 35

(S)-2-Methyl-3-oxo-4-(3-piperidin-1-yl-propyl)-piperazine-1-carboxylic acid (3-chloro-phenyl)-amide

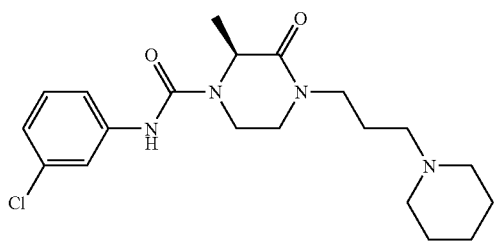

3-Chlorophenyl isocyanate (36 mg, 0.23 mmol) was added to a solution of (S)-3-methyl-1-(3-piperidin-1-yl-propyl)-piperazin-2-one (intermediate 20; 52 mg, 0.21 mmol) and 4-methylmorpholine (21 mg, 0.21 mmol) in N,N-dimethylformamide (1 ml), then after 16 h the reaction mixture was partitioned between ethyl acetate and water. The organic layer was washed with brine, dried (MgSO$_4$), filtered, and evaporated. Chromatography (SiO$_2$; dichloro-methane/methanol/25% aq. ammonia solution 90:10:0.25) produced the title compound (68 mg, 84%). Colorless gum, MS (ISP)=393.2 (M+H)$^+$.

Example 36

(S)-2-Methyl-3-oxo-4-(3-piperidin-1-yl-propyl)-piperazine-1-carboxylic acid (4-chloro-phenyl)-amide

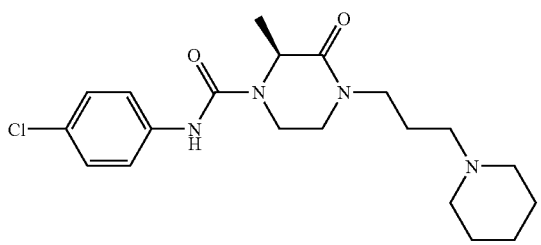

The title compound was produced in analogy to example 35 from (S)-3-methyl-1-(3-piperidin-1-yl-propyl)-piperazin-2-one (intermediate 20) and 4-chlorophenyl isocyanate. Colorless gum, MS (ISP)=393.2 (M+H)$^+$.

Example 37

(S)-2-Methyl-3-oxo-4-(3-piperidin-1-yl-propyl)-piperazine-1-carboxylic acid (3,4-dichloro-phenyl)-amide

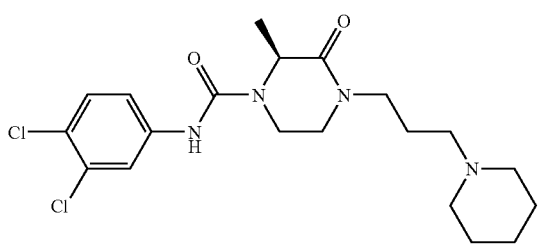

The title compound was produced in analogy to example 35 from (S)-3-methyl-1-(3-piperidin-1-yl-propyl)-piperazin-2-one (intermediate 20) and 3,4-dichlorophenyl isocyanate. Colorless gum, MS (ISP)=427.2 (M+H)$^+$.

Example 38

(S)-2-Methyl-3-oxo-4-(3-piperidin-1-yl-propyl)-piperazine-1-carboxylic acid biphenyl-4-ylamide

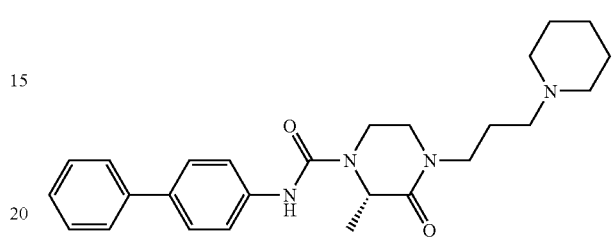

The title compound was produced in analogy to example 35 from (S)-3-methyl-1-(3-piperidin-1-yl-propyl)-piperazin-2-one (intermediate 20) and 4-biphenylyl isocyanate. White solid, MS (ISP)=435.3 (M+H)$^+$.

Example 39

(S)-2-Methyl-3-oxo-4-(3-piperidin-1-yl-propyl)-piperazine-1-carboxylic acid phenylamide

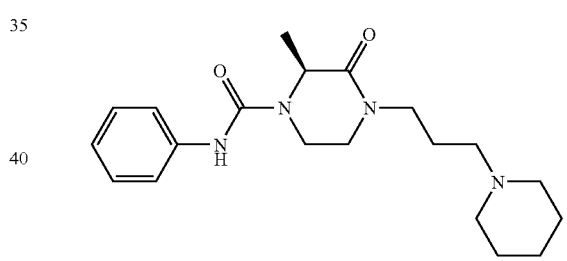

The title compound was produced in analogy to example 35 from (S)-3-methyl-1-(3-piperidin-1-yl-propyl)-piperazin-2-one (intermediate 20) and phenyl isocyanate. Colorless gum, MS (ISP) 359.3 (M+H)$^+$.

Example 40

(S)-2-Methyl-3-oxo-4-(3-piperidin-1-yl-propyl)-piperazine-1-carboxylic acid naphthalen-2-ylamide

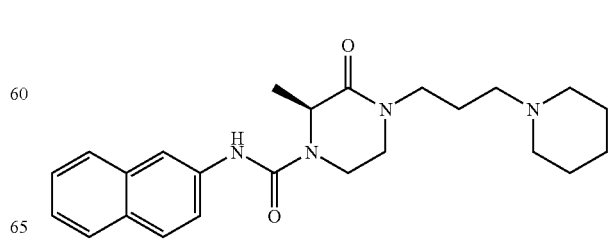

The title compound was produced in analogy to example 35 from (S)-3-methyl-1-(3-piperidin-1-yl-propyl)-piperazin-2-one (intermediate 20) and 2-naphthyl isocyanate. White solid, MS (ISP)=409.3 (M+H)+.

Example 41

(S)-2-Methyl-3-oxo-4-(3-piperidin-1-yl-propyl)-piperazine-1-carboxylic acid (3-trifluoromethyl-phenyl)-amide

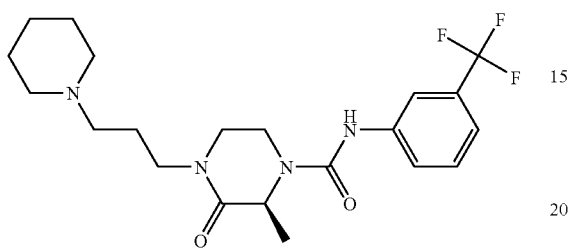

3-(Trifluoromethyl)phenyl isocyanate (30 mg, 0.15 mmol) was added to a solution of (S)-3-methyl-1-(3-piperidin-1-yl-propyl)-piperazin-2-one (intermediate 20; 30 mg, 0.13 mmol) in acetonitrile (1 ml). The solution was heated at 60° C. for 15 min under microwave irradiation, then evaporated. Chromatography (SiO2; dichloromethane/methanol/25% aq. ammonia solution 90:10:0.25) produced the title compound (46 mg, 86%). Colorless gum, MS (ISP)=427.3 (M+H)+.

Example 42

(S)-2-Methyl-3-oxo-4-(3-piperidin-1-yl-propyl)-piperazine-1-carboxylic acid (3-chloro-4-fluoro-phenyl)-amide

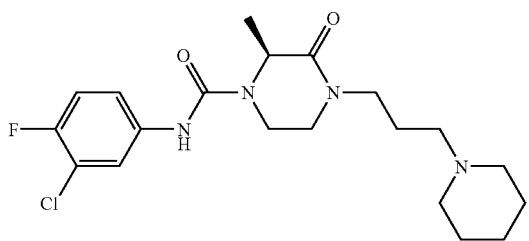

The title compound was produced in analogy to example 41 from (S)-3-methyl-1-(3-piperidin-1-yl-propyl)-piperazin-2-one (intermediate 20) and 3-chloro-4-fluorophenyl isocyanate. Colorless gum, MS (ISP)=411.2 (M+H)+.

Example 43

(S)-2-Methyl-3-oxo-4-(3-piperidin-1-yl-propyl)-piperazine-1-carboxylic acid biphenyl-3-ylamide

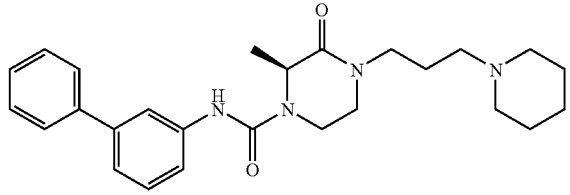

A solution of 3-aminobiphenyl (21 mg, 0.13 mmol) and pyridine (11 mg, 0.14 mmol) in acetonitrile (0.5 ml) was added dropwise at 0° C. to a solution of bis-(trichloromethyl)-carbonate (14 mg, 47 µmol) in acetonitrile (0.5 ml). The reaction mixture was allowed to reach room temperature, then a solution of (S)-3-methyl-1-(3-piperidin-1-yl-propyl)-piperazin-2-one (30 mg, 0.13 mmol) in acetonitrile (0.5 ml) was added dropwise. After 30 min the reaction mixture was evaporated. Chromatography (SiO2; dichloromethane/methanol/25% aq. ammonia solution 90:10:0.25) produced the title compound (36 mg, 66%). Colorless gum, MS (ISP)=435.3 (M+H)+.

Example 44

(S)-2-Methyl-3-oxo-4-(3-piperidin-1-yl-propyl)-piperazine-1-carboxylic acid 3,4-dichloro-phenyl ester

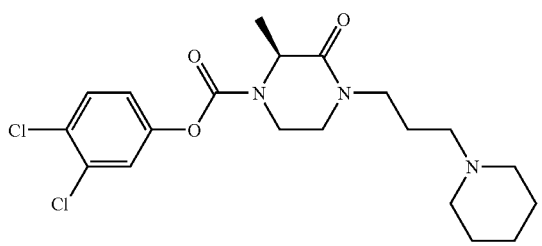

The title compound was produced in analogy to example 7 from (S)-3-methyl-1-(3-piperidin-1-yl-propyl)-piperazin-2-one (intermediate 20) and imidazole-1-carboxylic acid 3,4-dichloro-phenyl ester (intermediate 9). Colorless gum, MS (ISP)=428.2 (M+H)+.

Example 45

(S)-4-[3-((S)-4-Hydroxy-6-aza-spiro[2.5]oct-6-yl)-propyl]-2-methyl-3-oxo-piperazine-1-carboxylic acid (3,4-dichloro-phenyl)-amide

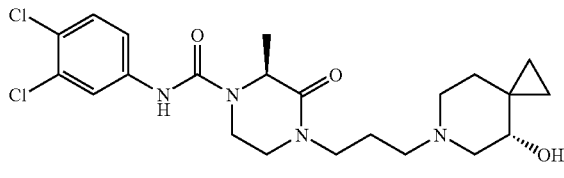

Saturated aq. sodium hydrogencarbonate solution (0.13 ml) was added to a solution of (S)-4-(3-hydroxy-propyl)-2-methyl-3-oxo-piperazine-1-carboxylic acid (3,4-dichloro-phenyl)-amide (intermediate 21; 95 mg, 0.26 mmol), potassium bromide (3 mg, 0.03 mmol), and 2,2,6,6-tetramethylpiperidin-1-oxyl (0.4 mg, 0.003 mmol) in dichloromethane (5 ml). Sodium hypochlorite solution (10% in water, 0.16 ml, 0.26 mmol) was added portionwise at 0° C., and the course of the oxidation was monitored by thin layer chromatography. After all starting material had reacted, the reaction mixture was washed with sat. aq. sodium hydrogencarbonate solution, and the aqueous layer was extracted twice with dichloromethane. The organic phases were pooled, dried (MgSO4), filtered, and evaporated, thus affoding (S)-2-methyl-3-oxo-4-(3-oxo-propyl)-piperazine-1-carboxylic acid (3,4-dichloro-phenyl)-amide (75 mg). This was dissolved in dichloromethane (2 ml) and added over 20 min to a suspension of (S)-6-aza-spiro[2.5]octan-4-ol hydrochloride (intermediate 2; 39 mg, 0.24 mmol) triethylamine (25 mg, 0.25 mmol), acetic acid (29 mg, 0.48 mmol) and sodium triacetoxyborohydride (58 mg, 0.26 mmol) in dichloromethane (2 ml). After 16 h the reaction mixture was treated with 25% aq. ammonia solution (70 μL, 0.48 mmol) and evaporated. Chromatography (SiO$_2$; dichloro-methane/methanol/25% aq. ammonia solution 90:10:0.25) produced the title compound (43 mg, 35%). White solid, MS (ISP)=469.3 (M+H)$^+$.

Example 46

(S)-4-[3-((3S,5S)-3-Hydroxy-5-methyl-piperidin-1-yl)-propyl]-2-methyl-3-oxo-piperazine-1-carboxylic acid (3,4-dichloro-phenyl)-amide

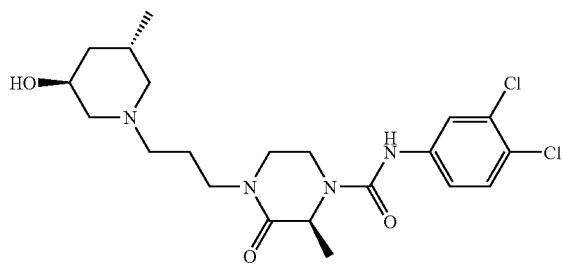

The title compound was produced in analogy to example 45 from (S)-4-(3-hydroxy-propyl)-2-methyl-3-oxo-piperazine-1-carboxylic acid (3,4-dichloro-phenyl)-amide (intermediate 21) and (3S,5S)-5-methyl-piperidin-3-ol hydrochloride (intermediate 4). Colorless gum, MS (ISP)=457.4 (M+H)$^+$.

Example 47

(S)-4-[3-((3S,4S)-3-Hydroxy-4-methyl-piperidin-1-yl)-propyl]-2-methyl-3-oxo-piperazine-1-carboxylic acid (3,4-dichloro-phenyl)-amide

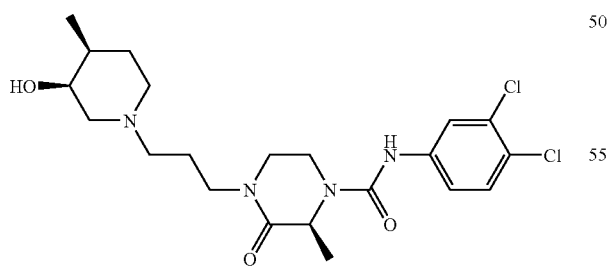

The title compound was produced in analogy to example 45 from (S)-4-(3-hydroxy-propyl)-2-methyl-3-oxo-piperazine-1-carboxylic acid (3,4-dichloro-phenyl)-amide (intermediate 21) and (3S,4S)-4-methyl-piperidin-3-ol hydrochloride (intermediate 4). Colorless gum, MS (ISP)=457.3 (M+H)$^+$.

Example 48

(S)-4-[3-((R)-3-Hydroxy-piperidin-1-yl)-propyl]-2-methyl-3-oxo-piperazine-1-carboxylic acid (3,4-dichloro-phenyl)-amide

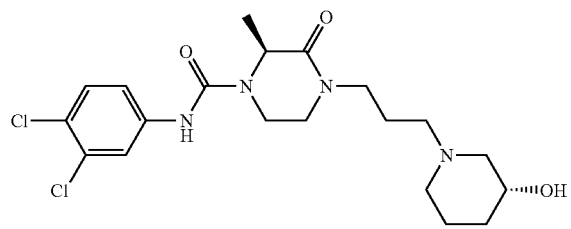

The title compound was produced in analogy to example 45 from (S)-4-(3-hydroxy-propyl)-2-methyl-3-oxo-piperazine-1-carboxylic acid (3,4-dichloro-phenyl)-amide (intermediate 21) and (R)-piperidin-3-ol hydrochloride. Colorless gum, MS (ISP)=443.3 (M+H)$^+$.

Example 49

(S)-4-[3-(4-Hydroxy-piperidin-1-yl)-propyl]-2-methyl-3-oxo-piperazine-1-carboxylic acid (3,4-dichloro-phenyl)-amide

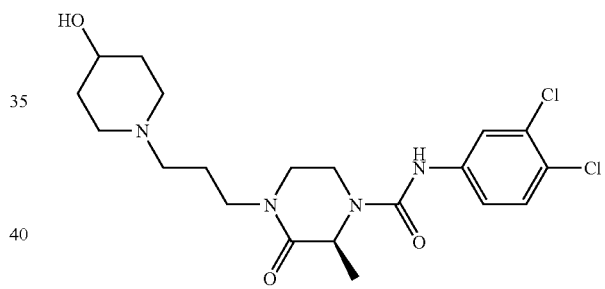

The title compound was produced in analogy to example 45 from (S)-4-(3-hydroxy-propyl)-2-methyl-3-oxo-piperazine-1-carboxylic acid (3,4-dichloro-phenyl)-amide (intermediate 21) and piperidin-4-ol. Colorless gum, MS (ISP)=443.3 (M+H)$^+$.

Example 50

(S)-4-[3-((S)-2-Hydroxymethyl-pyrrolidin-1-yl)-propyl]-2-methyl-3-oxo-piperazine-1-carboxylic acid (3,4-dichloro-phenyl)-amide

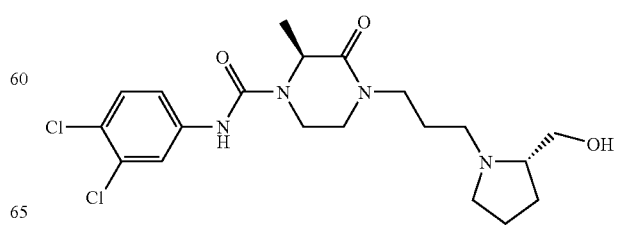

The title compound was produced in analogy to example 45 from (S)-4-(3-hydroxy-propyl)-2-methyl-3-oxo-piperazine-1-carboxylic acid (3,4-dichloro-phenyl)-amide (intermediate 21) and (S)-2-(hydroxymethyl)-pyrrolidine. White solid, MS (ISP)=443.3 (M+H)⁺.

Examples 51 and 52

4-[(S)-3-((S)-4-Hydroxy-6-aza-spiro[2.5]oct-6-yl)-1-hydroxymethyl-propyl]-5-oxo-[1,4]diazepane-1-carboxylic acid 3,4-dichloro-benzylamide and (3,4-dichloro-benzyl)-carbamic acid (S)-2-[4-(3,4-dichloro-benzylcarbamoyl)-7-oxo-[1,4]diazepan-1-yl]-4-((S)-4-hydroxy-6-aza-spiro[2.5]oct-6-yl)-butyl ester

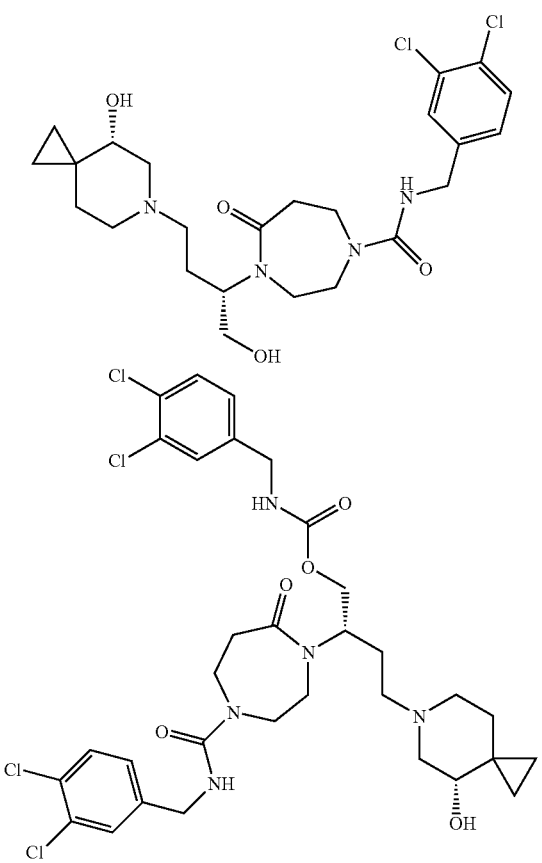

A) 4-[(S)-3-((S)-4-Hydroxy-6-aza-spiro[2.5]oct-6-yl)-1-hydroxymethyl-propyl]-5-oxo-[1,4]diazepane-1-carboxylic acid benzyl ester In analogy to the procedure described in example 2, 4-[(S)-3-((S)-4-hydroxy-6-aza-spiro[2.5]oct-6-yl)-1-methoxycarbonyl-propyl]-5-oxo-[1,4]diazepane-1-carboxylic acid benzyl ester (intermediate 8H) and lithium borohydride gave the title compound in quantitative yield as a white foam. MS; 446.3 (MH⁺).

B) 4-[(S)-3-((S)-4-Hydroxy-6-aza-spiro[2,5]oct-6-yl)-1-hydroxymethyl-propyl]-[1,4]diazepan-5-one In analogy to the procedure described in intermediate 5E, 4-[(S)-3-((S)-4-hydroxy-6-aza-spiro[2.5]oct-6-yl)-1-hydroxymethyl-propyl]-5-oxo-[1,4]diazepane-1-carboxylic acid benzyl ester and 0.1 eq. of 1 M aq. hydrochloric acid solution and Pd/C was hydrogenated to give the title compound in quantitative yield as a white gum. MS: 312.2 (MH⁺).

C) 4-[(S)-3-((S)-4-Hydroxy-6-aza-spiro[2.5]oct-6-yl)-1-hydroxymethyl-propyl]-5-oxo-[1,4]diazepane-1-carboxylic acid 3,4-dichloro-benzylamide and (3,4-dichloro-benzyl)-carbamic acid (S)-2-[4-(3,4-dichloro-benzylcarbamoyl)-7-oxo-[1,4]diazepan-1-yl]-4-((S)-4-hydroxy-6-aza-spiro[2.5]oct-6-yl)-butyl ester In analogy to the procedure described in example 5, 4-[(S)-3-((S)-4-hydroxy-6-aza-spiro[2.5]oct-6-yl)-1-hydroxymethyl-propyl]-[1,4]diazepan-5-one and 3,4-dichlorobenzyl isocyanate (without 4-methylmorpholine) gave after separation with flash chromatography (silicycle SiO₂, dichloromethane/methanol 95:5 to 4:1): 38% of 4-[(S)-3-((S)-4-hydroxy-6-aza-spiro[2.5]oct-6-yl)-1-hydroxymethyl-propyl]-5-oxo-[1,4]diazepane-1-carboxylic acid 3,4-dichloro-benzylamide (example 51) as light yellow oil, MS: 513.3 (MH⁺, 2Cl) and 16% of (3,4-dichloro-benzyl)-carbamic acid (S)-2-[4-(3,4-dichloro-benzylcarbamoyl)-7-oxo-[1,4]diazepan-1-yl]-4-((S)-4-hydroxy-6-aza-spiro[2.5]oct-6-yl)-butyl ester (example 52) as light yellow oil, MS: 714.2 (MH⁺, 4Cl).

Example 53

4-[(S)-3-((S)-4-Hydroxy-6-aza-spiro[2.5]oct-6-yl)-1-hydroxymethyl-propyl]-5-oxo-[1,4]diazepane-1-carboxylic acid (3,4-dichloro-phenyl)-amide

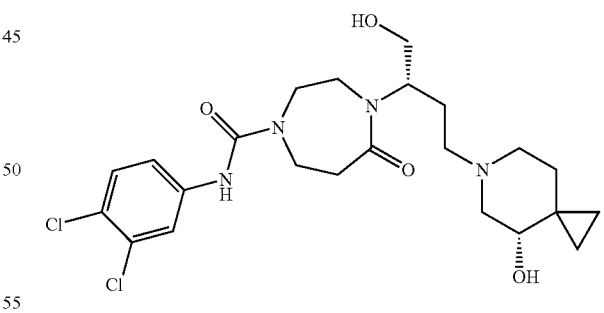

A solution of 0.066 g (0.21 mmol) of 4-[(S)-3-((S)-4-hydroxy-6-aza-spiro[2.5]oct-6-yl)-1-hydroxymethyl-propyl]-[1,4]diazepan-5-one (example 51B) 1.3 ml of N,N-dimethylformamide was treated at room temperature with 0.097 ml (0.70 mmol) of triethylamine and 0.088 ml (0.70 mmol) of chlorotrimethylsilane. The suspension was diluted with 1 ml of dichloromethane and stirred over night at room temperature. A solution of 0.044 g (0.23 mmol) of 3,4-dichlorophenyl isocyanate was added and stirred for 3 h at room temperature. The reaction was evaporated under reduced pressure, redissolved in 2 ml of methanol and 0.2 ml of 1 M aq. hydrochloric acid solution and after 5 min again evaporated. Partitioning between sat. aq. sodium hydrogencarbonate solution and dichloromethane (3×), drying of the organic phase over Na₂SO₄ and purification by flash silica gel column (dichloromethane/methanol 95:5 to 4:1) yielded 0.065 g (61%) of the title compound as yellow foam. MS: 499.2 (MH⁺, 2Cl).

Example 54

4-[3-((S)-4-Hydroxy-6-aza-spiro[2.5]oct-6-yl)-propyl]-5-oxo-[1,4]diazepane-1-carboxylic acid (3,4-dichloro-phenyl)-amide

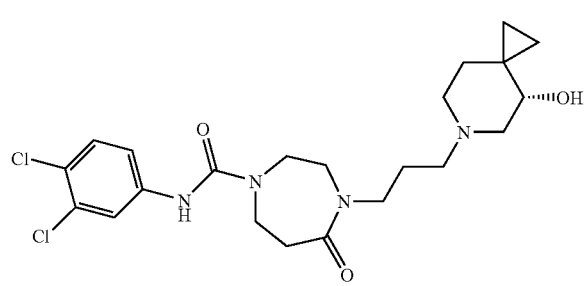

In analogy to the procedure described in example 5, 4-[3-((S)-4-hydroxy-6-aza-spiro[2.5]oct-6-yl)-propyl]-[1,4]diazepan-5-one dihydrochloride (US 2007249589, described as 4-[3-((−)-4-hydroxy-6-aza-spiro[2.5]oct-6-yl)-propyl]-[1,4]diazepan-5-one dihydrochloride) and 3,4-dichlorophenyl isocyanate gave after separation with flash chromatography (silicycle SiO₂, dichloromethane/methanol 95:5 to 4:1) 43% of the title compound as white solid. MS: 469.3 (MH⁺, 2Cl).

Example 55

(R,S)-4-[3-((S)-4-Hydroxy-6-aza-spiro[2.5]oct-6-yl)-1-methoxymethyl-propyl]-5-oxo-[1,4]diazepane-1-carboxylic acid (3,4-dichloro-phenyl)-amide

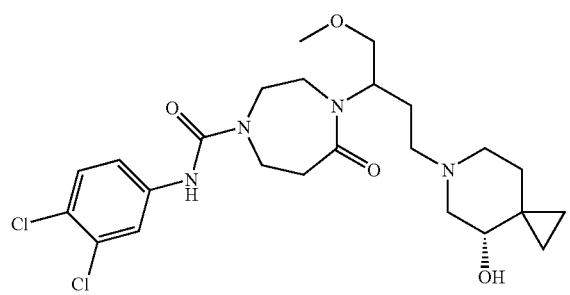

In analogy to the procedure described in example 5, (R,S)-4-[3-((S)-4-hydroxy-6-aza-spiro[2.5]oct-6-yl)-1-methoxymethyl-propyl]-[1,4]diazepan-5-one (intermediate 6) and 3,4-dichlorophenyl isocyanate gave the title compound in 89% yield as an off-white powder. MS: 513.4 (MH⁺, 2Cl).

Examples 56 and 57

4-[(S)-3-((S)-4-Hydroxy-6-aza-spiro[2.5]oct-6-yl)-1-methoxymethyl-propyl]-5-oxo-[1,4]diazepane-1-carboxylic acid (3,4-dichloro-phenyl)-amide and
4-[(R)-3-((S)-4-hydroxy-6-aza-spiro[2.5]oct-6-yl)-1-methoxymethyl-propyl]-5-oxo-[1,4]diazepane-1-carboxylic acid (3,4-dichloro-phenyl)-amide

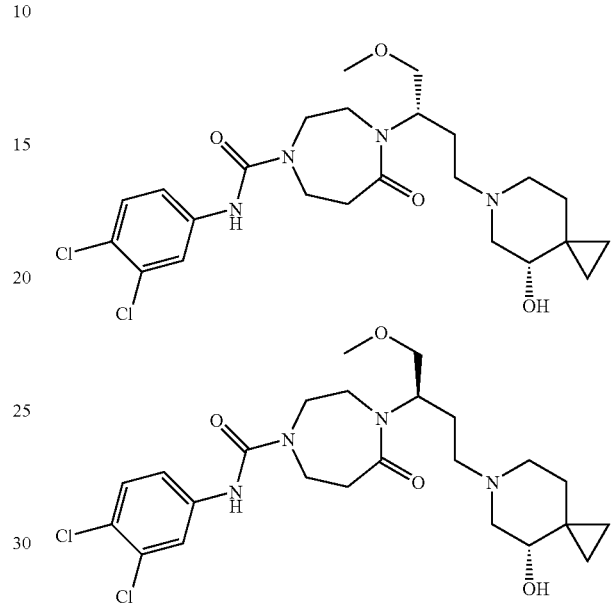

The title compounds were prepared by chiral separation of (R,S)-4-[3-((S)-4-hydroxy-6-aza-spiro[2.5]oct-6-yl)-1-methoxymethyl-propyl]-5-oxo-[1,4]diazepane-1-carboxylic acid (3,4-dichloro-phenyl)-amide (example 55) on a Chiralpak® AD column (heptane/2-propanol 4:1) to give 38% of 4-[(S)-3-((S)-4-hydroxy-6-aza-spiro[2.5]oct-6-yl)-1-methoxymethyl-propyl]-5-oxo-[1,4]diazepane-1-carboxylic acid (3,4-dichloro-phenyl)-amide (example 56) as white powder, MS: 513.4 (MH⁺, 2Cl) and 39% of 4-[(R)-3-((S)-4-hydroxy-6-aza-spiro[2.5]oct-6-yl)-1-methoxymethyl-propyl]-5-oxo-[1,4]diazepane-1-carboxylic acid (3,4-dichloro-phenyl)-amide (example 57) as an off-white powder, MS: 513.4 (MH⁺, 2Cl).

Example 58

(R)-4-[3-((S)-4-Hydroxy-6-aza-spiro[2.5]oct-6-yl)-propyl]-2-methyl-5-oxo-[1,4]diazepane-1-carboxylic acid (3,4-dichloro-phenyl)-amide

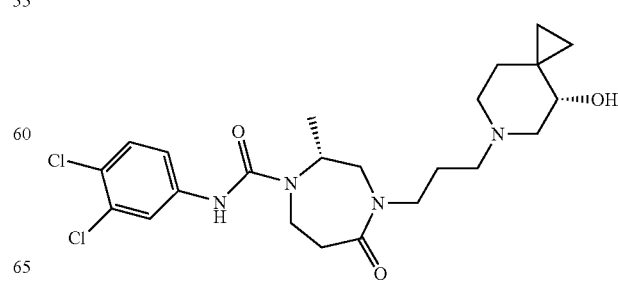

A) (R)-4-(3-Benzyloxy-propyl)-2-methyl-5-oxo-[1,4]diazepane-1-carboxylic acid tert-butyl ester A solution of 0.940 g (4.12 mmol) of (R)-2-methyl-5-oxo-[1,4]diazepane-1-carboxylic acid tert-butyl ester (intermediate 15B) in 20 ml tetrahydrofuran was treated at 0° C. with 0.555 g (4.94 mmol, 1.2 eq.) of potassium tert-butylate and after 20 min slowly with 0.800 ml (4.53 mmol, 1.1 eq.) of benzyl 3-bromopropylether in 5 ml tetrahydrofuran. After 30 min, the solution was warmed to room temperature and stirred overnight. The reaction was slowly added to a solution of sat. aq. sodium hydrogencarbonate, followed by extraction with ethyl acetate (3 times). The organic phases were washed with a solution of sat. aq. sodium hydrogencarbonate and with 10% aq. sodium chloride solution. The combined organic phases were dried over $Na_2SO_4$ and the solvent was removed under vacuum. The crude product was purified by flash chromatography (20 g $SiO_2$-column, ethyl acetate/n-heptane 1:4, 1:1, 3:1) to give 1.319 g (85%) of the title compound as light yellow oil. MS: 377.3 ($MH^+$).

B) (R)-4-(3-Hydroxy-propyl)-2-methyl-5-oxo-[1,4]diazepane-1-carboxylic acid tert-butyl ester A solution of 0.650 g (1.73 mmol) of (R)-4-(3-benzyloxy-propyl)-2-methyl-5-oxo-[1,4]diazepane-1-carboxylic acid tert-butyl ester (example 1A) in 30 ml methanol was treated with 0.065 g of Pd/C (10%) and was stirred over $H_2$-atmosphere over night. After filtration, the solution was evaporated, reevaporated (3 times) with toluene and the solvent was removed under vacuum to give 0.485 g (98%) of the title compound as colorless oil. MS: 287.1 ($MH^+$).

C) (R)-2-Methyl-5-oxo-4-(3-oxo-propyl)-[1,4]diazepane-1-carboxylic acid tert-butyl ester To a solution of 0.161 ml (1.84 mmol, 1.15 eq.) of oxalyl chloride in 9 ml dichloro-methane at −50 to −60° C. was added a solution of 0.272 ml (3.83 mmol, 2.4 eq.) dimethylsulfoxide in 1.5 ml dichloromethane within 5 min. The solution was stirred for 5 min and a solution of 0.457 g (1.60 mmol) of (R)-4-(3-hydroxy-propyl)-2-methyl-5-oxo-[1,4]diazepane-1-carboxylic acid tert-butyl ester (example 1B) in 4.5 ml dichloromethane was added within 5 min. The mixture was stirred for 15 min and 1.11 ml (7.98 mmol, 5 eq.) of triethylamine was added within 5 min. The suspension was stirred for 3.5 h and slowly warmed to −6° C. The reaction was neutralized with cold 10% aq. potassium dihydrogenphosphate solution (adjusted with solid potassium dihydrogenphosphate to pH 4-5) and extracted with ethyl acetate (3 times). The organic phases were washed with fresh sat. aq. sodium hydrogencarbonate solution and 10% aq. sodium chloride solution, dried over $Na_2SO_4$ and evaporated to give 0.418 g (92%) of the title compound as colorless oil. MS: 285.1 ($MH^+$).

D) (R)-4-[3-((S)-4-Hydroxy-6-aza-spiro[2.5]oct-6-yl)-propyl]-2-methyl-5-oxo-[1,4]diazepane-1-carboxylic acid tert-butyl ester A solution of 0.418 g (1.47 mmol) of (R)-2-methyl-5-oxo-4-(3-oxo-propyl)-[1,4]diazepane-1-carboxylic acid tert-butyl ester (example IC) in 10.5 ml dichloromethane was slowly added to a suspension of 0.241 g (1.47 mmol, 1 eq.) of (S)-6-aza-spiro[2.5]octan-4-ol hydrochloride (intermediate 2), 0.205 ml (1.47, 1 eq.) of triethylamine, 0.168 ml (2.94 mmol, 2 eq.) of acetic acid and 0.353 g (1.62 mmol, 1.1 eq.) of sodium triacetoxyborohydride in 55 ml dichloromethane. After 30 min, the reaction mixture was slowly added to a solution of sat. aq. sodium hydrogencarbonate, followed by extraction with dichloromethane (3 times). The organic phases were washed with a solution of sat. aq. sodium hydrogencarbonate and with 10% aq. sodium chloride solution. The combined organic phases were dried over $Na_2SO_4$ and evaporated to give 0.541 g (88%) of the title compound as white foam. MS: 396.3 ($MH^+$).

E) (R)-4-[3-((S)-4-Hydroxy-6-aza-spiro[2.5]oct-6-yl)-propyl]-2-methyl-[1,4]diazepan-5-one dihydrochloride A solution of 0.500 g (1.26 mmol) of (R)-4-[3-((S)-4-hydroxy-6-aza-spiro[2.5]oct-6-yl)-propyl]-2-methyl-5-oxo-[1,4]diazepane-1-carboxylic acid tert-butyl ester (example ID) in 8 ml of dichloromethane was treated at 0° C. with 3.16 ml (12.64 mmol, 10 eq.) of 4 M hydrogen chloride solution in dioxane. The solution was stirred overnight and warmed up to room temperature. The solution was evaporated, suspended in toluene and evaporated (3 times) to give 0.610 g (quantitative, purity: 76%) of the title compound as white solid. MS: 296.3 ($MH^+$).

F) (R)-4-[3-((S)-4-Hydroxy-6-aza-spiro[2.5]oct-6-yl)-propyl]-2-methyl-5-oxo-[1,4]diazepane-1-carboxylic acid (3,4-dichloro-phenyl)-amide A solution of 0.120 g (purity: 76% corresponds to 0.25 mmol) of (R)-4-[3-((S)-4-hydroxy-6-aza-spiro[2.5]oct-6-yl)-propyl]-2-methyl-[1,4]diazepan-5-one dihydrochloride (example 1E) in 2 ml N,N-dimethylformamide was treated at room temperature with 0.052 g (0.27 mmol, 1.1 eq.) of 3,4-dichlorophenyl isocyanate and 0.136 ml (1.24 mmol, 5 eq.) of 4-methylmorpholine. The reaction was stirred at room temperature overnight. To the solution was added 5 mg (0.02 mmol, 0.1 eq.) of 3,4-dichlorophenyl isocyanate. After 1 h, no starting material was left; the solution was slowly added to a solution of sat. aq. sodium hydrogencarbonate, followed by extraction with ethyl acetate (3 times). The organic phases were washed with a solution of sat. aq. sodium hydrogencarbonate and with 10% aq. sodium chloride solution. The combined organic phases were dried over $Na_2SO_4$ and the solvent was removed under vacuum. The crude product was purified by flash chromatography (20 g $SiO_2$-column, dichloro-methane/methanol 2:98, 5:95, 1:9, 1:4) to give 0.061 g (51%) of the title compound as white solid. MS: 483.4 ($MH^+$, 2Cl).

Example 59

(R)-4-[(S)-3-((S)-4-Hydroxy-6-aza-spiro[2.5]oct-6-yl)-1-methoxycarbonyl-propyl]-2-methyl-5-oxo-[1,4]diazepane-1-carboxylic acid benzyl ester

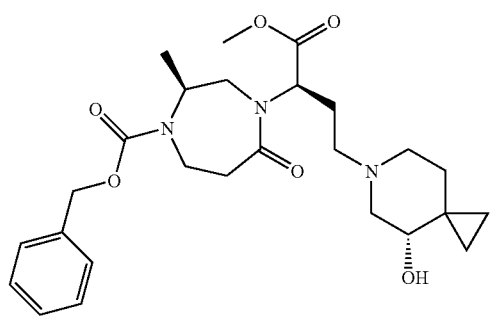

A) 3-[Benzyloxycarbonyl-((R)-2-hydroxy-1-methyl-ethyl)-amino]-propionic acid tert-butyl ester In analogy to the procedure described in intermediate 8A, D-alaninol, tert-butyl-acrylate and N-(benzyloxycarbonyloxy)succinimide gave the title compound in quantitative yield as a light yellow oil. MS: 338.1 (MH$^+$).

B) 3-[Benzyloxycarbonyl-((R)-1-methyl-2-oxo-ethyl)-amino]-propionic acid tert-butyl ester In analogy to the procedure described in intermediate 8B, 3-[benzyloxycarbonyl-((R)-2-hydroxy-1-methyl-ethyl)-amino]-propionic acid tert-butyl ester gave the title compound in 98% yield as yellow oil. MS: 336.1 (MH$^+$).

C) (S)-4-Benzyloxy-2-{(R)-2-[benzyloxycarbonyl-(2-tert-butoxycarbonyl-ethyl)-amino]-propylamino}-butyric acid methyl ester In analogy to the procedure described in example 58D, 3-[benzyloxycarbonyl-((R)-1-methyl-2-oxo-ethyl)-amino]-propionic acid tert-butyl ester and (S)-2-amino-4-benzyloxybutyric acid methyl ester hydrochloride (intermediate 7) gave the title compound in quantitative yield as yellow oil. MS: 543.5 (MH$^+$).

D) (S)-4-Benzyloxy-2-{(R)-2-[benzyloxycarbonyl-(2-carboxy-ethyl)-amino]-propylamino}-butyric acid methyl ester hydrochloride In analogy to the procedure described in intermediate 8D, (S)-4-benzyloxy-2-{(R)-2-[benzyloxycarbonyl-(2-tert-butoxycarbonyl-ethyl)-amino]-propylamino}-butyric acid methyl ester gave the title compound in 98% yield as yellow foam. MS: 487.4 (MH$^+$).

E) (R)-4-((S)-3-Benzyloxy-1-methoxycarbonyl-propyl)-2-methyl-5-oxo-[1,4]diazepane-1-carboxylic acid benzyl ester In analogy to the procedure described in intermediate 8E, (S)-4-benzyloxy-2-{(R)-2-[benzyloxycarbonyl-(2-carboxy-ethyl)-amino]-propylamino}-butyric acid methyl ester hydrochloride gave the title compound in 91% yield as an orange oil. MS: 469.2 (MH$^+$).

F) (R)-4-((S)-3-Hydroxy-1-methoxycarbonyl-propyl)-2-methyl-5-oxo-[1,4]diazepane-1-carboxylic acid benzyl ester In analogy to the procedure described in intermediate 8F, (R)-4-((S)-3-benzyloxy-1-methoxycarbonyl-propyl)-2-methyl-5-oxo-[1,4]diazepane-1-carboxylic acid benzyl ester gave the title compound in 42% yield as light brown gum. MS: 379.1 (MH$^+$).

G) (R)-4-((S)-1-Methoxycarbonyl-3-oxo-propyl)-2-methyl-5-oxo-[1,4]diazepane-1-carboxylic acid benzyl ester In analogy to the procedure described for intermediate 8B, (R)-4-((S)-3-hydroxy-1-methoxycarbonyl-propyl)-2-methyl-5-oxo-[1,4]diazepane-1-carboxylic acid benzyl ester gave the title compound in 92% yield as brown oil. MS: 377.2 (MH$^+$).

H) (R)-4-[(S)-3-((S)-4-Hydroxy-6-aza-spiro[2.5]oct-6-yl)-1-methoxycarbonyl-propyl]-2-methyl-5-oxo-[1,4]diazepane-1-carboxylic acid benzyl ester In analogy to the procedure described for example 58D, (R)-4-((S)-1-methoxycarbonyl-3-oxo-propyl)-2-methyl-5-oxo-[1,4]diazepane-1-carboxylic acid benzyl ester and (S)-6-aza-spiro[2.5]octan-4-ol hydrochloride (intermediate 2) gave the title compound in 42% yield as yellow oil. MS: 488.4 (MH$^+$).

Example 60

(R)-4-[3-((S)-4-Hydroxy-6-aza-spiro[2.5]oct-6-yl)-propyl]-2-methyl-5-oxo-[1,4]diazepane-1-carboxylic acid (3-chloro-phenyl)-amide

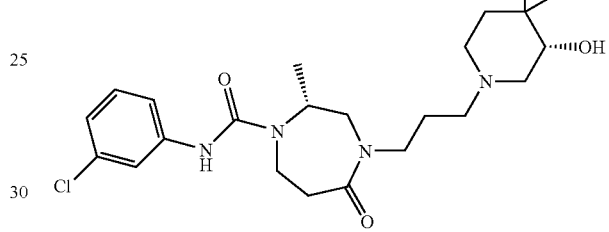

In analogy to the procedure described in example 58F, (R)-4-[3-((S)-4-hydroxy-6-aza-spiro[2.5]oct-6-yl)-propyl]-2-methyl-[1,4]diazepan-5-one dihydrochloride (example 58E) and 3-chlorophenyl isocyanate (without addition of 0.1 eq. of 3-chlorophenyl isocyanate) gave 0.081 g (73%) of the title compound as white foam. MS: 449.3 (MH$^+$, 1Cl).

Example 61

(R)-4-[3-((S)-4-Hydroxy-6-aza-spiro[2.5]oct-6-yl)-propyl]-2-methyl-5-oxo-[1,4]diazepane-1-carboxylic acid (3,4-dimethyl-phenyl)-amide

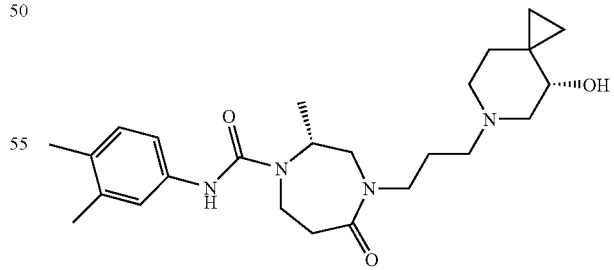

In analogy to the procedure described in example 58F, (R)-4-[3-((S)-4-hydroxy-6-aza-spiro[2.5]oct-6-yl)-propyl]-2-methyl-[1,4]diazepan-5-one dihydrochloride (example 58E) and 3,4-dimethylphenyl isocyanate (without addition of 0.1 eq. of 3,4-dimethylphenyl isocyanate) gave 0.035 g (32%) of the title compound as white foam. MS: 443.3 (MH$^+$).

Example 62

(S)-2-[(R)-4-(3-Chloro-phenylcarbamoyl)-3-methyl-7-oxo-[1,4]diazepan-1-yl]-4-((S)-4-hydroxy-6-aza-spiro[2.5]oct-6-yl)-butyric acid methyl ester

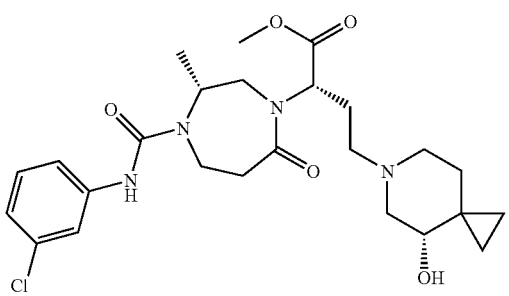

A) (S)-4-((S)-4-Hydroxy-6-aza-spiro[2.5]oct-6-yl)-2-((R)-3-methyl-7-oxo-[1,4]diazepan-1-yl)-butyric acid methyl ester dihydrochloride In analogy to the procedure described in intermediate 5E, (R)-4-[(S)-3-((S)-4-hydroxy-6-aza-spiro[2.5]oct-6-yl)-1-methoxycarbonyl-propyl]-2-methyl-5-oxo-[1,4]diazepane-1-carboxylic acid benzyl ester (example 59) gave after hydrogenation for 6 h the title compound in quantitative yield as white solid. MS: 354.3 (MH$^+$).

B) (S)-2-[(R)-4-(3-Chloro-phenylcarbamoyl)-3-methyl-7-oxo-[1,4]diazepan-1-yl]-4-((S)-4-hydroxy-6-aza-spiro[2.5]oct-6-yl)-butyric acid methyl ester In analogy to the procedure described in example 58F, (S)-4-((S)-4-hydroxy-6-aza-spiro[2.5]oct-6-yl)-2-((R)-3-methyl-7-oxo-[1,4]diazepan-1-yl)-butyric acid methyl ester dihydrochloride and 3-chlorophenyl isocyanate gave the title compound in 59% yield as off-white solid. MS: 506.2 (MH$^+$, 1Cl).

Example 63

(R)-4-[(S)-3-((S)-4-Hydroxy-6-aza-spiro[2.5]oct-6-yl)-1-hydroxymethyl-propyl]-2-methyl-5-oxo-[1,4]diazepane-1-carboxylic acid (3-chloro-phenyl)-amide

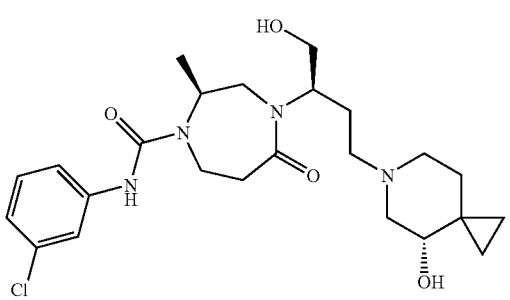

In analogy to the procedure described in intermediate 6A, (S)-2-[(R)-4-(3-chloro-phenylcarbamoyl)-3-methyl-7-oxo-[1,4]diazepan-1-yl]-4-((S)-4-hydroxy-6-aza-spiro[2.5]oct-6-yl)-butyric acid methyl ester was reduced with lithium borohydride (2 h) to give 46% of the title compound as white solid. MS: 479.4 (MH$^+$, 1Cl).

Example 64

(R)-4-[3-((S)-4-Hydroxy-6-aza-spiro[2.5]oct-6-yl)-propyl]-2-methyl-5-oxo-[1,4]diazepane-1-carboxylic acid (3-chloro-2-fluoro-phenyl)-amide

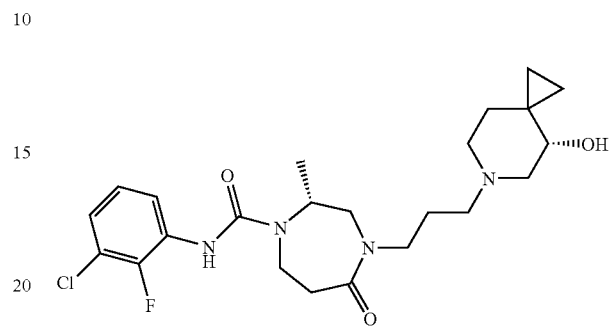

In analogy to the procedure described in example 58F, (R)-4-[3-((S)-4-hydroxy-6-aza-spiro[2.5]oct-6-yl)-propyl]-2-methyl-[1,4]diazepan-5-one dihydrochloride (example 58E) and 3-chloro-2-fluorophenyl isocyanate (but with 2.1 eq. of isocyanate and 5 eq. of 4-methylmorpholine) gave after extraction with sat. aq. sodium hydrogencarbonate solution/1 M aq. sodium hydroxide solution and dichloromethane (3 times) 0.016 g (12%) of the title compound as white foam. MS: 467.2 (MH$^+$, 1Cl).

Example 65

(R)-4-[(S)-3-((S)-4-Hydroxy-6-aza-spiro[2.5]oct-6-yl)-1-methoxymethyl-propyl]-2-methyl-5-oxo-[1,4]diazepane-1-carboxylic acid (3-chloro-phenyl)-amide

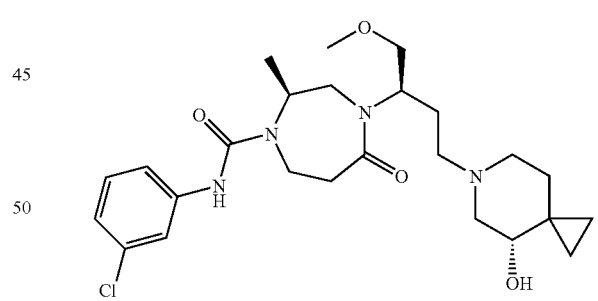

A) (R)-4-((S)-3-Benzyloxy-1-ethoxycarbonyl-propyl)-2-methyl-5-oxo-[1,4]diazepane-1-carboxylic acid benzyl ester In analogy to the procedure described in intermediate 6A, (R)-4-((S)-3-benzyloxy-1-methoxycarbonyl-propyl)-2-methyl-5-oxo-[1,4]diazepane-1-carboxylic acid benzyl ester (example 59E) gave after 2 days and the addition of total 6 eq. of sodium borohydride (instead of lithium borohydride) the corresponding ethyl ester in 87% yield as white solid. MS: 483.4 (MH$^+$).

B) (R)-4-((S)-3-Benzyloxy-1-hydroxymethyl-propyl)-2-methyl-5-oxo-[1,4]diazepane-1-carboxylic acid benzyl ester A solution of 3.90 g (8.10 mmol) of (R)-4-((S)-3-benzyloxy-1-ethoxycarbonyl-propyl)-2-methyl-5-oxo-[1,4]diazepane-1-carboxylic acid benzyl ester in 73 ml of tetrahydrofuran was treated at 0° C. with 4.44 ml (8.90 mmol, 2 M solution in tetrahydrofuran) of lithium borohydride. The reaction was stirred 10 min at 0° C. and 4 h at room temperature, again treated with 3.64 ml (7.30 mmol, 2 M solution in tetrahydrofuran) of lithium borohydride. After 16 h, 5.2 ml of methanol was added and the reaction was neutralized with cold 10% aq. potassium hydrogensulfate solution and extracted with ethyl acetate (3×). The organic phases were washed with 10% aq. potassium hydrogensulfate solution, 10% aq. sodium chloride solution, dried over $Na_2SO_4$ and evaporated to yield after flash silica gel column (ethyl acetate/n-heptane 1:1 to ethyl acetate, then ethyl acetate/methanol 98:2) 2.33 g (65%) of the title compound as off-white oil. MS: 441.4 ($MH^+$).

C) (R)-4-((S)-3-Benzyloxy-1-methoxymethyl-propyl)-2-methyl-5-oxo-[1,4]diazepane-1-carboxylic acid benzyl ester In analogy to the procedure described in intermediate 6B, (R)-4-((S)-3-benzyloxy-1-hydroxymethyl-propyl)-2-methyl-5-oxo-[1,4]diazepane-1-carboxylic acid benzyl ester and methyl iodide gave the title compound in quantitative yield as white oil. MS: 455.4 ($MH^+$).

D) (R)-4-((S)-3-Hydroxy-1-methoxymethyl-propyl)-2-methyl-[1,4]diazepan-5-one hydrochloride In analogy to the procedure described in intermediate 5E, (R)-4-((S)-3-benzyloxy-1-methoxymethyl-propyl)-2-methyl-5-oxo-[1,4]diazepane-1-carboxylic acid benzyl ester and 0.95 eq. of 1 M aq. hydrochloric acid solution was hydrogenated for 6 h to give the title compound in 98% yield as white foam. MS: 231.1 ($MH^+$).

E) (R)-4-((S)-3-Hydroxy-1-methoxymethyl-propyl)-2-methyl-5-oxo-[1,4]diazepane-1-carboxylic acid tert-butyl ester In analogy to the procedure described in intermediate 20E, (R)-4-((S)-3-hydroxy-1-methoxymethyl-propyl)-2-methyl-[1,4]diazepan-5-one hydrochloride, 1 eq. of triethylamine and 1.1 eq. of di-tert-butyl-dicarbonate gave the title compound in 87% yield as a colorless oil. MS: 331.2 ($MH^+$).

F) (R)-4-((S)-1-Methoxymethyl-3-oxo-propyl)-2-methyl-5-oxo-[1,4]diazepane-1-carboxylic acid tert-butyl ester In analogy to the procedure described in intermediate 8B, (R)-4-((S)-3-hydroxy-1-methoxymethyl-propyl)-2-methyl-5-oxo-[1,4]diazepane-1-carboxylic acid tert-butyl ester gave the title compound in 87% yield as yellow oil. MS: 329.2 ($MH^+$).

G) (R)-4-[(S)-3-((S)-4-Hydroxy-6-aza-spiro[2.5]oct-6-yl)-1-methoxymethyl-propyl]-2-methyl-5-oxo-[1,4]diazepane-1-carboxylic acid tert-butyl ester In analogy to the procedure described for example 58D, (R)-4-((S)-1-methoxymethyl-3-oxo-propyl)-2-methyl-5-oxo-[1,4]diazepane-1-carboxylic acid tert-butyl ester and (S)-6-aza-spiro[2.5]octan-4-ol hydrochloride (intermediate 2) gave the title compound in 94% yield as yellow viscous oil. MS: 440.4 ($MH^+$).

H) (R)-4-[(S)-3-((S)-4-Hydroxy-6-aza-spiro[2.5]oct-6-yl)-1-methoxymethyl-propyl]-2-methyl-[1,4]diazepan-5-one dihydrochloride In analogy to the procedure described for intermediate 10B, (R)-4-[(S)-3-((S)-4-hydroxy-6-aza-spiro[2.5]oct-6-yl)-1-methoxymethyl-propyl]-2-methyl-5-oxo-[1,4]diazepane-1-carboxylic acid tert-butyl ester (but without adding methanol) gave the title compound in quantitative yield as off-white solid. MS: 340.2 ($MH^+$).

I) (R)-4-[(S)-3-((S)-4-Hydroxy-6-aza-spiro[2.5]oct-6-yl)-1-methoxymethyl-propyl]-2-methyl-5-oxo-[1,4]diazepane-1-carboxylic acid (3-chloro-phenyl)-amide In analogy to the procedure described for intermediate 58F, (R)-4-[(S)-3-((S)-4-hydroxy-6-aza-spiro[2.5]oct-6-yl)-1-methoxymethyl-propyl]-2-methyl-[1,4]diazepan-5-one dihydrochloride and 3-chlorophenyl isocyanate gave the title compound in 58% yield as yellow oil. MS: 493.4 ($MH^+$, 1Cl).

Example 66

(R)-4-[(S)-3-((S)-4-Hydroxy-6-aza-spiro[2.5]oct-6-yl)-1-methoxymethyl-propyl]-2-methyl-5-oxo-[1,4]diazepane-1-carboxylic acid (3-trifluoromethyl-phenyl)-amide

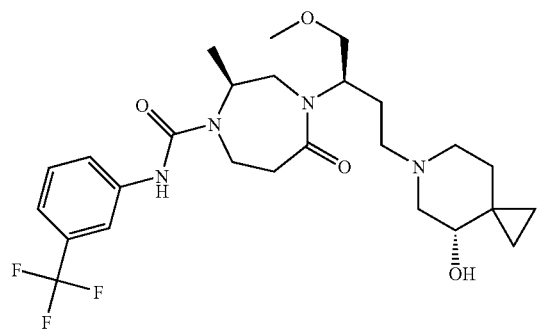

In analogy to the procedure described for intermediate 58F, (R)-4-[(S)-3-((S)-4-hydroxy-6-aza-spiro[2.5]oct-6-yl)-1-methoxymethyl-propyl]-2-methyl-[1,4]diazepan-5-one dihydrochloride (example 65H) and 3-(trifluoromethyl)phenyl isocyanate gave the title compound in 39% yield as orange solid. MS: 527.3 ($MH^+$).

Example 67

(R)-4-[3-((S)-4-Hydroxy-6-aza-spiro[2.5]oct-6-yl)-propyl]-2-methyl-5-oxo-[1,4]diazepane-1-carboxylic acid (5-chloro-2-fluoro-phenyl)-amide

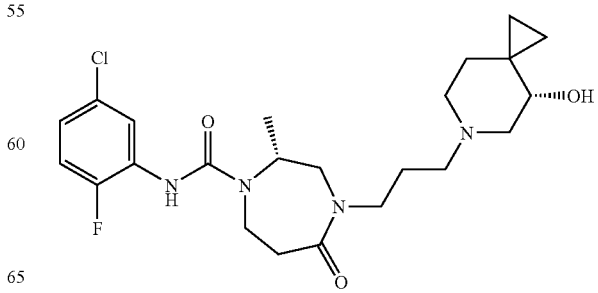

0.022 g (purity: 76% corresponds to 0.04 mmol) of (R)-4-[3-((S)-4-hydroxy-6-aza-spiro[2.5]oct-6-yl)-propyl]-2-methyl-[1,4]diazepan-5-one dihydrochloride (example 58E) was suspended in 1 ml dichloromethane. The reaction mixture was treated at room temperature with 0.031 ml (0.22 mmol, 5 eq.) of triethylamine and at 0° C. with 8 mg (0.05 mmol, 1.1 eq.) 5-chloro-2-fluorophenyl isocyanate. The solution was stirred overnight and warmed up to room temperature. The solution was evaporated. The crude product was purified by flash chromatography (20 g amine-silica, ethyl acetate/n-heptane 1:1, 4:1, 9:1, 100%, ethyl acetate/ethanol 95:5, 9:1) to give 0.010 g (48%) of the title compound as white solid. MS: 467.4 (MH+, Cl).

Example 68

(R)-4-[(S)-3-((S)-4-Hydroxy-6-aza-spiro[2.5]oct-6-yl)-1-methoxymethyl-propyl]-2-methyl-5-oxo-[1,4]diazepane-1-carboxylic acid (3,4-dichloro-phenyl)-amide

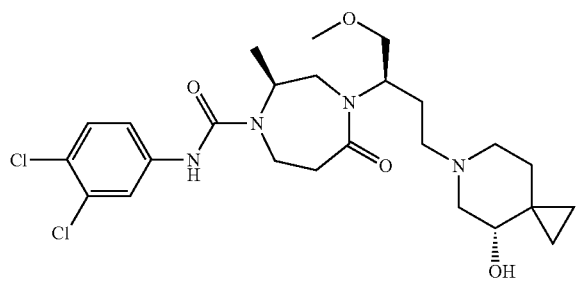

In analogy to the procedure described for intermediate 58F, (R)-4-[(S)-3-((S)-4-hydroxy-6-aza-spiro[2.5]oct-6-yl)-1-methoxymethyl-propyl]-2-methyl-[1,4]diazepan-5-one dihydrochloride (example 65H) and 3,4-dichlorophenyl isocyanate gave the title compound in 74% yield as white solid. MS: 527.2 (MH+, 2Cl).

Example 69

(S)-4-[3-((S)-4-Hydroxy-6-aza-spiro[2.5]oct-6-yl)-propyl]-2-methyl-3-oxo-piperazine-1-carboxylic acid (3-chloro-phenyl)-amide

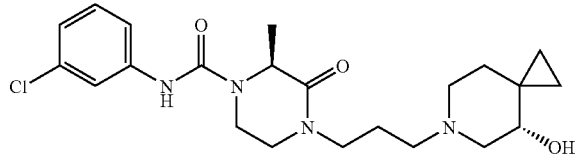

The title compound was produced in analogy to example 35 from (S)-1-[3-((S)-4-hydroxy-6-aza-spiro[2.5]oct-6-yl)-propyl]-3-methyl-piperazin-2-one (intermediate 22) and 3-chlorophenyl isocyanate. White solid, MS (ISP)=435.3 (M+H)+.

Example 70

(S)-4-[3-((S)-4-Hydroxy-6-aza-spiro[2.5]oct-6-yl)-propyl]-2-methyl-3-oxo-piperazine-1-carboxylic acid (3-chloro-4-fluoro-phenyl)-amide

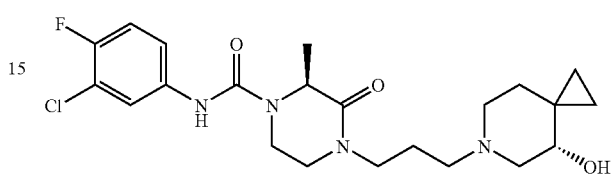

The title compound was produced in analogy to example 35 from (S)-1-[3-((S)-4-hydroxy-6-aza-spiro[2.5]oct-6-yl)-propyl]-3-methyl-piperazin-2-one (intermediate 22) and 3-chloro-4-fluorophenyl isocyanate. White solid, MS (ISP)=453.3 (M+H)+.

Example 71

(S)-4-[3-((S)-4-Hydroxy-6-aza-spiro[2.5]oct-6-yl)-propyl]-2-methyl-3-oxo-piperazine-1-carbothioic acid (3,4-dichloro-phenyl)-amide

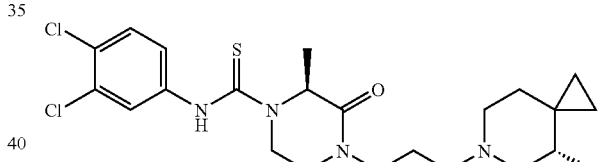

The title compound was produced in analogy to example 35 from (S)-1-[3-((S)-4-hydroxy-6-aza-spiro[2.5]oct-6-yl)-propyl]-3-methyl-piperazin-2-one (intermediate 22) and 3,4-dichlorophenyl isothiocyanate. Colorless gum, MS (ISP)=487.0 (M+H)+.

Example 72

(S)-4-[3-((S)-4-Hydroxy-6-aza-spiro[2.5]oct-6-yl)-propyl]-2-methyl-3-oxo-piperazine-1-carboxylic acid (4-chloro-phenyl)-amide

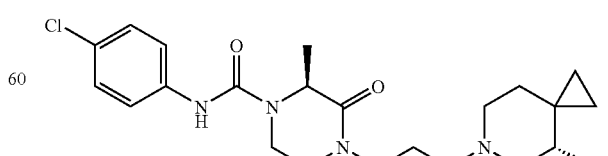

The title compound was produced in analogy to example 35 from (S)-1-[3-((S)-4-hydroxy-6-aza-spiro[2.5]oct-6-yl)- propyl]-3-methyl-piperazin-2-one (intermediate 22) and 4-chlorophenyl isocyanate. White solid, MS (ISP)=435.4 (M+H)+.

Example 73

(S)-4-[3-((S)-4-Hydroxy-6-aza-spiro[2.5]oct-6-yl)-propyl]-2-methyl-3-oxo-piperazine-1-carboxylic acid (3-fluoro-phenyl)-amide

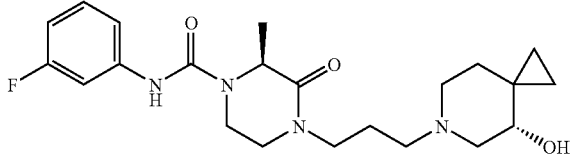

The title compound was produced in analogy to example 35 from (S)-1-[3-((S)-4-hydroxy-6-aza-spiro[2.5]oct-6-yl)-propyl]-3-methyl-piperazin-2-one (intermediate 22) and 3-fluorophenyl isocyanate. White solid, MS (ISP)=419.2 (M+H)+.

Example 74

(S)-4-[3-((S)-4-Hydroxy-6-aza-spiro[2.5]oct-6-yl)-propyl]-2-methyl-3-oxo-piperazine-1-carboxylic acid phenylamide

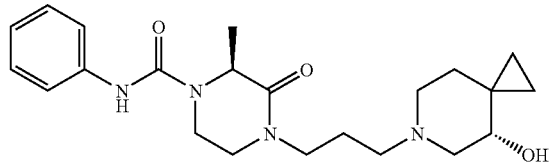

The title compound was produced in analogy to example 35 from (S)-1-[3-((S)-4-hydroxy-6-aza-spiro[2.5]oct-6-yl)-propyl]-3-methyl-piperazin-2-one (intermediate 22) and phenyl isocyanate. White solid, MS (ISP)=401.4 (M+H)+.

Example 75

(S)-4-[3-((S)-4-Hydroxy-6-aza-spiro[2.5]oct-6-yl)-propyl]-2-methyl-3-oxo-piperazine-1-carboxylic acid naphthalen-2-ylamide

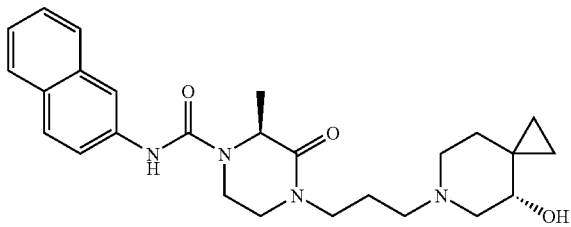

The title compound was produced in analogy to example 35 from (S)-1-[3-((S)-4-hydroxy-6-aza-spiro[2.5]oct-6-yl)-propyl]-3-methyl-piperazin-2-one (intermediate 22) and 2-naphthyl isocyanate. White solid, MS (ISP)=451.2 (M+H)+.

Example 76

(S)-4-[3-((S)-4-Hydroxy-6-aza-spiro[2.5]oct-6-yl)-propyl]-2-methyl-3-oxo-piperazine-1-carboxylic acid biphenyl-4-ylamide

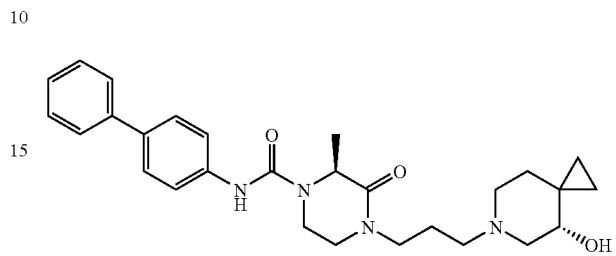

The title compound was produced in analogy to example 35 from (S)-1-[3-((S)-4-hydroxy-6-aza-spiro[2.5]oct-6-yl)-propyl]-3-methyl-piperazin-2-one (intermediate 22) and 4-isocyanato-biphenyl. White solid, MS (ISP)=477.3 (M+H)+.

Example 77

(S)-4-[3-((S)-4-Hydroxy-6-aza-spiro[2.5]oct-6-yl)-propyl]-2-methyl-3-oxo-piperazine-1-carboxylic acid 4-chloro-benzylamide

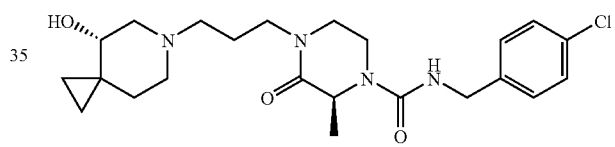

The title compound was produced in analogy to example 35 from (S)-1-[3-((S)-4-hydroxy-6-aza-spiro[2.5]oct-6-yl)-propyl]-3-methyl-piperazin-2-one (intermediate 22) and 4-chlorobenzyl isocyanate. White solid, MS (ISP)=449.3 (M+H)+.

Example 78

(S)-4-[3-((S)-4-Hydroxy-6-aza-spiro[2.5]oct-6-yl)-propyl]-2-methyl-3-oxo-piperazine-1-carboxylic acid biphenyl-3-ylamide

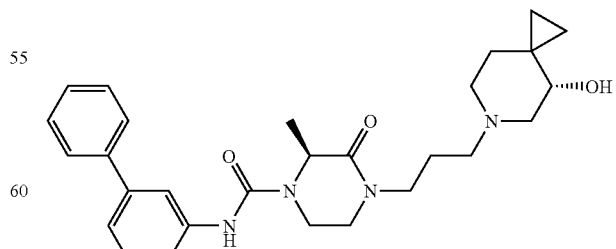

The title compound was produced in analogy to example 43 from (S)-1-[3-((S)-4-hydroxy-6-aza-spiro[2.5]oct-6-yl)-propyl]-3-methyl-piperazin-2-one (intermediate 22) and 3-aminobiphenyl. White solid, MS (ISP)=477.3 (M+H)+.

Example 79

(S)-4-[(S)-3-((S)-4-Hydroxy-6-aza-spiro[2.5]oct-6-yl)-1-methoxymethyl-propyl]-2-methyl-3-oxo-piperazine-1-carboxylic acid (3-chloro-4-fluoro-phenyl)-amide

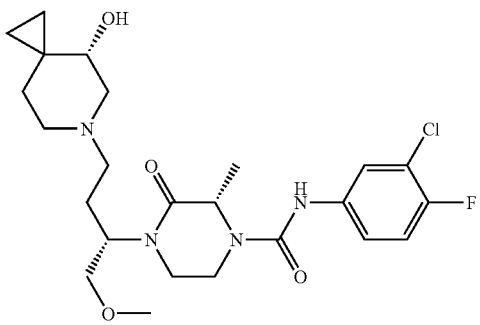

A solution of (S)-4-[(S)-3-((S)-4-hydroxy-6-aza-spiro[2.5]oct-6-yl)-1-methoxymethyl-propyl]-2-methyl-3-oxo-piperazine-1-carboxylic acid tert-butyl ester (intermediate 23; 47 mg, 0.11 mmol) in 1,4-dioxane (0.5 mL) was cooled to 0° C. and treated with hydrogen chloride solution (4 M in 1,4-dioxane, 0.28 mL, 1.1 mmol) The ice bath was removed, the reaction mixture stirred for 4 h, then 4-methylmorpholine (112 mg, 1.1 mmol) and N,N-dimethylformamide (1 mL) were added. To this reaction mixture was added 3-chloro-4-fluorophenyl isocyanate (19 mg 0.11 mmol), then after 16 h the reaction mixture was partitioned between water and ethyl acetate. The aqueous layer was saturated with sodium chloride and extracted with ethyl acetate. The combined organic phases were dried (MgSO$_4$), filtered, and evaporated. Chromatography (SiO$_2$; dichloromethane/methanol/25% aq. ammonia solution gradient 98:2:0.25 to 90:10:0.25) furnished the title compound (52 mg, 95%). Light yellow gum, MS (ISP)=497.3 (M+H)$^+$.

Example 80

(S)-4-[(S)-3-((S)-4-Hydroxy-6-aza-spiro[2.5]oct-6-yl)-1-methoxymethyl-propyl]-2-methyl-3-oxo-piperazine-1-carboxylic acid (3,4-dichloro-phenyl)-amide

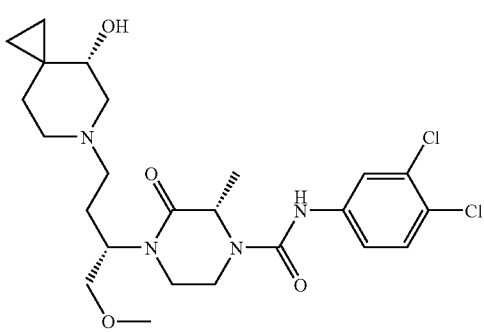

The title compound was produced in analogy to example 79 from (S)-4-[(S)-3-((S)-4-hydroxy-6-aza-spiro[2.5]oct-6-yl)-1-methoxymethyl-propyl]-2-methyl-3-oxo-piperazine-1-carboxylic acid tert-butyl ester (intermediate 23) and 3,4-dichlorophenyl isocyanate. White solid, MS (ISP)=513.3 (M+H)$^+$.

Example 81

(S)-4-((S)-1-Methoxymethyl-3-piperidin-1-yl-propyl)-2-methyl-3-oxo-piperazine-1-carboxylic acid (3,4-dichloro-phenyl)-amide

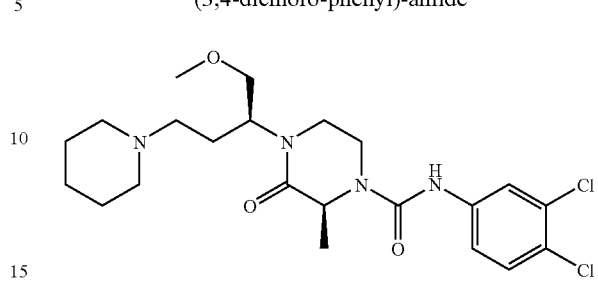

The title compound was produced in analogy to example 79 from (S)-4-((S)-1-methoxy-methyl-3-piperidin-1-yl-propyl)-2-methyl-3-oxo-piperazine-1-carboxylic acid tert-butyl ester (intermediate 24) and 3,4-dichlorophenyl isocyanate. Colorless gum, MS (ISP)=471.2 (M+H)$^+$.

Example 82

(S)-4-[(S)-3-((S)-4-Hydroxy-6-aza-spiro[2.5]oct-6-yl)-1-methoxymethyl-propyl]-2-methyl-3-oxo-piperazine-1-carboxylic acid (3-chloro-phenyl)-amide

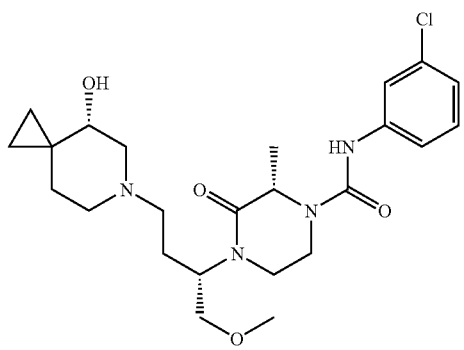

The title compound was produced in analogy to example 79 from (S)-4-[(S)-3-((S)-4-hydroxy-6-aza-spiro[2.5]oct-6-yl)-1-methoxymethyl-propyl]-2-methyl-3-oxo-piperazine-1-carboxylic acid tert-butyl ester (intermediate 23) and 3-chlorophenyl isocyanate. White foam, MS (ISP)=479.2 (M+H)$^+$.

Example 83

(S)-4-[(S)-3-((S)-4-Hydroxy-6-aza-spiro[2.5]oct-6-yl)-1-methoxymethyl-propyl]-2-methyl-3-oxo-piperazine-1-carboxylic acid (3-fluoro-phenyl)-amide

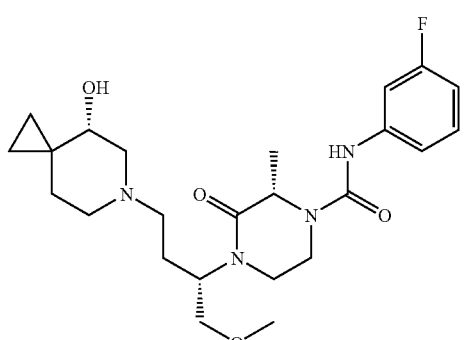

The title compound was produced in analogy to example 79 from (S)-4-[(S)-3-((S)-4-hydroxy-6-aza-spiro[2.5]oct-6-yl)-1-methoxymethyl-propyl]-2-methyl-3-oxo-piperazine-1-carboxylic acid tert-butyl ester (intermediate 23) and 3-fluorophenyl isocyanate. Colorless gum, MS (ISP)=463.3 (M+H)+.

Example 84

(S)-4-[(S)-3-((S)-4-Hydroxy-6-aza-spiro[2.5]oct-6-yl)-1-methoxymethyl-propyl]-2-methyl-3-oxo-piperazine-1-carboxylic acid phenylamide

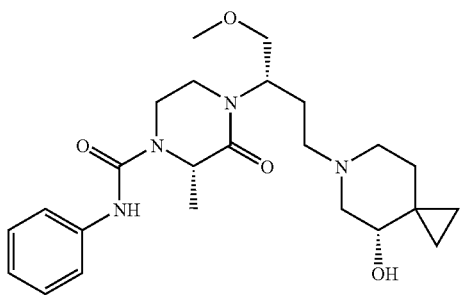

The title compound was produced in analogy to example 79 from (S)-4-[(S)-3-((S)-4-hydroxy-6-aza-spiro[2.5]oct-6-yl)-1-methoxymethyl-propyl]-2-methyl-3-oxo-piperazine-1-carboxylic acid tert-butyl ester (intermediate 23) and phenyl isocyanate. Colorless gum, MS (ISP)=445.3 (M+H)+.

Example 85

(R)-4-[(S)-3-((S)-4-Hydroxy-6-aza-spiro[2.5]oct-6-yl)-1-methoxymethyl-propyl]-2-methyl-3-oxo-piperazine-1-carboxylic acid (3-chloro-phenyl)-amide

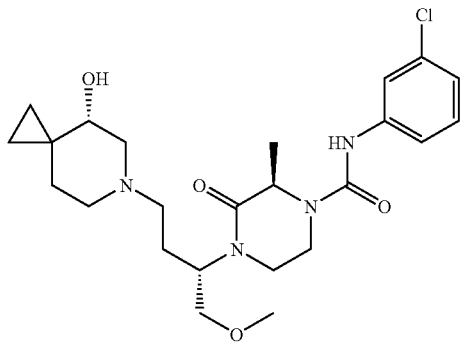

The title compound was produced in analogy to example 79 from (R)-4-[(S)-3-((S)-4-hydroxy-6-aza-spiro[2.5]oct-6-yl)-1-methoxymethyl-propyl]-2-methyl-3-oxo-piperazine-1-carboxylic acid tert-butyl ester (intermediate 25) and 3-chlorophenyl isocyanate. White solid, MS (ISP)=479.2 (M+H)+.

Example 86

(3,4-Dichloro-phenyl)-carbamic acid (S)-2-[(S)-4-(3,4-dichloro-phenylcarbamoyl)-3-methyl-2-oxo-piperazin-1-yl]-4-piperidin-1-yl-butyl ester

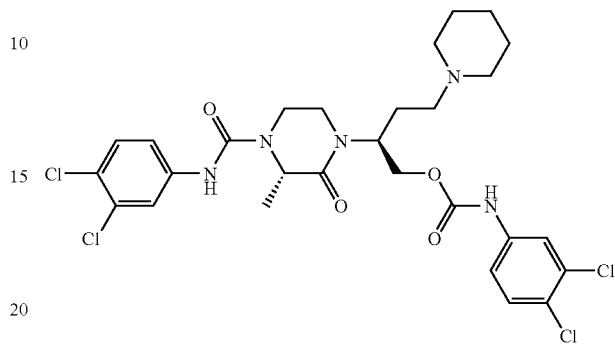

Trifluoroacetic acid (176 mg, 1.54 mmol) was added to a solution of (S)-4-((S)-1-hydroxymethyl-3-piperidin-1-yl-propyl)-2-methyl-3-oxo-piperazine-1-carboxylic acid tert-butyl ester (intermediate 26; 38 mg, 0.10 mmol) in dichloromethane (1 mL), then after 16 h the solution was concentrated in vacuo. The residue was partitioned between dichloromethane and 2 M aq. sodium carbonate solution. The aqueous layer was saturated with sodium chloride and extracted twice with dichloromethane. The combined organic phases were washed with brine, dried (MgSO4), filtered, and evaporated. The residue was taken up in tetrahydrofuran (1 mL), then 3,4-dichlorophenyl isocyanate (20 mg, 0.10 mmol) was added at 0° C., then after 4 h the reaction mixture was partitioned between water and ethyl acetate. The organic layer was washed with brine, dried, and evaporated. Chromatography (SiO2; dichloromethane→dichloromethane/methanol/25% aq. ammonia solution 90:10:0.25 gradient) furnished the title compound (20 mg, 30%). Colorless gum, MS (ISP)=646.2 (M+H)+.

Example 87

(S)-4-[4-((S)-4-Hydroxy-6-aza-spiro[2.5]oct-6-yl)-butyl]-2-methyl-3-oxo-piperazine-1-carboxylic acid (3-chloro-phenyl)-amide

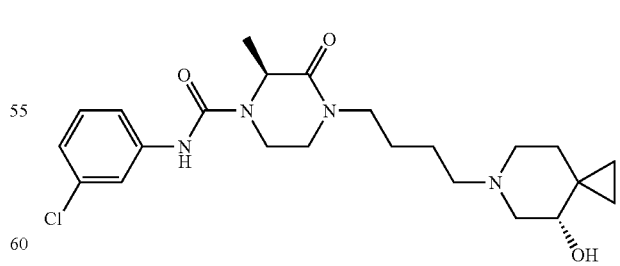

The title compound was produced in analogy to intermediate 21 from (S)-1-[4-((S)-4-hydroxy-6-aza-spiro[2.5]oct-6-yl)-butyl]-3-methyl-piperazin-2-one (intermediate 27) and 3-chlorophenyl isocyanate. Light yellow foam, MS (ISP)=449.3 (M+H)+.

Example 88

(S)-4-[4-((S)-4-Hydroxy-6-aza-spiro[2.5]oct-6-yl)-butyl]-2-methyl-3-oxo-piperazine-1-carboxylic acid (4-trifluoromethyl-phenyl)-amide

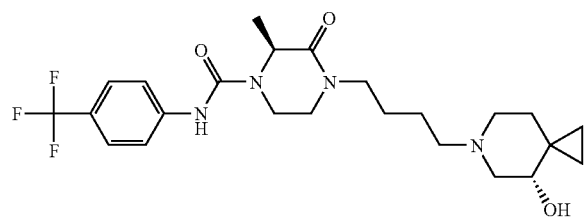

The title compound was produced in analogy to intermediate 21 from (S)-1-[4-((S)-4-hydroxy-6-aza-spiro[2.5]oct-6-yl)-butyl]-3-methyl-piperazin-2-one (intermediate 27) and 4-(trifluoromethyl)phenyl isocyanate. White solid, MS (ISP)=483.5 (M+H)$^+$.

Example 89

(S)-4-[4-((S)-4-Hydroxy-6-aza-spiro[2.5]oct-6-yl)-butyl]-2-methyl-3-oxo-piperazine-1-carboxylic acid (3-trifluoromethyl-phenyl)-amide

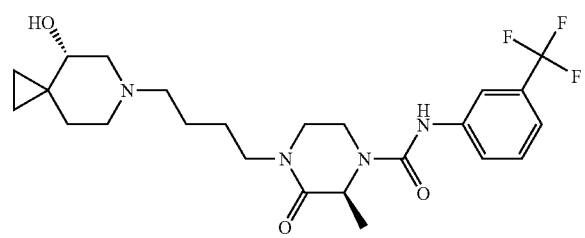

The title compound was produced in analogy to intermediate 21 from (S)-1-[4-((S)-4-hydroxy-6-aza-spiro[2.5]oct-6-yl)-butyl]-3-methyl-piperazin-2-one (intermediate 27) and 3-(trifluoromethyl)phenyl isocyanate. White solid, MS (ISP)=483.5 (M+H)$^+$.

Example 90

(S)-4-[4-((S)-4-Hydroxy-6-aza-spiro[2.5]oct-6-yl)-butyl]-2-methyl-3-oxo-piperazine-1-carboxylic acid (3,4-dichloro-phenyl)-amide

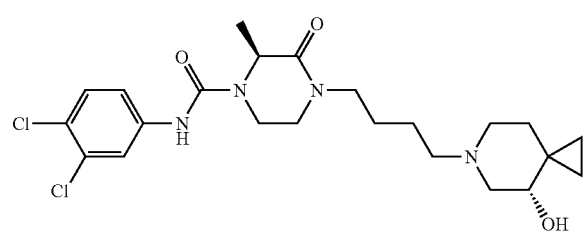

The title compound was produced in analogy to intermediate 21 from (S)-1-[4-((S)-4-hydroxy-6-aza-spiro[2.5]oct-6-yl)-butyl]-3-methyl-piperazin-2-one (intermediate 27) and 3,4-dichlorophenyl isocyanate. Orange oil, MS (ISP)=483.4 (M+H)$^+$.

Example 91

(S)-4-[4-((S)-4-Hydroxy-6-aza-spiro[2.5]oct-6-yl)-butyl]-2-methyl-3-oxo-piperazine-1-carboxylic acid naphthalen-2-ylamide

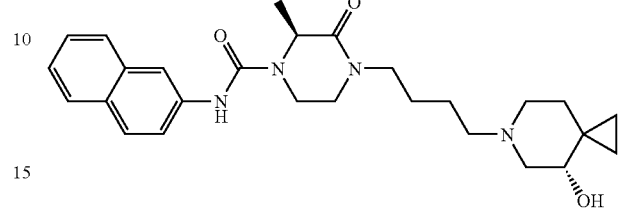

The title compound was produced in analogy to intermediate 21 from (S)-1-[4-((S)-4-hydroxy-6-aza-spiro[2.5]oct-6-yl)-butyl]-3-methyl-piperazin-2-one (intermediate 27) and 2-naphthyl isocyanate. Yellow oil, MS (ISP)=465.5 (M+H)$^+$.

Example 92

(S)-4-[4-((S)-4-Hydroxy-6-aza-spiro[2.5]oct-6-yl)-butyl]-2-methyl-3-oxo-piperazine-1-carbothioic acid O-naphthalen-2-yl ester

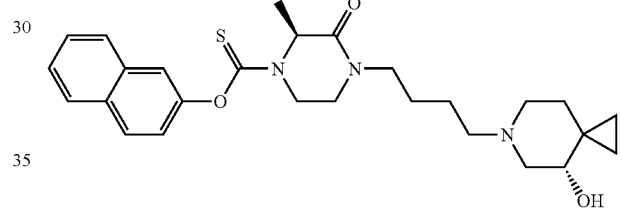

To a solution of (S)-1-[4-((S)-4-hydroxy-6-aza-spiro[2.5]oct-6-yl)-butyl]-3-methyl-piperazin-2-one (intermediate 27; 50 mg, 0.17 mmol) in tetrahydrofuran (0.5 mL) was added at 0° C. O-2-naphthyl chlorothioformate (38 mg, 0.17 mmol) and triethylamine (17 mg, 0.17 mmol). The ice bath was removed, then after 20 min the reaction mixture was cooled to 0° C. and treated with diethylamine (6 mg, 90 µmol), then concentrated under vacuum. Chromatography (SiO$_2$; dichloromethane/methanol/25% aq. ammonia solution 90:10:0.25) furnished the title compound (52 mg, 64%). Orange oil, MS (ISP)=482.4 (M+H)$^+$.

Example 93

(S)-4-[4-((S)-4-Hydroxy-6-aza-spiro[2.5]oct-6-yl)-butyl]-2-methyl-3-oxo-piperazine-1-carboxylic acid biphenyl-3-ylamide

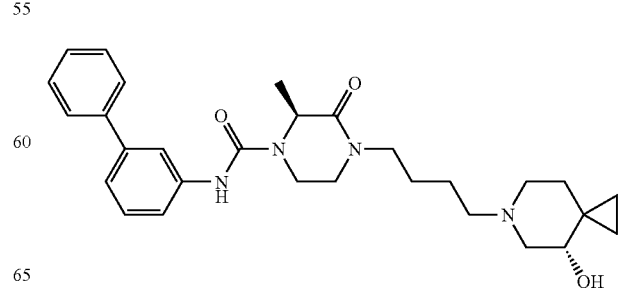

A solution of (S)-1-[4-((S)-4-hydroxy-6-aza-spiro[2.5]oct-6-yl)-butyl]-3-methyl-piperazin-2-one (intermediate 27; 50 mg, 0.17 mmol) and biphenyl-3-ylcarbamic acid phenyl ester (PCT Int. Appl. WO20050443810; 49 mg, 0.17 mmol) in acetonitrile (1 mL) was stirred at room temperature for 72 h, then concentrated under vacuum. Chromatography (SiO$_2$; dichloro-methane/methanol/25% aq. ammonia solution 90:10:0.25) furnished the title compound (69 mg, 83%). White foam, MS (ISP)=491.3 (M+H)$^+$.

Example 94

(S)-4-[4-((S)-4-Hydroxy-6-aza-spiro[2.5]oct-6-yl)-butyl]-2-methyl-3-oxo-piperazine-1-carboxylic acid (3-pyridin-3-yl-phenyl)-amide

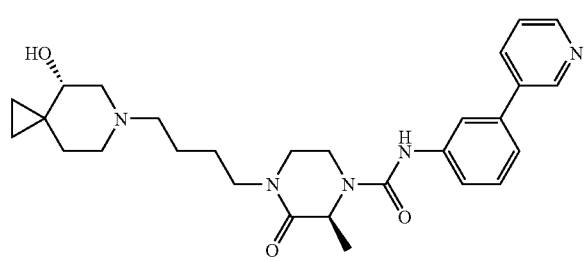

The title compound was produced in analogy to example 93 from (S)-1-[4-((S)-4-hydroxy-6-aza-spiro[2.5]oct-6-yl)-butyl]-3-methyl-piperazin-2-one (intermediate 27) and (3-pyridin-3-yl-phenyl)-carbamic acid phenyl ester (intermediate 28). White foam, MS (ISP)=492.4 (M+H)$^+$.

Example 95

(S)-4-[4-((S)-4-Hydroxy-6-aza-spiro[2.5]oct-6-yl)-butyl]-2-methyl-3-oxo-piperazine-1-carboxylic acid (3-pyridin-4-yl-phenyl)-amide

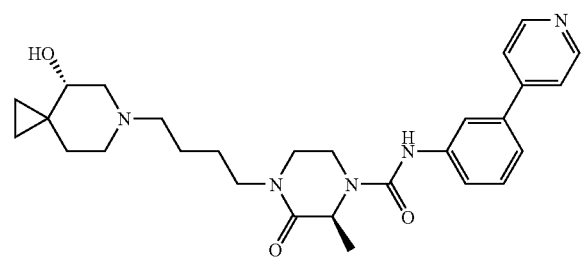

The title compound was produced in analogy to example 93 from (S)-1-[4-((S)-4-hydroxy-6-aza-spiro[2.5]oct-6-yl)-butyl]-3-methyl-piperazin-2-one (intermediate 27) and (3-pyridin-4-yl-phenyl)-carbamic acid phenyl ester (intermediate 29). Off-white foam, MS (ISP)=492.4 (M+H)$^+$.

Example 96

(S)-4-[4-((S)-4-Hydroxy-6-aza-spiro[2.5]oct-6-yl)-butyl]-2-methyl-3-oxo-piperazine-1-carboxylic acid quinolin-6-ylamide

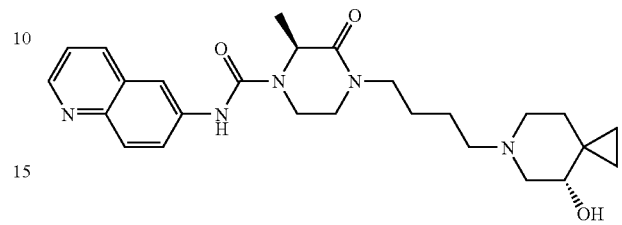

The title compound was produced in analogy to example 93 from (S)-1-[4-((S)-4-hydroxy-6-aza-spiro[2.5]oct-6-yl)-butyl]-3-methyl-piperazin-2-one (intermediate 27) and quinolin-6-yl-carbamic acid phenyl ester (intermediate 30). Light yellow foam, MS (ISP)=466.2 (M+H)$^+$.

Example 97

(S)-4-[4-((S)-4-Hydroxy-6-aza-spiro[2.5]oct-6-yl)-butyl]-2-methyl-3-oxo-piperazine-1-carboxylic acid quinolin-7-ylamide

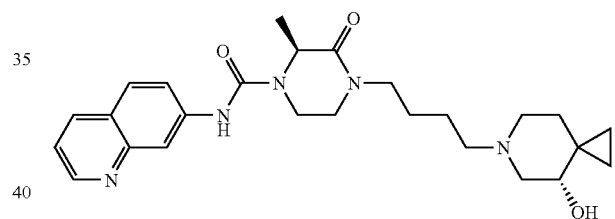

The title compound was produced in analogy to example 93 from (S)-1-[4-((S)-4-hydroxy-6-aza-spiro[2.5]oct-6-yl)-butyl]-3-methyl-piperazin-2-one (intermediate 27) and quinolin-7-yl-carbamic acid phenyl ester (intermediate 31). Light yellow foam, MS (ISP)=466.3 (M+H)$^+$.

Example 98

(S)-4-[4-((S)-4-Hydroxy-6-aza-spiro[2.5]oct-6-yl)-butyl]-2-methyl-3-oxo-piperazine-1-carboxylic acid isoquinolin-7-ylamide

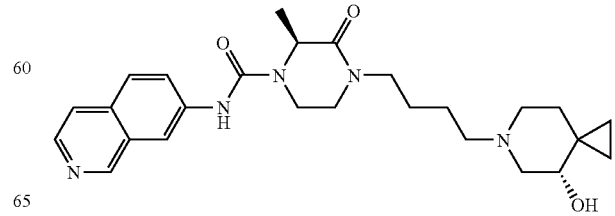

The title compound was produced in analogy to example 93 from (S)-1-[4-((S)-4-hydroxy-6-aza-spiro[2.5]oct-6-yl)-butyl]-3-methyl-piperazin-2-one (intermediate 27) and iso-quinolin-7-yl-carbamic acid phenyl ester (intermediate 32). Light yellow gum, MS (ISP)=466.2 (M+H)⁺.

Example 99

(S)-4-[4-((S)-4-Hydroxy-6-aza-spiro[2.5]oct-6-yl)-butyl]-2-methyl-3-oxo-piperazine-1-carboxylic acid (5-trifluoromethyl-pyridin-2-yl)-amide

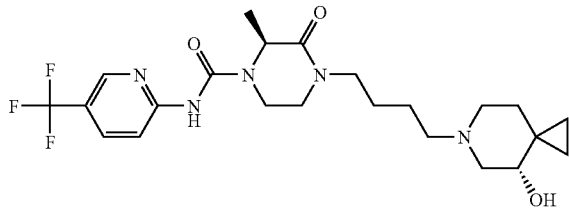

The title compound was produced in analogy to example 93 from (S)-1-[4-((S)-4-hydroxy-6-aza-spiro[2.5]oct-6-yl)-butyl]-3-methyl-piperazin-2-one (intermediate 27) and (5-trifluoromethyl-pyridin-2-yl)-carbamic acid phenyl ester (intermediate 33). Yellow gum, MS (ISP)=484.5 (M+H)⁺.

Example 100

(S)-4-[4-((S)-4-Hydroxy-6-aza-spiro[2.5]oct-6-yl)-butyl]-2-methyl-3-oxo-piperazine-1-carboxylic acid (4-trifluoromethyl-pyridin-2-yl)-amide

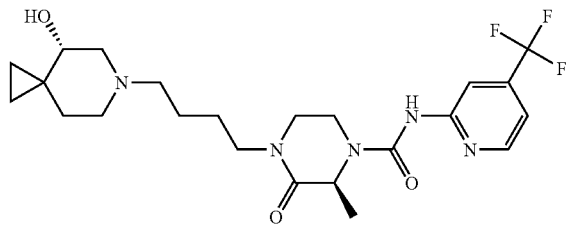

The title compound was produced in analogy to example 93 from (S)-1-[4-((S)-4-hydroxy-6-aza-spiro[2.5]oct-6-yl)-butyl]-3-methyl-piperazin-2-one (intermediate 27) and (4-trifluoromethyl-pyridin-2-yl)-carbamic acid phenyl ester (intermediate 34). Yellow gum, MS (ISP)=484.4 (M+H)⁺.

Example 101

(S)-4-[4-((S)-4-Hydroxy-6-aza-spiro[2.5]oct-6-yl)-butyl]-2-methyl-3-oxo-piperazine-1-carboxylic acid (6-trifluoromethyl-pyridin-2-yl)-amide

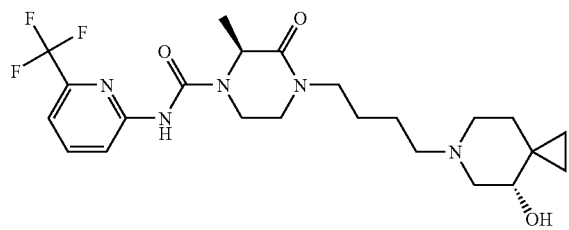

The title compound was produced in analogy to example 93 from (S)-1-[4-((S)-4-hydroxy-6-aza-spiro[2.5]oct-6-yl)-butyl]-3-methyl-piperazin-2-one (intermediate 27) and (6-trifluoromethyl-pyridin-2-yl)-carbamic acid phenyl ester (intermediate 35). Yellow gum, MS (ISP)=484.4 (M+H)⁺.

Example 102

(S)-4-[4-((S)-4-Hydroxy-6-aza-spiro[2.5]oct-6-yl)-butyl]-2-methyl-3-oxo-piperazine-1-carboxylic acid isoquinolin-6-ylamide

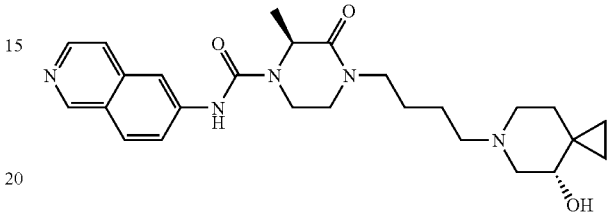

The title compound was produced in analogy to example 93 from (S)-1-[4-((S)-4-hydroxy-6-aza-spiro[2.5]oct-6-yl)-butyl]-3-methyl-piperazin-2-one (intermediate 27) and iso-quinolin-6-yl-carbamic acid phenyl ester (intermediate 36). White solid, MS (ISP)=466.2 (M+H)⁺.

Example 103

(S)-4-[2-((S)-4-Hydroxy-6-aza-spiro[2.5]oct-6-yl)-ethyl]-2-methyl-3-oxo-piperazine-1-carboxylic acid (3-chloro-phenyl)-amide

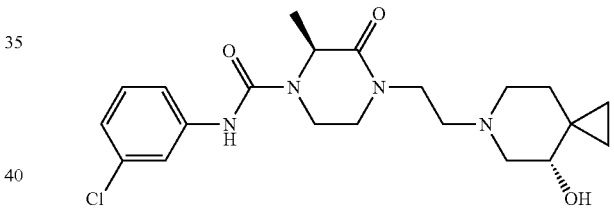

The title compound was produced from (S)-4-[2-((S)-4-hydroxy-6-aza-spiro[2.5]oct-6-yl)-ethyl]-2-methyl-3-oxo-piperazine-1-carboxylic acid benzyl ester (intermediate 37) by hydrogenation in analogy to intermediate 22C, leading to (S)-1-[2-((S)-4-hydroxy-6-aza-spiro[2.5]oct-6-yl)-ethyl]-3-methyl-piperazin-2-one, followed by reaction with 3-chlorophenyl isocyanate in analogy with intermediate 21. Colorless gum, MS (ISP)=421.1 (M+H)⁺.

Example 104

(S)-4-[2-((S)-4-Hydroxy-6-aza-spiro[2.5]oct-6-yl)-ethyl]-2-methyl-3-oxo-piperazine-1-carboxylic acid (3,4-dichloro-phenyl)-amide

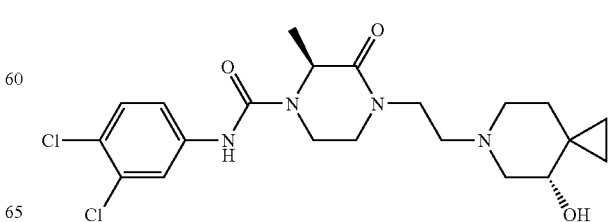

The title compound was produced in analogy to example 103 from (S)-4-[2-((S)-4-hydroxy-6-aza-spiro[2.5]oct-6-yl)-ethyl]-2-methyl-3-oxo-piperazine-1-carboxylic acid benzyl ester (intermediate 37) and 3,4-dichlorophenyl isocyanate. White foam, MS (ISP)=455.3 (M+H)⁺.

Example 105

(S)-4-[3-((S)-4-Hydroxy-6-aza-spiro[2.5]oct-6-ylmethyl)-oxetan-3-ylmethyl]-2-methyl-3-oxo-piperazine-1-carboxylic acid (3,4-dichloro-phenyl)-amide

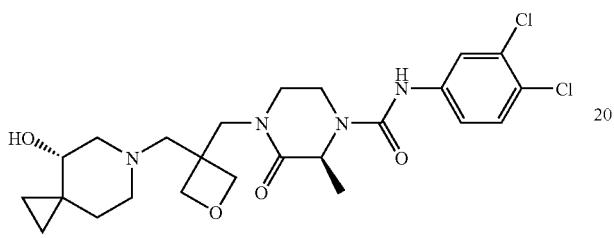

The title compound was produced in analogy to example 103 from (S)-4-[3-((S)-4-hydroxy-6-aza-spiro[2.5]oct-6-ylmethyl)-oxetan-3-ylmethyl]-2-methyl-3-oxo-piperazine-1-carboxylic acid benzyl ester (intermediate 38) and 3,4-dichlorophenyl isocyanate. Colorless gum, MS (ISP)=511.3 (M+H)⁺.

Example 106

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3,4-dichloro-phenyl)-amide

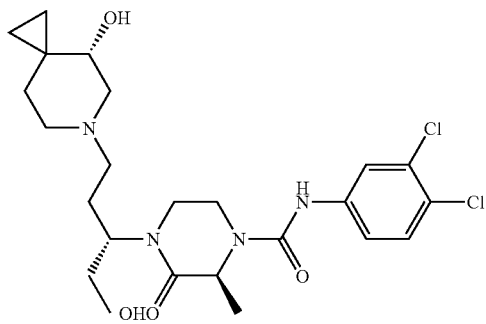

The title compound was produced in analogy to example 103 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and 3,4-dichlorophenyl isocyanate. White foam, MS (ISP)=499.2 (M+H)⁺.

Example 107

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3-chloro-phenyl)-amide

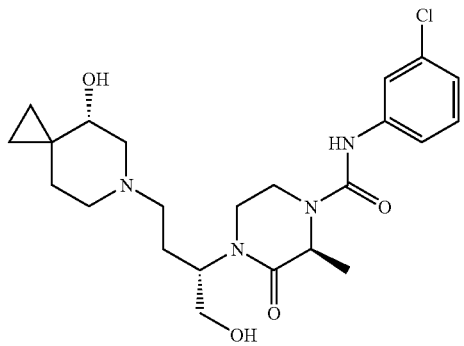

The title compound was produced in analogy to example 103 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and 3-chlorophenyl isocyanate. White solid, MS (ISP)=465.3 (M+H)⁺.

Example 108

Acetic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester

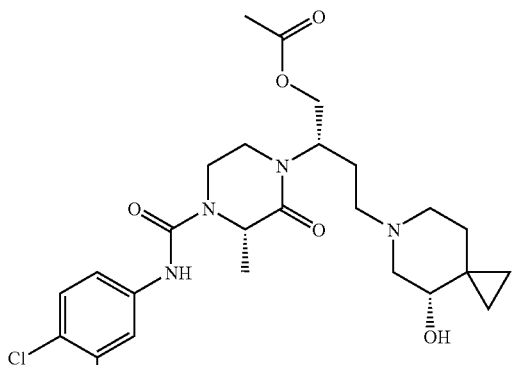

A) (S)-4-[(S)-1-Acetoxymethyl-3-((S)-4-hydroxy-6-aza-spiro[2.5]oct-6-yl)-propyl]-2-methyl-3-oxo-piperazine-1-carboxylic acid benzyl ester Acetic anhydride (42 mg, 0.41 mmol) was added at 0° C. to a solution of (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39; 182 mg, 0.41 mmol) and pyridine (32 mg, 0.41 mmol). The ice bath was removed, then after 16 h excess reagent was destroyed by addition of diethylamine (15 mg, 0.21 mmol). After evaporation of volatile material, chromatography (SiO₂; dichloromethane to dichloromethane/methanol/25% aq. ammonia solution 90:10:0.25) produced the title compound (143 mg, 72%). Colorless gum, MS (ISP)=488.4 (M+H)⁺.

B) Acetic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester The title compound was produced in analogy to example 103 from (S)-4-[(S)-1-acetoxymethyl-3-((S)-4-hydroxy-6-aza-spiro[2.5]oct-6-yl)-propyl]-2-methyl-3-oxo-piperazine-1-carboxylic acid benzyl ester and 3,4-dichlorophenyl isocyanate. White solid, MS (ISP)=541.2 (M+H)+.

Example 109

Acetic acid (S)-2-[(S)-4-(3-chloro-phenylcarbamoyl)-3-methyl-2-oxo-piperazin-1-yl]-4-((S)-4-hydroxy-6-aza-spiro[2.5]oct-6-yl)-butyl ester

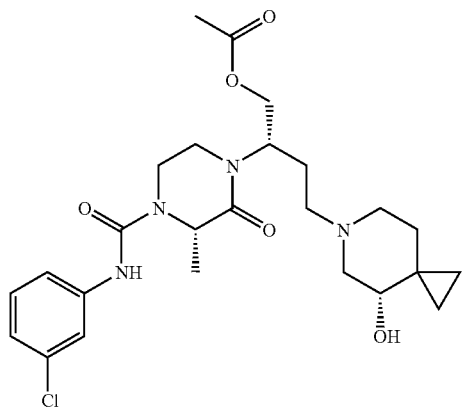

The title compound was produced in analogy to example 103 from (S)-4-[(S)-1-acetoxymethyl-3-((S)-4-hydroxy-6-aza-spiro[2.5]oct-6-yl)-propyl]-2-methyl-3-oxo-piperazine-1-carboxylic acid benzyl ester (example 108A) and 3-chlorophenyl isocyanate. White solid, MS (ISP)=507.3 (M+H)+.

Example 110

Carbonic acid (S)-2-[(S)-4-(3-chloro-phenylcarbamoyl)-3-methyl-2-oxo-piperazin-1-yl]-4-((S)-4-hydroxy-6-aza-spiro[2.5]oct-6-yl)-butyl ester methyl ester

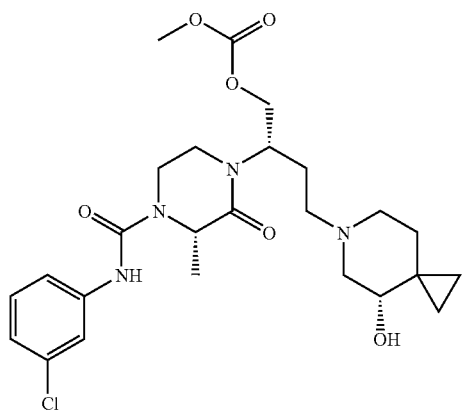

A) (S)-4-[(S)-3-((S)-4-Hydroxy-6-aza-spiro[2.5]oct-6-yl)-1-methoxycarbonyloxymethyl-propyl]-2-methyl-3-oxo-piperazine-1-carboxylic acid benzyl ester The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and methyl chloroformate. Colorless gum, MS (ISP)=504.2 (M+H)+.

B) Carbonic acid (S)-2-[(S)-4-(3-chloro-phenylcarbamoyl)-3-methyl-2-oxo-piperazin-1-yl]-4-((S)-4-hydroxy-6-aza-spiro[2.5]oct-6-yl)-butyl ester methyl ester The title compound was produced in analogy to example 103 from (S)-4-[(S)-3-((S)-4-hydroxy-6-aza-spiro[2.5]oct-6-yl)-1-methoxycarbonyloxymethyl-propyl]-2-methyl-3-oxo-piperazine-1-carboxylic acid benzyl ester and 3-chlorophenyl isocyanate. White solid, MS (ISP)=523.3 (M+H)+.

Example 111

Ethyl-carbamic acid (S)-2-[(S)-4-(3-chloro-phenylcarbamoyl)-3-methyl-2-oxo-piperazin-1-yl]-4-((S)-4-hydroxy-6-aza-spiro[2.5]oct-6-yl)-butyl ester

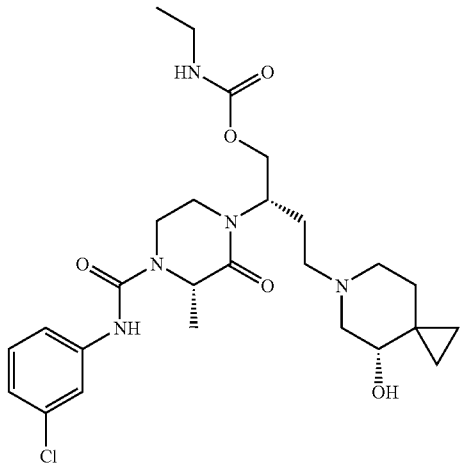

A) (S)-4-[(S)-1-Ethylcarbamoyloxymethyl-3-((S)-4-hydroxy-6-aza-spiro[2.5]oct-6-yl)-propyl]-2-methyl-3-oxo-piperazine-1-carboxylic acid benzyl ester To a solution of (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39; 63 mg, 0.14 mmol) in acetonitrile (1 mL) was added ethyl isocyanate (11 mg, 0.14 mmol) at 0° C. The ice bath was removed, then after 16 h another portion of ethyl isocyanate (11 mg, 0.14 mmol) was added, and the reaction mixture was stirred at 40° C. for 72 h. Volatile material was removed by concentration under vacuum, and the residue was chromatographed (SiO$_2$; dichloromethane to dichloromethane/methanol/25% aq. ammonia solution 90:10:0.25) to afford the title compound (33 mg, 45%). Colorless gum, MS (ISP)=517.3 (M+H)+.

B) Ethyl-carbamic acid (S)-2-[(S)-4-(3-chloro-phenylcarbamoyl)-3-methyl-2-oxo-piperazin-1-yl]-4-((S)-4-hydroxy-6-aza-spiro[2.5]oct-6-yl)-butyl ester The title compound was produced in analogy to example 103 from (S)-4-[(S)-1-ethylcarbamoyloxymethyl-3-((S)-4-hydroxy-6-aza-spiro[2.5]oct-6-yl)-propyl]-2-methyl-3-oxo-piperazine-1-carboxylic acid benzyl ester and 3-chlorophenyl isocyanate. Colorless gum, MS (ISP)=536.3 (M+H)+.

Example 112

Carbonic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester methyl ester

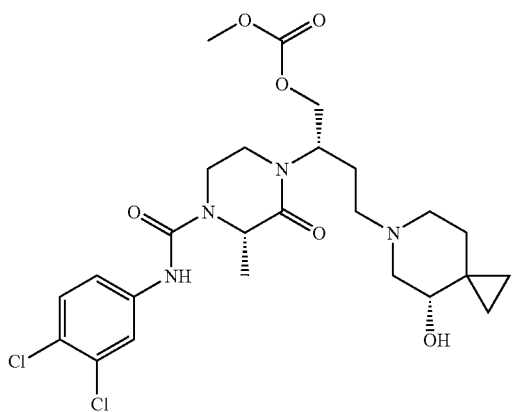

Methyl chloroformate (9 mg, 0.1 mmol) was added at 0° C. to a solution of (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106; 50 mg, 0.10 mmol) in dichloromethane (1 mL). The ice bath was removed, then after 30 min the reaction mixture was cooled to 0° C., treated with diethylamine (4 mg, 50 μmol), and evaporated. Chromatography (SiO₂; dichloromethane to dichloromethane/methanol/25% aq. ammonia solution 90:10:0.25) provided the title compound (52 mg, 93%). White solid, MS (ISP)=557.1 (M+H)⁺.

Example 113

Carbonic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester isopropyl ester

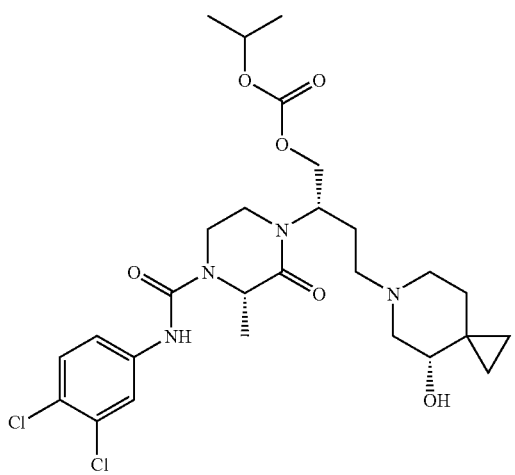

The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106) and isopropyl chloroformate. White solid, MS (ISP)=585.2 (M+H)⁺.

Example 114

2,2-Dimethyl-propionic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester

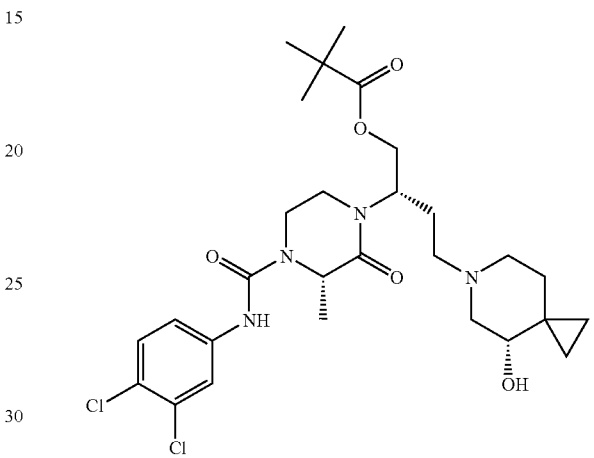

The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106) and pivaloyl chloride. White solid, MS (ISP)=583.1 (M+H)⁺.

Example 115

Isobutyric acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester

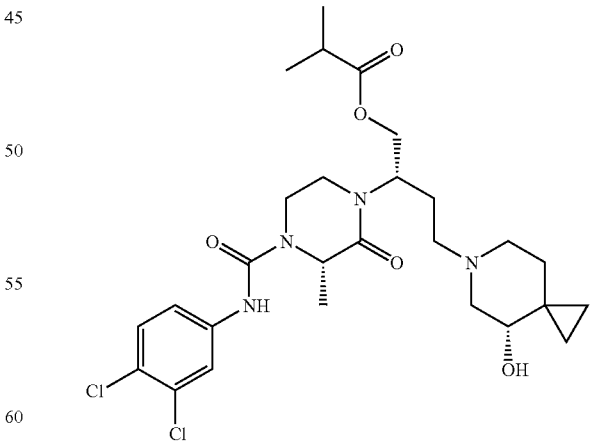

The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106) and isobutyryl chloride. Colorless gum, MS (ISP)=569.2 (M+H)⁺.

Example 116

Hexanoic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester

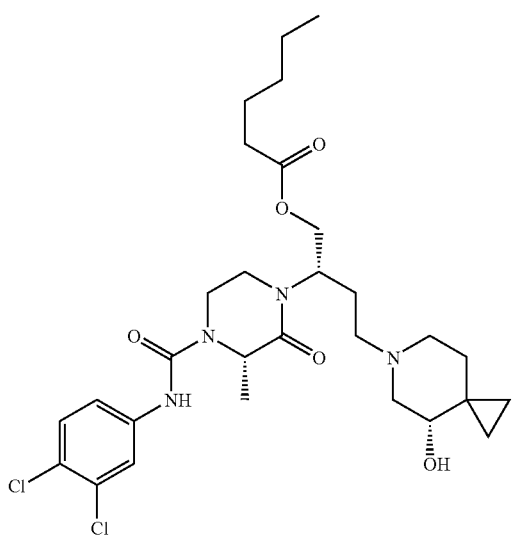

The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106) and hexanoyl chloride. Colorless gum, MS (ISP)=597.2 (M+H)$^+$.

Example 117

Hexadecanoic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106) and palmitoyl chloride. Colorless gum, MS (ISP)=737.6 (M+H)$^+$.

Example 118

Benzoic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester

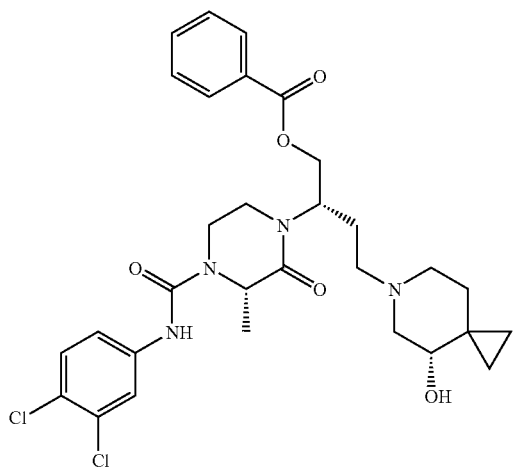

The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106) and benzoyl chloride. Colorless gum, MS (ISP)=603.4 (M+H)$^+$.

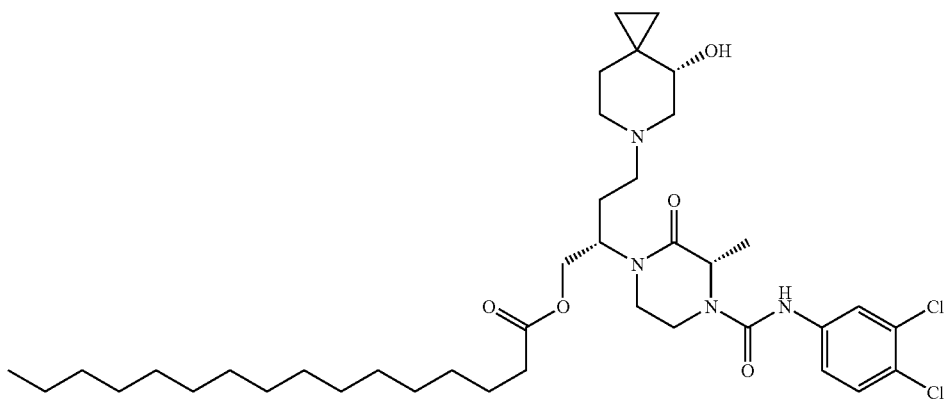

Example 119

4-Methoxy-benzoic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester

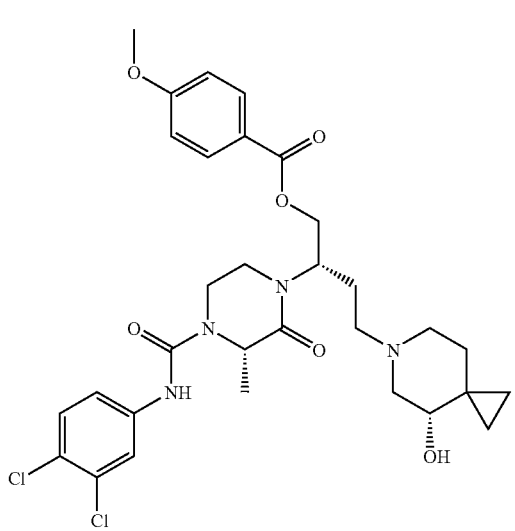

The title compound was produced in analogy to example 112 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid (3,4-dichloro-phenyl)-amide (example 106) and 4-methoxybenzoyl chloride. Colorless gum, MS (ISP)=633.5 (M+H)$^+$.

Example 120

(S)-4-[(S)-2-Hydroxy-3-((S)-4-hydroxy-6-aza-spiro[2.5]oct-6-yl)-propyl]-2-methyl-3-oxo-piperazine-1-carboxylic acid (3,4-dichloro-phenyl)-amide

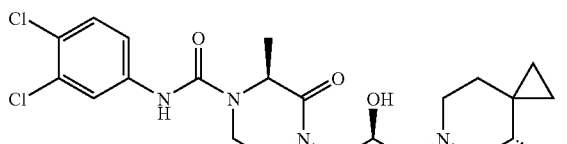

The title compound was produced in analogy to example 103 from (S)-4-[(S)-2-hydroxy-3-((S)-4-hydroxy-6-aza-spiro[2.5]oct-6-yl)-propyl]-2-methyl-3-oxo-piperazine-1-carboxylic acid benzyl ester (intermediate 40) and 3,4-dichlorophenyl isocyanate. White solid, MS (ISP)=485.3 (M+H)$^+$.

Example 121

(S)-4-[(S)-2-Hydroxy-3-((S)-4-hydroxy-6-aza-spiro[2.5]oct-6-yl)-propyl]-2-methyl-3-oxo-piperazine-1-carboxylic acid (3-chloro-phenyl)-amide

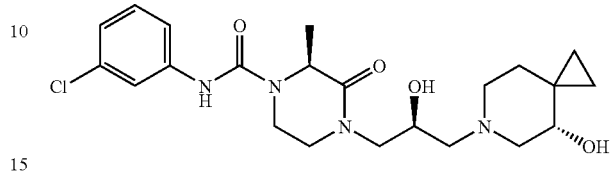

The title compound was produced in analogy to example 103 from (S)-4-[(S)-2-hydroxy-3-((S)-4-hydroxy-6-aza-spiro[2.5]oct-6-yl)-propyl]-2-methyl-3-oxo-piperazine-1-carboxylic acid benzyl ester (intermediate 40) and 3-chlorophenyl isocyanate. White solid, MS (ISP)=451.2 (M+H)$^+$.

Example 122

(S)-4-[(R)-2-Hydroxy-3-((S)-4-hydroxy-6-aza-spiro[2.5]oct-6-yl)-propyl]-2-methyl-3-oxo-piperazine-1-carboxylic acid (3,4-dichloro-phenyl)-amide

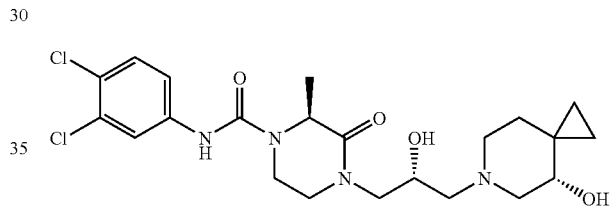

The title compound was produced in analogy to example 103 from (S)-4-[(R)-2-hydroxy-3-((S)-4-hydroxy-6-aza-spiro[2.5]oct-6-yl)-propyl]-2-methyl-3-oxo-piperazine-1-carboxylic acid benzyl ester (intermediate 41) and 3,4-dichlorophenyl isocyanate. White solid, MS (ISP)=485.3 (M+H)$^+$.

Example 123

(S)-4-[(R)-2-Hydroxy-3-((S)-4-hydroxy-6-aza-spiro[2.5]oct-6-yl)-propyl]-2-methyl-3-oxo-piperazine-1-carboxylic acid (3-chloro-phenyl)-amide

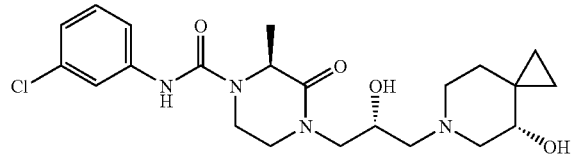

The title compound was produced in analogy to example 103 from (S)-4-[(R)-2-hydroxy-3-((S)-4-hydroxy-6-aza-spiro[2.5]oct-6-yl)-propyl]-2-methyl-3-oxo-piperazine-1-carboxylic acid benzyl ester (intermediate 41) and 3-chlorophenyl isocyanate. White solid, MS (ISP)=451.1 (M+H)$^+$.

Example 124

(S)-4-[(S)-1-Dimethylcarbamoyl-3-((S)-4-hydroxy-6-aza-spiro[2.5]oct-6-yl)-propyl]-2-methyl-3-oxo-piperazine-1-carboxylic acid (3,4-dichloro-phenyl)-amide

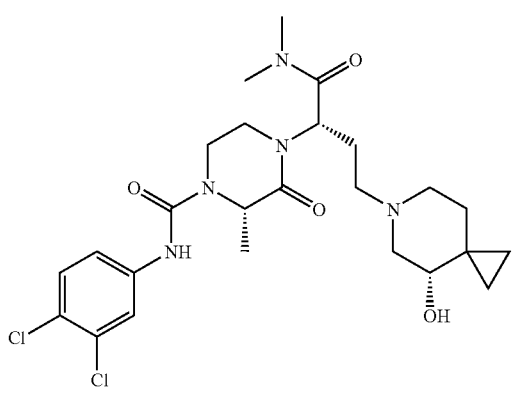

The title compound was produced in analogy to example 103 from (S)-4-[(S)-1-dimethylcarbamoyl-3-((S)-4-hydroxy-6-aza-spiro[2.5]oct-6-yl)-propyl]-2-methyl-3-oxo-piperazine-1-carboxylic acid benzyl ester (intermediate 42) and 3,4-dichlorophenyl isocyanate. White solid, MS (ISP)=540.2 (M+H)$^+$.

Example 125

(S)-4-[(S)-1-Dimethylcarbamoyl-3-((S)-4-hydroxy-6-aza-spiro[2.5]oct-6-yl)-propyl]-2-methyl-3-oxo-piperazine-1-carboxylic acid (3-chloro-phenyl)-amide

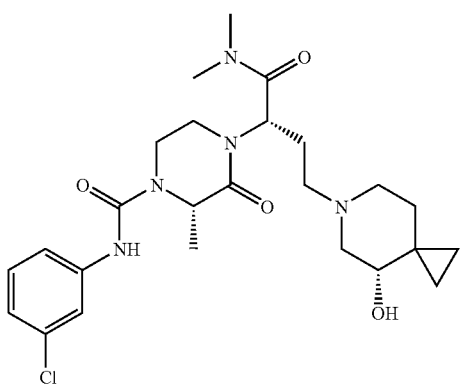

The title compound was produced in analogy to example 103 from (S)-4-[(S)-1-dimethylcarbamoyl-3-((S)-4-hydroxy-6-aza-spiro[2.5]oct-6-yl)-propyl]-2-methyl-3-oxo-piperazine-1-carboxylic acid benzyl ester (intermediate 42) and 3-chlorophenyl isocyanate. White solid, MS (ISP)=506.2 (M+H)$^+$.

Examples 126 and 127

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid phenylamide and phenyl-carbamic acid (S)-4-((S)-4-hydroxy-6-aza-spiro[2.5]oct-6-yl)-2-((S)-3-methyl-2-oxo-4-phenylcarbamoyl-piperazin-1-yl)-butyl ester

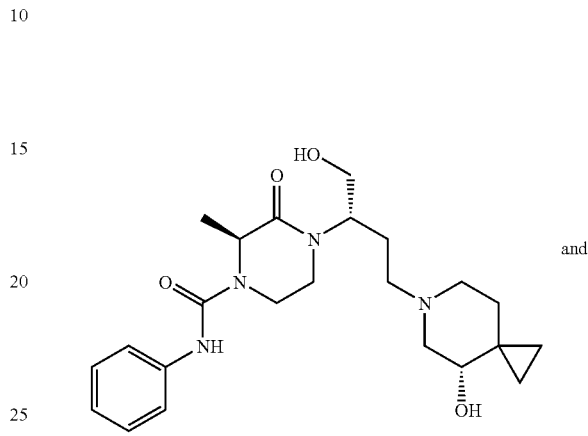

and

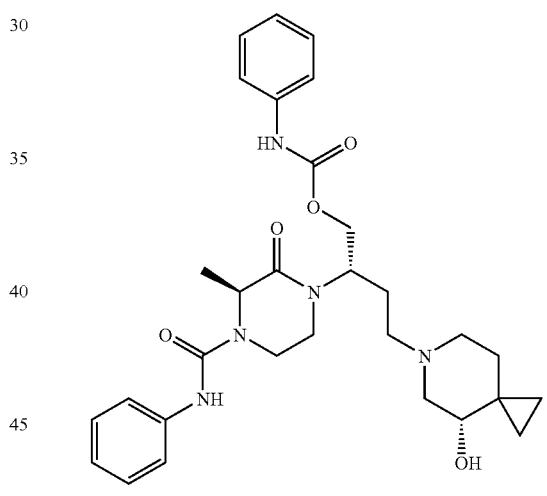

In analogy to example 103, hydrogenation of (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) led to (S)-1-((S)-1-hydroxy-4-((S)-4-hydroxy-6-azaspiro[2.5]octan-6-yl)butan-2-yl)-3-methylpiperazin-2-one, which was reacted with phenyl isocyanate to afford (S)-4-[(S)-3-((S)-4-hydroxy-6-aza-spiro[2.5]oct-6-yl)-1-hydroxymethyl-propyl]-2-methyl-3-oxo-piperazine-1-carboxylic acid phenylamide (example 126; colorless gum, MS (ISP)=431.5 (M+H)$^+$) and phenyl-carbamic acid (S)-4-((S)-4-hydroxy-6-aza-spiro[2.5]oct-6-yl)-2-((S)-3-methyl-2-oxo-4-phenylcarbamoyl-piperazin-1-yl)-butyl ester (example 127; colorless gum, MS (ISP)=550.4 (M+H)$^+$)

Example 128

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3-chloro-4-fluoro-phenyl)-amide

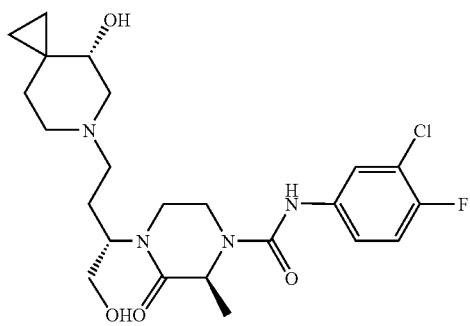

The title compound was produced in analogy to example 103 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and 3-chloro-4-fluorophenyl isocyanate. White solid, MS (ISP)=483.4 (M+H)$^+$.

Example 129

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid naphthalen-2-ylamide

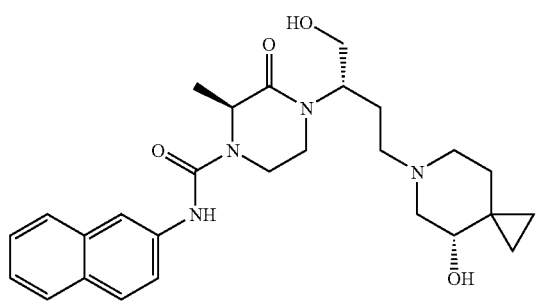

The title compound was produced in analogy to example 103 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and 2-naphthyl isocyanate. White solid, MS (ISP)=481.4 (M+H)$^+$.

Example 130

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (4-chloro-3-trifluoromethyl-phenyl)-amide

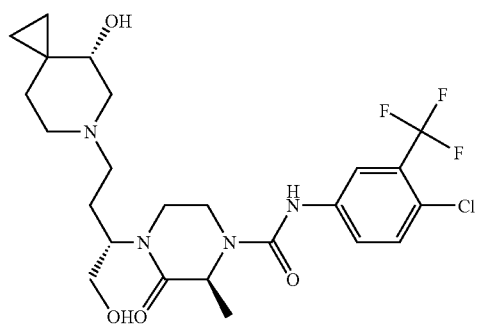

The title compound was produced in analogy to example 103 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and 4-chloro-3-(trifluoromethyl)phenyl isocyanate. Colorless gum, MS (ISP)=533.3 (M+H)$^+$.

Example 131

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3-difluoromethoxy-phenyl)-amide

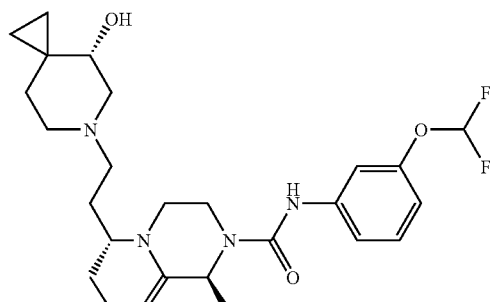

The title compound was produced in analogy to example 103 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and 3-(difluoromethoxy)phenyl isocyanate. Colorless gum, MS (ISP)=497.4 (M+H)$^+$.

Example 132

(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3-fluoro-phenyl)-amide

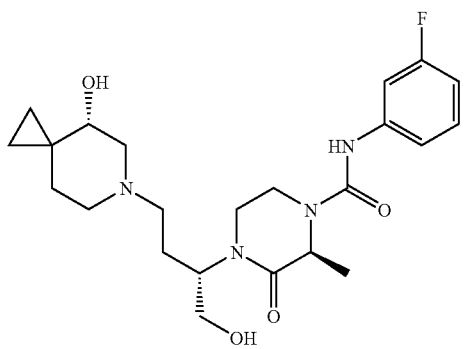

The title compound was produced in analogy to example 103 from (S)-4-[(S)-3-((S)-4-hydroxy-6-aza-spiro[2.5]oct-6-yl)-1-hydroxymethyl-propyl]-2-methyl-3-oxo-piperazine-1-carboxylic acid benzyl ester (intermediate 39) and 3-fluorophenyl isocyanate. White solid, MS (ISP)=483.4 (M+H)$^+$.

Example 133

(S)-4-[(S)-4-((S)-4-Hydroxy-6-aza-spiro[2.5]oct-6-yl)-1-hydroxymethyl-butyl]-2-methyl-3-oxo-piperazine-1-carboxylic acid (3,4-dichloro-phenyl)-amide

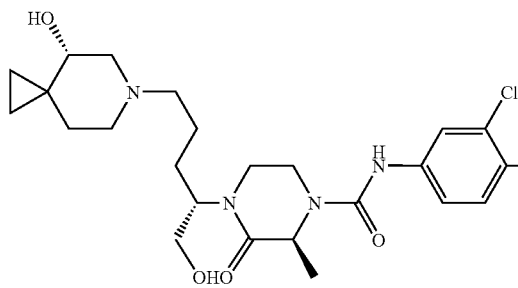

In analogy to example 103, the title compound was produced by hydrogenation of (S)-4-[(S)-4-((S)-4-hydroxy-6-aza-spiro[2.5]oct-6-yl)-1-hydroxymethyl-butyl]-2-methyl-3-oxo-piperazine-1-carboxylic acid benzyl ester (intermediate 43) to (S)-1-[(S)-4-((S)-4-hydroxy-6-aza-spiro[2.5]oct-6-yl)-1-hydroxymethyl-butyl]-3-methyl-piperazin-2-one, followed by reaction with 3,4-dichlorophenyl isocyanate. White solid, MS (ISP)=513.5 (M+H)$^+$.

Example 134

(S)-4-[(S)-4-((S)-4-Hydroxy-6-aza-spiro[2.5]oct-6-yl)-1-hydroxymethyl-butyl]-2-methyl-3-oxo-piperazine-1-carboxylic acid (3-chloro-phenyl)-amide

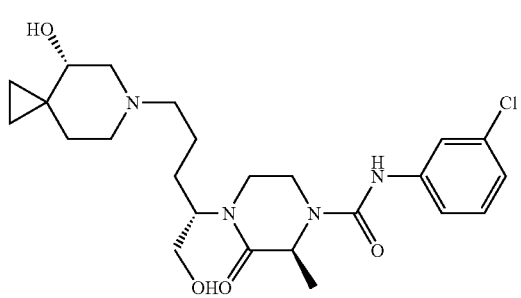

The title compound was produced in analogy to example 103 from (S)-4-[(S)-4-((S)-4-hydroxy-6-aza-spiro[2.5]oct-6-yl)-1-hydroxymethyl-butyl]-2-methyl-3-oxo-piperazine-1-carboxylic acid benzyl ester (intermediate 43) and 3-chlorophenyl isocyanate. White solid, MS (ISP)=479.4 (M+H)$^+$.

Example 135

(S)-4-[(S)-4-((S)-4-Hydroxy-6-aza-spiro[2.5]oct-6-yl)-1-hydroxymethyl-butyl]-2-methyl-3-oxo-piperazine-1-carboxylic acid (3-chloro-4-fluoro-phenyl)-amide

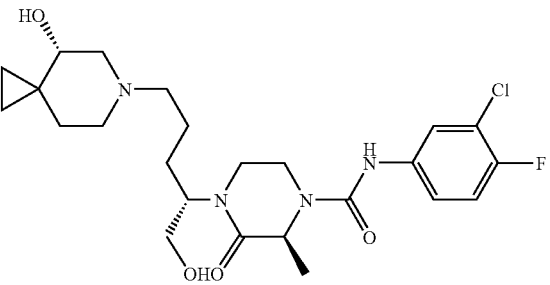

The title compound was produced in analogy to example 103 from (S)-4-[(S)-4-((S)-4-hydroxy-6-aza-spiro[2.5]oct-6-yl)-1-hydroxymethyl-butyl]-2-methyl-3-oxo-piperazine-1-carboxylic acid benzyl ester (intermediate 43) and 3-chloro-4-fluorophenyl isocyanate. White solid, MS (ISP)=497.5 (M+H)$^+$.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| Compound of formula (I) | 3.0 mg |
|---|---|
| Polyethylene glycol 400 | 150.0 mg |
| Acetic acid | q.s. ad pH 5.0 |
| Water for injection solutions | Ad 1.0 ml |

The active ingredient is dissolved in a mixture of polyethylene glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
|---|---|
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesiumstearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavoring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula (I):

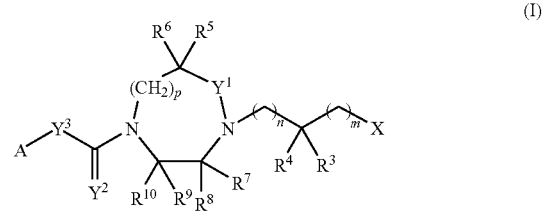

or a pharmaceutically acceptable salt thereof, wherein:

A is phenyl or naphthyl, wherein said phenyl and naphthyl are optionally substituted by one to three substituents selected from the group consisting of halogen, halo $C_{1-6}$ alkyl, and aryl;

X is —$N(R^1)(R^2)$, wherein $R^1$ and $R^2$, together with the nitrogen atom to which they are attached, form a piperindyl or 6-aza-spiro[2.5]oct-6-yl, optionally substituted by one to three substituents independently selected from the group consisting of hydroxy, $C_{1-6}$alkyl and hydroxy $C_{1-6}$alkyl;

$Y^1$ is $C(O)$ or $S(O)_2$; $Y^2$ is O or S; and $Y^3$ is NH or O;

$R^3$ and $R^4$ are independently selected from the group consisting of:
(1) hydrogen,
(2) hydroxy,
(3) $C_{1-6}$ alkyl,
(4) $C_{1-6}$ alkoxy,
(5) $C_{3-7}$ cycloalkyl,
(6) $C_{3-7}$ cycloalkyl $C_{1-6}$ alkyl,
(7) $C_{1-6}$ alkoxycarbonyl,
(8) carboxyl,
(9) carbamoyl,
(10) mono- or di-$C_{1-6}$ alkyl substituted carbamoyl,
(11) $C_{1-6}$ alkoxycarbonyloxy,
(12) mono- or di-$C_{1-6}$ alkyl substituted aminocarbonyloxy,
(13) $C_{1-20}$ alkylcarbonyloxy-$C_{1-6}$ alkyl,
(14) $C_{1-20}$ alkoxycarbonyloxy-$C_{1-6}$ alkyl,
(15) arylcarbonyloxy-$C_{1-6}$ alkyl,
(16) mono- or di-$C_{1-6}$ alkyl substituted aminocarbonyloxy-$C_{1-6}$ alkyl,
(17) hydroxy-$C_{1-6}$ alkyl,
(18) $C_{1-6}$ alkoxy-$C_{1-6}$ alkyl,
(19) halogen or halo $C_{1-6}$ alkyl, and
(20) aryl substituted aminocarbonyloxy-$C_{1-6}$ alkyl, wherein said aryl substituent is optionally substituted by one to three substituents independently selected from the group consisting of halogen, $C_{1-6}$ alkyl, halo $C_{1-6}$ alkyl, $C_{1-6}$ alkoxy and halo $C_{1-6}$ alkoxy; or alternatively, $R^3$ and $R^4$, together with the carbon atom to which they are attached, form a $C_{3-7}$ cycloalkyl or heterocyclyl which is optionally substituted by one to three substituents independently selected from the group consisting of $C_{1-4}$ alkyl, halo $C_{1-4}$ alkyl and halogen;

$R^5$ and $R^6$ are independently hydrogen or $C_{1-6}$ alkyl;
$R^7$, $R^8$, $R^9$ and $R^{10}$ are independently hydrogen or $C_{1-6}$ alkyl;
n is an integer of 0 to 3; m is an integer of 0 to 3; and m+n is an integer of 1 to 5; and
p is 0 or 1.

2. A compound of claim 1, wherein $R^3$ and $R^4$ are, independently selected from the group consisting of: hydrogen, hydroxy, $C_{1-6}$ alkyl, $C_{1-6}$ alkoxy, $C_{3-7}$ cycloalkyl, $C_{3-7}$ cycloalkyl $C_{1-6}$ alkyl, $C_{1-6}$ alkoxycarbonyl, carboxyl, carbamoyl, mono- or di-$C_{1-6}$ alkyl substituted carbamoyl, $C_{1-6}$ alkoxycarbonyloxy, mono- or di-$C_{1-6}$ alkyl substituted aminocarbonyloxy, hydroxy-$C_{1-6}$ alkyl, $C_{1-6}$ alkoxy-$C_{1-6}$ alkyl, halogen, and halo $C_{1-6}$ alkyl; or alternatively $R^3$ and $R^4$, together with the carbon atom to which they are attached, form $C_{3-7}$ cycloalkyl or heterocyclyl optionally substituted by one to three substituents independently selected from the group consisting of $C_{1-4}$ alkyl, halo $C_{1-4}$ alkyl and halogen.

3. A compound of claim 1, wherein A is phenyl substituted by one or two halogen atoms independently selected from the group consisting of chlorine and fluorine.

4. A compound of claim 1, wherein A is 3-chlorophenyl or 3,4-dichlorophenyl.

5. A compound of claim 1, wherein m+n is an integer of 1 to 3.

6. A compound of claim 1, wherein m+n is 2.

7. A compound of claim 1 wherein one of $R^3$ and $R^4$ is preferably hydrogen and the other is selected from the group consisting of hydrogen, hydroxy, $C_{1-6}$ alkoxy, $C_{1-6}$ alkoxycarbonyl, di-$C_{1-6}$ alkyl substituted carbamoyl, $C_{1-6}$ alkoxycarbonyloxy, mono- or di-$C_{1-6}$ alkyl substituted aminocarbonyloxy, hydroxy-$C_{1-6}$ alkyl, $C_{1-6}$ alkoxy-$C_{1-6}$ alkyl, $C_{1-20}$ alkylcarbonyloxy-$C_{1-6}$ alkyl, $C_{1-20}$alkoxycarbonyloxy-$C_{1-6}$ alkyl, phenylcarbonyloxy-$C_{1-6}$ alkyl, mono- or di-$C_{1-6}$ alkyl substituted aminocarbonyloxy-$C_{1-6}$ alkyl, and phenyl substituted aminocarbonyloxy-$C_{1-6}$ alkyl; wherein said phenyl portion of said phenylcarbonyloxy-$C_{1-6}$ alkyl or phenyl substituted aminocarbonyloxy-$C_{1-6}$ alkyl is optionally substituted by one to three substituents independently selected from the group consisting of halogen, $C_{1-6}$ alkyl, halo $C_{1-6}$ alkyl, $C_{1-6}$ alkoxy, and halo $C_{1-6}$ alkoxy.

8. A compound of claim 1 wherein one of $R^3$ and $R^4$ is hydrogen and the other is hydrogen, hydroxy, hydroxy-$C_{1-6}$ alkyl, $C_{1-6}$ alkoxy-$C_{1-6}$ alkyl, $C_{1-6}$ alkylcarbonyloxy-$C_{1-6}$ alkyl or phenylcarbonyloxy-$C_{1-6}$ alkyl.

9. A compound of claim 1, wherein n is 0, m is 2 and one of $R^3$ and $R^4$ is hydrogen, and the other is hydrogen, $C_{1-6}$ alkoxycarbonyl, hydroxy-$C_{1-6}$ alkyl, $C_{1-6}$ alkoxy-$C_{1-6}$ alkyl, or mono- or di-$C_{1-6}$ alkyl substituted carbamoyl.

10. A compound of claim 1, wherein both $R^3$ and $R^4$ are hydrogen.

11. A compound of claim 1, wherein one of $R^5$ and $R^6$ is hydrogen or $C_{1-6}$ alkyl, and the other is hydrogen; and wherein $R^7$, $R^8$, $R^9$ and $R^{10}$ are hydrogen.

12. A compound of claim 1, wherein one of $R^5$ and $R^6$ is methyl and the other is hydrogen, and wherein $R^7$, $R^8$, $R^9$ and $R^{10}$ are hydrogen.

13. A compound of claim 1 wherein $Y^1$ is $C(O)$.

14. A compound of claim 1, wherein $Y^2$ is O.

15. A compound of claim 1, wherein $Y^3$ is NH.

16. A compound of claim 1, selected from the group consisting of:
4-[(S)-3-((S)-4-Hydroxy-6-aza-spiro[2.5]oct-6-yl)-1-hydroxymethyl-propyl]-5-oxo-[1,4]diazepane-1-carboxylic acid (3-chloro-phenyl)-amide,
(S)-2-Methyl-3-oxo-4-(3-piperidin-1-yl-propyl)-piperazine-1-carboxylic acid (3,4-dichloro-phenyl)-amide,
(S)-4-[3-((S)-4-Hydroxy-6-aza-spiro[2.5]oct-6-yl)-propyl]-2-methyl-3-oxo-piperazine-1-carboxylic acid (3,4-dichloro-phenyl)-amide,
(S)-4-[3-((3S,5S)-3-Hydroxy-5-methyl-piperidin-1-yl)-propyl]-2-methyl-3-oxo-piperazine-1-carboxylic acid (3,4-dichloro-phenyl)-amide,
(S)-4-[3-((3S,4S)-3-Hydroxy-4-methyl-piperidin-1-yl)-propyl]-2-methyl-3-oxo-piperazine-1-carboxylic acid (3,4-dichloro-phenyl)-amide,
(R)-4-[(S)-3-((S)-4-Hydroxy-6-aza-spiro[2.5]oct-6-yl)-1-methoxymethyl-propyl]-2-methyl-5-oxo-[1,4]diazepane-1-carboxylic acid (3-chloro-phenyl)-amide,
(S)-4-[(S)-3-((S)-4-Hydroxy-6-aza-spiro[2.5]oct-6-yl)-1-methoxymethyl-propyl]-2-methyl-3-oxo-piperazine-1-carboxylic acid (3,4-dichloro-phenyl)-amide,
(S)-4-[(S)-3-((S)-4-Hydroxy-6-aza-spiro[2.5]oct-6-yl)-1-methoxymethyl-propyl]-2-methyl-3-oxo-piperazine-1-carboxylic acid (3-chloro-phenyl)-amide,
(S)-4-[4-((S)-4-Hydroxy-6-aza-spiro[2.5]oct-6-yl)-butyl]-2-methyl-3-oxo-piperazine-1-carboxylic acid (3-chloro-phenyl)-amide, (S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3,4-dichloro-phenyl)-amide,
(S)-4-[(S)-3-((S)-4-Hydroxy-6-aza-spiro[2.5]oct-6-yl)-1-hydroxymethyl-propyl]-2-methyl-3-oxo-piperazine-1-carboxylic acid (3-chloro-phenyl)-amide,
Acetic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester,
Acetic acid (S)-2-[(S)-4-(3-chloro-phenylcarbamoyl)-3-methyl-2-oxo-piperazin-1-yl]-4-((S)-4-hydroxy-6-aza-spiro[2.5]oct-6-yl)-butyl ester,
2,2-Dimethyl-propionic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester,
Benzoic acid (S)-2-[(S)-4-(3,4-dichloro-phenylcarbamoyl)-3-methyl-2-oxo-piperazin-1-yl]-4-((S)-4-hydroxy-6-aza-spiro[2.5]oct-6-yl)-butyl ester, and
(S)-4-[(S)-4-((S)-4-Hydroxy-6-aza-spiro[2.5]oct-6-yl)-1-hydroxymethyl-butyl]-2-methyl-3-oxo-piperazine-1-carboxylic acid (3,4-dichloro-phenyl)amide.

17. A pharmaceutical composition comprising a therapeutically effective amount of a compound of formula I according to claim 1 and a pharmaceutically acceptable carrier.

18. A process for manufacturing compounds of formula (I):

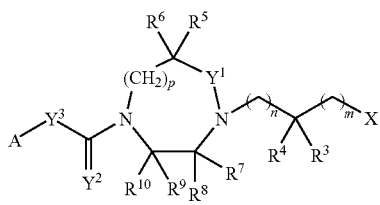

(I)

comprising a step of reacting compounds of formula (4):

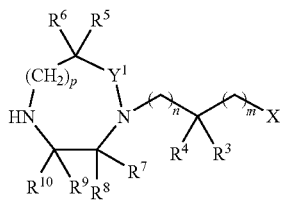

4 with compounds of formula (5A):

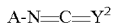    (5A)

or
compounds of formula (5B):

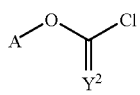    (5B)

or
compounds of formula (5C):

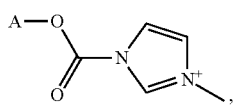    (5C)

wherein A, X, Y$^1$, Y$^2$, R$^3$, R$^4$, R$^5$, R$^6$, R$^7$, R$^8$, R$^9$, R$^{10}$, m, n and p are as defined in claim 1.

19. A process for manufacturing compounds of formula (I):

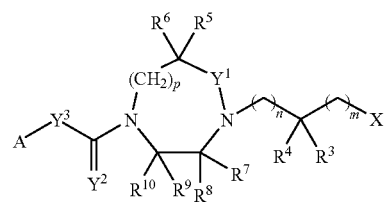

(I)

comprising a step of reacting compounds of formula a (41):

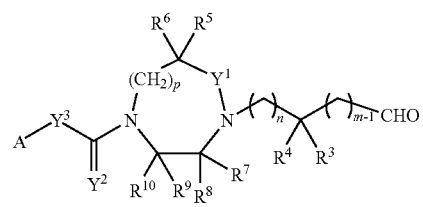

41 with compounds of formula HN(R$^1$)(R$^2$),
wherein A, X, Y$^1$, Y$^2$, Y$^3$, R$^1$, R$^2$, R$^3$, R$^4$, R$^5$, R$^6$, R$^7$, R$^8$, R$^9$, R$^{10}$, m, n and p are as defined in claim 1.

20. A compound of claim 1, wherein:

A is phenyl substituted by one or two halogen atoms independently selected from the group consisting of chlorine and fluorine;

Y$^1$ is C(O);

Y$^2$

Y$^3$ is NH;

one of R$^3$ and R$^4$ is preferably hydrogen and the other is selected from the group consisting of hydrogen, hydroxy, C$_{1-6}$ alkoxy, C$_{1-6}$ alkoxycarbonyl, di-C$_{1-6}$ alkyl substituted carbamoyl, C$_{1-6}$ alkoxycarbonyloxy, mono- or di-C$_{1-6}$ alkyl substituted aminocarbonyloxy, hydroxy-C$_{1-6}$ alkyl, C$_{1-6}$ alkoxy-C$_{1-6}$ alkyl, C$_{1-20}$ alkyl-carbonyloxy-C$_{1-6}$ alkyl, C$_{1-20}$ alkoxycarbonyloxy-C$_{1-6}$ alkyl, phenylcarbonyloxy-C$_{1-6}$ alkyl, mono- or di-C$_{1-6}$ alkyl substituted aminocarbonyloxy-C$_{1-6}$ alkyl, and phenyl substituted aminocarbonyloxy-C$_{1-6}$ alkyl; wherein said phenyl portion of said phenylcarbonyloxy-C$_{1-6}$ alkyl or phenyl substituted aminocarbonyloxy-C$_{1-6}$ alkyl is optionally substituted by one to three substituents independently selected from the group consisting of halogen, C$_{1-6}$ alkyl, halo C$_{1-6}$ alkyl, C$_{1-6}$ alkoxy, and halo C$_{1-6}$ alkoxy;

one of R$^5$ and R$^6$ is hydrogen or C$_{1-6}$ alkyl, and the other is hydrogen;

R$^7$, R$^8$, R$^9$ and R$^{10}$ are hydrogen; and m+n is 2.

21. A compound of claim 1, wherein:

A is 3-chlorophenyl or 3,4-dichlorophenyl;

X is 4-hydroxy-6-aza-spiro[2,5]oct-6-yl;

Y$^1$ is C(O);

Y$^2$ is O;

Y$^3$ is NH;

one of $R^3$ and $R^4$ is hydrogen, and the other is hydrogen, $C_{1-6}$ alkoxycarbonyl, hydroxy-$C_{1-6}$ alkyl, $C_{1-6}$ alkoxy-$C_{1-6}$ alkyl, or mono- or di-$C_{1-6}$ alkyl substituted carbamoyl;

one of $R^5$ and $R^6$ is methyl and the other is hydrogen;

$R^7$, $R^8$, $R^9$ and $R^{10}$ are hydrogen;

n is 0; and m is 2.

22. A compound of claim 21 wherein p is 0.

23. A compound of claim 1 wherein

A is 3-chlorophenyl;

X is 4-hydroxy-6-aza-spiro[2,5]oct-6-yl;

$Y^1$ is C(O);

$Y^2$ is O;

$Y^3$ is NH;

one of $R^3$ and $R^4$ is hydrogen, and the other is hydrogen, $C_{1-6}$ alkoxycarbonyl, hydroxy-$C_{1-6}$ alkyl, $C_{1-6}$ alkoxy-$C_{1-6}$ alkyl, or mono- or di-$C_{1-6}$ alkyl substituted carbamoyl;

one of $R^5$ and $R^6$ is methyl and the other is hydrogen;

$R^7$, $R^8$, $R^9$ and $R^{10}$ are hydrogen;

n is 0;

m is 2; and p is a 0.

* * * * *